US012380971B2

(12) United States Patent
Crowley et al.

(10) Patent No.: US 12,380,971 B2
(45) Date of Patent: Aug. 5, 2025

(54) USER INTERFACES RELATED TO SIGNED CLINICAL DATA

(71) Applicant: Apple Inc., Cupertino, CA (US)

(72) Inventors: Matthew W. Crowley, Sunnyvale, CA (US); Kristin M. Canavan, San Francisco, CA (US); Nicholas D. Felton, Sunnyvale, CA (US); Eamon F. Gilravi, San Francisco, CA (US); Christopher D. Lauritzen, San Francisco, CA (US); Thomas J. Miller, San Jose, CA (US); Charmian B. Naguit, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 227 days.

(21) Appl. No.: 17/832,499

(22) Filed: Jun. 3, 2022

(65) Prior Publication Data

US 2022/0406422 A1 Dec. 22, 2022

Related U.S. Application Data

(60) Provisional application No. 63/243,664, filed on Sep. 13, 2021, provisional application No. 63/197,458, filed on Jun. 6, 2021.

(51) Int. Cl.
*G16H 10/60* (2018.01)
*G06F 21/62* (2013.01)
*G06Q 20/36* (2012.01)

(52) U.S. Cl.
CPC ......... *G16H 10/60* (2018.01); *G06F 21/6245* (2013.01); *G06Q 20/36* (2013.01)

(58) Field of Classification Search
CPC ........ G16H 10/60; G16H 10/65; G16H 20/10; G16H 40/20; G16H 40/63; G06F 21/6245; G06Q 20/36
See application file for complete search history.

(56) References Cited

U.S. PATENT DOCUMENTS 6,416,471 B1  7/2002  Kumar et al.
6,705,972 B1  3/2004  Takano et al.
(Continued)

FOREIGN PATENT DOCUMENTS

CA  2815518 A1  5/2012
CN  102362482 A  2/2012
(Continued)

OTHER PUBLICATIONS

International Preliminary Report on Patentability received for PCT Patent Application No. PCT/US2022/030491, mailed on Dec. 21, 2023, 12 pages.
(Continued)

*Primary Examiner* — Angie Badawi
(74) *Attorney, Agent, or Firm* — DLA Piper LLP (US)

(57) ABSTRACT

The present disclosure generally relates to methods and user interfaces for viewing and managing signed clinical records. In some embodiments, methods and user interfaces for adding a signed clinical record to a computer system are described. In some embodiments, methods and user interfaces for displaying signed clinical records with unsigned clinical records, wherein signed clinical records include a visual indication that they are signed, are described. In some embodiments, methods and user interfaces for adding signed and/or unsigned clinical records related to vision are described.

39 Claims, 33 Drawing Sheets

(56) References Cited

U.S. PATENT DOCUMENTS

| | | |
|---|---|---|
| 7,128,693 B2 | 10/2006 | Brown et al. |
| 7,739,148 B2 | 6/2010 | Suzuki et al. |
| 8,475,339 B2 | 7/2013 | Hwang et al. |
| 8,676,170 B2 | 3/2014 | Porrati et al. |
| 8,784,115 B1 | 7/2014 | Chuang |
| 9,148,483 B1 | 9/2015 | Molettiere et al. |
| 9,224,291 B2 | 12/2015 | Moll-Carrillo et al. |
| 9,557,881 B1 | 1/2017 | Jain et al. |
| 9,589,445 B2 | 3/2017 | White et al. |
| 9,712,629 B2 | 7/2017 | Molettiere et al. |
| 9,813,642 B1 | 11/2017 | Chen et al. |
| 9,940,682 B2 | 4/2018 | Hoffman et al. |
| 10,004,451 B1 | 6/2018 | Proud |
| 10,467,029 B1 | 11/2019 | Lin et al. |
| 11,103,161 B2 | 8/2021 | Williams et al. |
| 11,915,805 B2 | 2/2024 | Crowley et al. |
| 2003/0216971 A1 | 11/2003 | Sick et al. |
| 2003/0226695 A1 | 12/2003 | Mault |
| 2004/0210117 A1 | 10/2004 | Ueno et al. |
| 2005/0075214 A1 | 4/2005 | Brown et al. |
| 2005/0079905 A1 | 4/2005 | Martens |
| 2005/0228735 A1 | 10/2005 | Duquette |
| 2005/0272564 A1 | 12/2005 | Pyles et al. |
| 2006/0098109 A1 | 5/2006 | Ooki |
| 2006/0106741 A1 | 5/2006 | Janarthanan |
| 2007/0056727 A1 | 3/2007 | Newman |
| 2007/0179434 A1 | 8/2007 | Weinert et al. |
| 2008/0200312 A1 | 8/2008 | Tagliabue |
| 2008/0300110 A1 | 12/2008 | Smith et al. |
| 2009/0118100 A1 | 5/2009 | Oliver et al. |
| 2009/0210078 A1 | 8/2009 | Crowley |
| 2009/0216556 A1 | 8/2009 | Martin et al. |
| 2009/0262088 A1 | 10/2009 | Moll-Carrillo et al. |
| 2009/0287103 A1 | 11/2009 | Pillai |
| 2010/0048358 A1 | 2/2010 | Tchao et al. |
| 2010/0060586 A1 | 3/2010 | Pisula et al. |
| 2010/0064255 A1 | 3/2010 | Rottler et al. |
| 2010/0121700 A1 | 5/2010 | Wigder et al. |
| 2010/0131298 A1 | 5/2010 | Buttner et al. |
| 2010/0179833 A1 | 7/2010 | Roizen et al. |
| 2010/0273610 A1 | 10/2010 | Johnson |
| 2010/0280838 A1 | 11/2010 | Bosworth et al. |
| 2011/0066051 A1 | 3/2011 | Moon et al. |
| 2011/0071765 A1 | 3/2011 | Yodfat et al. |
| 2011/0087076 A1 | 4/2011 | Brynelsen et al. |
| 2011/0098928 A1 | 4/2011 | Hoffman et al. |
| 2011/0137678 A1 | 6/2011 | Williams |
| 2011/0195383 A1 | 8/2011 | Weiss |
| 2011/0218407 A1 | 9/2011 | Haberman et al. |
| 2011/0275940 A1 | 11/2011 | Nims et al. |
| 2011/0307821 A1 | 12/2011 | Martens |
| 2012/0041767 A1 | 2/2012 | Hoffman et al. |
| 2012/0071770 A1 | 3/2012 | Grey et al. |
| 2012/0116550 A1 | 5/2012 | Hoffman et al. |
| 2012/0253485 A1 | 10/2012 | Weast et al. |
| 2012/0253488 A1 | 10/2012 | Shaw et al. |
| 2012/0283855 A1 | 11/2012 | Hoffman et al. |
| 2012/0316455 A1 | 12/2012 | Rahman et al. |
| 2012/0317167 A1 | 12/2012 | Rahman et al. |
| 2013/0110264 A1 | 5/2013 | Weast et al. |
| 2013/0115583 A1 | 5/2013 | Gordon et al. |
| 2013/0132028 A1 | 5/2013 | Crankson et al. |
| 2013/0151285 A1 | 6/2013 | Mclaren et al. |
| 2013/0197679 A1 | 8/2013 | Balakrishnan et al. |
| 2013/0231575 A1 | 9/2013 | Erkkila et al. |
| 2013/0238287 A1 | 9/2013 | Hoffman et al. |
| 2013/0245966 A1 | 9/2013 | Burroughs et al. |
| 2013/0332286 A1 | 12/2013 | Medelius et al. |
| 2014/0038781 A1 | 2/2014 | Foley et al. |
| 2014/0067096 A1 | 3/2014 | Aibara |
| 2014/0135592 A1 | 5/2014 | Ohnemus et al. |
| 2014/0135955 A1 | 5/2014 | Burroughs |
| 2014/0143784 A1 | 5/2014 | Mistry et al. |
| 2014/0197946 A1 | 7/2014 | Park et al. |
| 2014/0221790 A1 | 8/2014 | Pacione et al. |
| 2014/0240122 A1 | 8/2014 | Roberts et al. |
| 2014/0244009 A1 | 8/2014 | Mestas |
| 2014/0275852 A1 | 9/2014 | Hong et al. |
| 2014/0336796 A1 | 11/2014 | Agnew |
| 2014/0337451 A1 | 11/2014 | Choudhary et al. |
| 2014/0358012 A1 | 12/2014 | Richards et al. |
| 2014/0371887 A1 | 12/2014 | Hoffman et al. |
| 2015/0057942 A1 | 2/2015 | Self et al. |
| 2015/0067811 A1 | 3/2015 | Agnew et al. |
| 2015/0130830 A1 | 5/2015 | Nagasaki et al. |
| 2015/0142689 A1 | 5/2015 | Squires |
| 2015/0181314 A1 | 6/2015 | Swanson |
| 2015/0182843 A1 | 7/2015 | Esposito et al. |
| 2015/0185967 A1 | 7/2015 | Ly et al. |
| 2015/0196805 A1 | 7/2015 | Koduri et al. |
| 2015/0217163 A1 | 8/2015 | Amis et al. |
| 2015/0220883 A1 | 8/2015 | Bfar et al. |
| 2015/0288797 A1 | 10/2015 | Vincent |
| 2015/0347711 A1 | 12/2015 | Soli et al. |
| 2015/0364057 A1 | 12/2015 | Catani et al. |
| 2015/0379198 A1 | 12/2015 | Tambasco, Jr. |
| 2015/0379232 A1 | 12/2015 | Mainwaring et al. |
| 2016/0019360 A1 | 1/2016 | Pahwa et al. |
| 2016/0058331 A1 | 3/2016 | Keen et al. |
| 2016/0058336 A1 | 3/2016 | Blahnik et al. |
| 2016/0058337 A1 | 3/2016 | Blahnik et al. |
| 2016/0062464 A1 | 3/2016 | Moussette et al. |
| 2016/0062582 A1 | 3/2016 | Wilson et al. |
| 2016/0089569 A1 | 3/2016 | Blahnik |
| 2016/0135731 A1 | 5/2016 | Drennan |
| 2016/0166195 A1 | 6/2016 | Ra ka et al. |
| 2016/0210099 A1 | 7/2016 | Hampapuram et al. |
| 2016/0235374 A1 | 8/2016 | Miller et al. |
| 2016/0250517 A1 | 9/2016 | Tilvis et al. |
| 2016/0256082 A1 | 9/2016 | Ely et al. |
| 2016/0256741 A1 | 9/2016 | Holma et al. |
| 2016/0263435 A1 | 9/2016 | Venkatraman et al. |
| 2016/0324457 A1 | 11/2016 | Dagum |
| 2016/0328991 A1 | 11/2016 | Simpson et al. |
| 2016/0332025 A1 | 11/2016 | Repka |
| 2016/0346607 A1 | 12/2016 | Rapfogel |
| 2016/0357861 A1 | 12/2016 | Carlhian et al. |
| 2016/0373631 A1 | 12/2016 | Titi et al. |
| 2017/0024531 A1 | 1/2017 | Malaviya |
| 2017/0053542 A1 | 2/2017 | Wilson et al. |
| 2017/0075737 A1 | 3/2017 | Kim et al. |
| 2017/0084196 A1 | 3/2017 | Nusbaum et al. |
| 2017/0087412 A1 | 3/2017 | Blahnik |
| 2017/0124276 A1 | 5/2017 | Tee |
| 2017/0161014 A1 | 6/2017 | Kikugawa et al. |
| 2017/0181678 A1 | 6/2017 | Newberry |
| 2017/0215811 A1 | 8/2017 | Newberry |
| 2017/0220751 A1 | 8/2017 | Davis et al. |
| 2017/0237694 A1 | 8/2017 | Choudhary et al. |
| 2017/0239525 A1 | 8/2017 | Kim et al. |
| 2017/0243508 A1 | 8/2017 | Cheng et al. |
| 2017/0249417 A1 | 8/2017 | Gosieski et al. |
| 2017/0266531 A1 | 9/2017 | Elford et al. |
| 2017/0274267 A1 | 9/2017 | Blahnik |
| 2017/0281057 A1 | 10/2017 | Blahnik et al. |
| 2017/0294174 A1 | 10/2017 | Albadawi et al. |
| 2017/0300186 A1 | 10/2017 | Kuhar et al. |
| 2017/0329933 A1 | 11/2017 | Brust et al. |
| 2017/0348562 A1 | 12/2017 | Jung et al. |
| 2017/0354845 A1 | 12/2017 | Williams et al. |
| 2017/0357411 A1 | 12/2017 | Williams et al. |
| 2017/0357520 A1 | 12/2017 | De Vries et al. |
| 2018/0052968 A1 | 2/2018 | Hickle et al. |
| 2018/0053200 A1 | 2/2018 | Cronin et al. |
| 2018/0065025 A1 | 3/2018 | Toda et al. |
| 2018/0074462 A1 | 3/2018 | Helder et al. |
| 2018/0074464 A1 | 3/2018 | Essery et al. |
| 2018/0078182 A1 | 3/2018 | Chen et al. |
| 2018/0085629 A1 | 3/2018 | Gu et al. |
| 2018/0137937 A1 | 5/2018 | Gass et al. |
| 2018/0137938 A1 | 5/2018 | Vaddiraju et al. |
| 2018/0140211 A1 | 5/2018 | Nakazawa et al. |
| 2018/0140927 A1 | 5/2018 | Kito et al. |
| 2018/0226150 A1 | 8/2018 | Hayter et al. |

(56) References Cited

U.S. PATENT DOCUMENTS

| | | |
|---|---|---|
| 2018/0350451 A1 | 12/2018 | Ohnemus et al. |
| 2018/0351781 A1 | 12/2018 | Movsisyan et al. |
| 2019/0104951 A1 | 4/2019 | Valys et al. |
| 2019/0333614 A1 | 10/2019 | Burger et al. |
| 2019/0336044 A1 | 11/2019 | Williams et al. |
| 2019/0336045 A1 | 11/2019 | Williams et al. |
| 2019/0339849 A1 | 11/2019 | Williams et al. |
| 2019/0341027 A1 | 11/2019 | Vescovi et al. |
| 2020/0100693 A1 | 4/2020 | Velo |
| 2020/0135319 A1 | 4/2020 | Meugels |
| 2020/0143258 A1 | 5/2020 | Kanner et al. |
| 2020/0203012 A1 | 6/2020 | Kamath et al. |
| 2020/0261763 A1 | 8/2020 | Park et al. |
| 2020/0297249 A1 | 9/2020 | Williams et al. |
| 2020/0303063 A1 | 9/2020 | Sharma et al. |
| 2020/0350052 A1 | 11/2020 | Saint et al. |
| 2021/0068714 A1 | 3/2021 | Crowley et al. |
| 2022/0160258 A1 | 5/2022 | Williams et al. |
| 2022/0215909 A1* | 7/2022 | Raj .................. G16H 15/00 |
| 2022/0253537 A1* | 8/2022 | Yao .................. H04W 12/06 |
| 2022/0262485 A1 | 8/2022 | Meschter et al. |
| 2022/0270727 A1* | 8/2022 | Ananda ............. G06K 7/1417 |
| 2022/0273204 A1 | 9/2022 | Kamath et al. |
| 2022/0392588 A1 | 12/2022 | Crowley et al. |
| 2023/0017793 A1 | 1/2023 | Williams et al. |
| 2023/0395223 A1 | 12/2023 | Lauritzen et al. |
| 2024/0005009 A1* | 1/2024 | Khanal ............. G06F 21/6209 |
| 2024/0161888 A1 | 5/2024 | Crowley et al. |
| 2024/0242840 A1 | 7/2024 | Kumar et al. |
| 2024/0306941 A1 | 9/2024 | Williams et al. |

FOREIGN PATENT DOCUMENTS

| | | |
|---|---|---|
| CN | 102448555 A | 5/2012 |
| CN | 103403627 A | 11/2013 |
| CN | 104122994 A | 10/2014 |
| CN | 106415559 A | 2/2017 |
| CN | 106510719 A | 3/2017 |
| CN | 106537397 A | 3/2017 |
| CN | 106709235 A | 5/2017 |
| CN | 107469327 A | 12/2017 |
| CN | 109661678 A | 4/2019 |
| JP | 2004-318503 A | 11/2004 |
| JP | 2005-79814 A | 3/2005 |
| JP | 2008-225585 A | 9/2008 |
| JP | 2010-517725 A | 5/2010 |
| JP | 2010-134825 A | 6/2010 |
| JP | 2010-162297 A | 7/2010 |
| JP | 2010-181280 A | 8/2010 |
| JP | 2011-525648 A | 9/2011 |
| JP | 2012-524640 A | 10/2012 |
| JP | 2013-543156 A | 11/2013 |
| JP | 2013-544140 A | 12/2013 |
| JP | 2014-6732 A | 1/2014 |
| JP | 2014-45782 A | 3/2014 |
| JP | 2014-168685 A | 9/2014 |
| JP | 2014-171831 A | 9/2014 |
| JP | 2015-28686 A | 2/2015 |
| JP | 2015-515287 A | 5/2015 |
| JP | 2016-502875 A | 2/2016 |
| JP | 2016-528016 A | 9/2016 |
| JP | 2016-177151 A | 10/2016 |
| JP | 2016-202751 A | 12/2016 |
| JP | 2017-40981 A | 2/2017 |
| JP | 2017-134689 A | 8/2017 |
| JP | 2017-156267 A | 9/2017 |
| JP | 2017-211994 A | 11/2017 |
| JP | 2017-532069 A | 11/2017 |
| JP | 2019-36226 A | 3/2019 |
| JP | 2019-36328 A | 3/2019 |
| KR | 10-2012-0023657 A | 3/2012 |
| KR | 10-2013-0111569 A | 10/2013 |
| KR | 10-2013-0111570 A | 10/2013 |
| KR | 10-2015-0034416 A | 4/2015 |
| KR | 10-2016-0043854 A | 4/2016 |
| KR | 10-2016-0139922 A | 12/2016 |
| KR | 10-2017-0003608 A | 1/2017 |
| WO | 2009/095908 A2 | 8/2009 |
| WO | 2010/106217 A1 | 9/2010 |
| WO | 2010/126825 A1 | 11/2010 |
| WO | 2011/072111 A2 | 6/2011 |
| WO | 2012/061438 A2 | 5/2012 |
| WO | 2012/061440 A2 | 5/2012 |
| WO | 2013/109916 A1 | 7/2013 |
| WO | 2014/144258 A2 | 9/2014 |
| WO | 2014/200730 A1 | 12/2014 |
| WO | 2015/027133 A1 | 2/2015 |
| WO | 2015/183828 A1 | 12/2015 |
| WO | 2015/198488 A1 | 12/2015 |
| WO | 2016/036582 A2 | 3/2016 |
| WO | 2017/037242 A1 | 3/2017 |
| WO | 2017/213962 A1 | 12/2017 |
| WO | 2018/198022 A1 | 11/2018 |
| WO | 2019/217005 A1 | 11/2019 |

OTHER PUBLICATIONS

International Search Report and Written Opinion received for PCT Patent Application No. PCT/US2023/024338, mailed on Oct. 26, 2023, 16 pages.
Notice of Acceptance received for Australian Patent Application No. 2023203776, mailed on Dec. 12, 2023, 3 pages.
Corrected Notice of Allowance received for U.S. Appl. No. 17/483,380, mailed on Jan. 31, 2024, 2 pages.
Notice of Allowance received for U.S. Appl. No. 16/851,451, mailed on Jan. 31, 2024, 13 pages.
Notice of Allowance received for U.S. Appl. No. 17/483,380, mailed on Nov. 20, 2023, 8 pages.
Office Action received for Australian Patent Application No. 2023203776, mailed on Nov. 7, 2023, 2 pages.
Corrected Notice of Allowance received for U.S. Appl. No. 16/851,451, mailed on Feb. 20, 2024, 3 pages.
Extended European Search Report received for European Patent Application No. 23192409.3, mailed on Feb. 20, 2024, 13 pages.
Non-Final Office Action received for U.S. Appl. No. 17/952,133, mailed on Feb. 28, 2024, 22 pages.
Applicant-Initiated Interview Summary received for U.S. Appl. No. 16/851,451, mailed on Apr. 20, 2023, 4 pages.
Applicant-Initiated Interview Summary received for U.S. Appl. No. 17/483,380, mailed on May 1, 2023, 6 pages.
Applicant-Initiated Interview Summary received for U.S. Appl. No. 17/666,301, mailed on Mar. 28, 2023, 4 pages.
Decision to Grant received for European Patent Application No. 20182116.2, mailed on Mar. 23, 2023, 3 pages.
Final Office Action received for U.S. Appl. No. 16/851,451, mailed on Jun. 1, 2023, 35 pages.
Final Office Action received for U.S. Appl. No. 17/483,380, mailed on Jun. 6, 2023, 11 pages.
Intention to Grant received for European Patent Application No. 19721883.7, mailed on May 11, 2023, 9 pages.
Non-Final Office Action received for U.S. Appl. No. 17/952,133, mailed on Jun. 2, 2023, 28 pages.
Notice of Allowance received for U.S. Appl. No. 17/666,301, mailed on May 4, 2023, 10 pages.
Office Action received for Australian Patent Application No. 2020313970, mailed on Mar. 22, 2023, 4 pages.
Office Action received for Japanese Patent Application No. 2022-502594, mailed on Mar. 20, 2023, 10 pages (5 pages of English Translation and 5 pages of Official Copy).
Supplemental Notice of Allowance received for U.S. Appl. No. 17/666,301, mailed on Jun. 5, 2023, 2 pages.
Supplemental Notice of Allowance received for U.S. Appl. No. 17/666,301, mailed on May 17, 2023, 2 pages.
Office Action received for Australian Patent Application No. 2023241370, mailed on Jun. 24, 2024, 3 pages.
Health Follow-Up with Wearable Medical Device, Vivago Move, XP93061915, Retrieved from the Internet: https://move.vivago.

(56) References Cited

OTHER PUBLICATIONS com/en/wearable-medical-devices/#:~:text=Vivago%20MOVETM%20is%20developed,more%20personalized%20and%20timely%20care. [retrieved on Jul. 6, 2023], Jul. 31, 2021, 4 pages.
International Search Report and Written Opinion received for PCT Patent Application No. PCT/US2023/017428, mailed on Jul. 14, 2023, 17 pages.
Notice of Allowance received for Japanese Patent Application No. 2022-022159, mailed on Aug. 10, 2023, 4 pages (1 page of English Translation and 3 pages of Official Copy).
Vivago Mobile User Manual, XP093061914, retrieved from the Internet: https://vivago.studio.crasman.fi/pub/web/2016/materials/ladattavat+materiaalit/AEN0007-05_Vivago-MOBILE-User-Manual.pdf [retrieved on Jul. 6, 2023], Jul. 4, 2019, 38 pages.
Nakasuji, Yoshito, "Apple Watch", First Edition 1st Printing, Japan, Incorporated Company Technical Hyoronsha, Jun. 15, 2015, 4 pages.
Applicant-Initiated Interview Summary received for U.S. Appl. No. 17/952,133, mailed on Apr. 23, 2024, 3 pages.
Fei et al., "Research on the Open Model of Health and Medical Big Data Sharing", Chinese Journal of Health Informatics and Management, vol. 16, Issue No. 6, Dec. 2019, pp. 649-654 (Official Copy Only) {See Communication Under Rule 37 CFR § 1.98(a)(3)}.
Office Action received for Chinese Patent Application No. 202280040622.X, mailed on May 22, 2024, 20 pages (11 pages of English Translation and 9 pages of Official Copy).
Advisory Action received for U.S. Appl. No. 16/144,849, mailed on Aug. 12, 2019, 5 pages.
Advisory Action received for U.S. Appl. No. 16/144,864, mailed on Jul. 6, 2020, 6 pages.
Advisory Action received for U.S. Appl. No. 16/144,864, mailed on Jul. 29, 2019, 6 pages.
Applicant Initiated Interview Summary received for U.S. Appl. No. 16/144,849, mailed on Jan. 21, 2020, 6 pages.
Applicant Initiated Interview Summary received for U.S. Appl. No. 16/144,864, mailed on Apr. 29, 2020, 4 pages.
Applicant Initiated Interview Summary received for U.S. Appl. No. 16/894,309, mailed on Jan. 26, 2021, 3 pages.
Applicant-Initiated Interview Summary received for U.S. Appl. No. 16/138,809, mailed on Dec. 16, 2020, 7 pages.
Applicant-Initiated Interview Summary received for U.S. Appl. No. 16/138,809, mailed on Jun. 9, 2020, 4 pages.
Applicant-Initiated Interview Summary received for U.S. Appl. No. 16/144,864, mailed on Jun. 22, 2020, 3 pages.
Applicant-Initiated Interview Summary received for U.S. Appl. No. 16/894,309, mailed on Jun. 25, 2021, 4 pages.
Brief Communication Regarding Oral Proceedings received for European Patent Application No. 20182116.2, mailed on Apr. 13, 2022, 3 pages.
CNET, "Google Fit's automatic activity tracking is getting smarter on Android Wear", Available online at: https://www.youtube.com/watch?v=IttzlCid_d8, May 18, 2016, 1 page.
DC Rainmaker, "Garmin Fenix3 New Auto Climb Functionality", Available online at: https://www.youtube.com/watch?v=iuavOSNpVRc, Feb. 19, 2015, 1 page.
Decision on Appeal received for Korean Patent Application No. 10-2019-7025538, mailed on Feb. 24, 2021, 20 pages (4 pages of English Translation and 16 pages of Official Copy).
Decision to Grant received for Danish Patent Application No. PA201870379, mailed on Jul. 5, 2019, 2 pages.
European Search Report received for European Patent Application No. 20182116.2, mailed on Oct. 21, 2020, 4 pages.
Evergreen et al., "Bar Chart", Better Evaluation, Available Online at: https://www.betterevaluation.org/en/evaluation-options/BarChart, Oct. 31, 2014, 8 pages.
Extended European Search Report received for European Patent Application No. 20203526.7, mailed on Jan. 29, 2021, 13 pages.
Final Office Action received for U.S. Appl. No. 16/138,809, mailed on Aug. 27, 2020, 24 pages.
Final Office Action received for U.S. Appl. No. 16/144,849, mailed on Jun. 7, 2019, 29 pages.
Final Office Action received for U.S. Appl. No. 16/144,864, mailed on May 17, 2019, 24 pages.
Final Office Action received for U.S. Appl. No. 16/144,864, mailed on May 28, 2020, 29 pages.
Final Office Action received for U.S. Appl. No. 16/894,309, mailed on Feb. 24, 2021, 30 pages.
"Fitbit App", Available online at: <http://web.archive.org/web/20180114083150/https://www.fitbit.com/au/app>, Jan. 14, 2018, 8 pages.
Garmin, "Fenix 5x Owner's Manual", Online Available at: https://web.archive.org/web/20180127170640/https://static.garmin.com/pumac/fenix5x_OM_EN.pdf, Jan. 27, 2018, 42 pages.
"Graphs and Charts", Online available at: <https://www.teachervision.com/lesson-planning/graph-chart-teacher-resources, retrieved on Dec. 12, 2018, 4 pages.
Intention to Grant received for Danish Patent Application No. PA201870379, mailed on May 2, 2019, 2 pages.
Intention to Grant received for European Patent Application No. 20182116.2, mailed on Jun. 2, 2022, 8 pages.
International Preliminary Report on Patentability received for PCT Patent Application No. PCT/US2019/024570, mailed on Nov. 19, 2020, 10 pages.
International Preliminary Report on Patentability received for PCT Patent Application No. PCT/US2020/042439, mailed on Jan. 27, 2022, 10 pages.
International Search Report and Written Opinion received for PCT Patent Application No. PCT/US2019/024570, mailed on Aug. 8, 2019, 18 pages.
International Search Report and Written Opinion received for PCT Patent Application No. PCT/US2020/042439, mailed on Oct. 9, 2020, 14 pages.
Minutes of the Oral Proceedings received for European Patent Application No. 20182116.2, mailed on May 24, 2022, 7 pages.
"Multi-Set Bar Chart", The Data Visualization Catalogue, Available Online at: https://datavizcatalogue.com/methods/multiset_barchart.html, Feb. 8, 2014, 3 pages.
Non-Final Office Action Received for U.S. Appl. No. 16/144,864, mailed on Dec. 18, 2018, 19 pages.
Non-Final Office Action received for U.S. Appl. No. 16/138,809, mailed on Feb. 28, 2020, 22 pages.
Non-Final Office Action received for U.S. Appl. No. 16/144,849, mailed on Dec. 31, 2018, 28 pages.
Non-Final Office Action received for U.S. Appl. No. 16/144,849, mailed on Sep. 17, 2019, 9 pages.
Non-Final Office Action received for U.S. Appl. No. 16/144,864, mailed on Jan. 31, 2020, 29 pages.
Non-Final Office Action received for U.S. Appl. No. 16/851,451, mailed on May 9, 2022, 26 pages.
Non-Final Office Action received for U.S. Appl. No. 16/894,309, mailed on Oct. 15, 2020, 24 pages.
Notice of Acceptance received for Australian Patent Application No. 2019222943, mailed on May 5, 2020, 3 pages.
Notice of Acceptance received for Australian Patent Application No. 2020204153, mailed on Jul. 6, 2020, 3 pages.
Notice of Acceptance received for Australian Patent Application No. 2020256383, mailed on Aug. 3, 2021, 3 pages.
Notice of Allowance received for Chinese Patent Application No. 202010606407.4, mailed on Jan. 24, 2022, 2 pages (1 page of English Translation and 1 page of Official Copy).
Notice of Allowance received for Japanese Patent Application No. 2018-184532, mailed on Jan. 17, 2022, 4 pages (1 page of English Translation and 3 pages of Official Copy).
Notice of Allowance received for Japanese Patent Application No. 2019-162293, mailed on Apr. 9, 2021, 4 pages (1 page of English Translation and 3 pages of Official Copy).
Notice of Allowance received for Japanese Patent Application No. 2020-104679, mailed on Jan. 4, 2021, 4 pages (1 page of English Translation and 3 pages of Official Copy).
Notice of Allowance received for Korean Patent Application No. 10-2019-7025538, mailed Mar. 10, 2021, 5 pages (2 pages of English Translation and 3 pages of Official Copy).

(56) References Cited

OTHER PUBLICATIONS

Notice of Allowance received for Korean Patent Application No. 10-2020-7026035, mailed on Aug. 23, 2021, 4 pages (2 pages of English Translation and 2 pages of Official Copy).
Notice of Allowance received for Korean Patent Application No. 10-2021-7038005, mailed on Dec. 14, 2021, 4 pages (2 pages of English Translation and 2 pages of Official Copy).
Notice of Allowance received for Korean Patent Application No. 10-2022-7008569, mailed on May 19, 2022, 5 pages (2 pages of English Translation and 3 pages of Official Copy).
Notice of Allowance received for U.S. Appl. No. 16/138,809, mailed on Apr. 16, 2021, 11 pages.
Notice of Allowance received for U.S. Appl. No. 16/138,809, mailed on Jul. 20, 2021, 6 pages.
Notice of Allowance received for U.S. Appl. No. 16/144,849, mailed on Apr. 17, 2020, 2 pages.
Notice of Allowance received for U.S. Appl. No. 16/144,849, mailed on Mar. 6, 2020, 9 pages.
Notice of Allowance received for U.S. Appl. No. 16/144,864, mailed on Feb. 9, 2021, 13 pages.
Notice of Allowance received for U.S. Appl. No. 16/144,864, mailed on Jul. 28, 2020, 27 pages.
Notice of Allowance received for U.S. Appl. No. 16/144,864, mailed on Mar. 12, 2021, 2 pages.
Notice of Allowance received for U.S. Appl. No. 16/144,864, mailed on Mar. 30, 2021, 2 pages.
Notice of Allowance received for U.S. Appl. No. 16/144,864, mailed on Sep. 10, 2020, 3 pages.
Notice of Allowance received for U.S. Appl. No. 16/144,864, mailed on Sep. 16, 2020, 2 pages.
Notice of Allowance received for U.S. Appl. No. 16/144,864, mailed on Sep. 29, 2020, 2 pages.
Notice of Allowance received for U.S. Appl. No. 16/894,309, mailed on Feb. 25, 2022, 9 pages.
Notice of Allowance received for U.S. Appl. No. 16/894,309, mailed on Nov. 5, 2021, 12 pages.
Office Action received for Australian Patent Application No. 2019100495, mailed on Mar. 6, 2020, 3 pages.
Office Action received for Australian Patent Application No. 2019100495, mailed on Mar. 16, 2020, 3 pages.
Office Action received for Australian Patent Application No. 2019100495, mailed on Sep. 17, 2019, 7 pages.
Office Action received for Australian Patent Application No. 2019222943, mailed on Oct. 3, 2019, 3 pages.
Office Action received for Australian Patent Application No. 2020256383, mailed on Jun. 4, 2021, 3 pages.
Office Action received for Chinese Patent Application No. 201910858933.7, mailed on Aug. 18, 2020, 14 pages (7 pages of English Translation and 7 pages of Official Copy).
Office Action received for Chinese Patent Application No. 201910858933.7, mailed on Dec. 30, 2021, 9 pages (4 pages of English Translation and 5 pages of Official Copy).
Office Action received for Chinese Patent Application No. 201910858933.7, mailed on Jun. 29, 2021, 8 pages (3 pages of English Translation and 5 pages of Official Copy).
Office Action received for Chinese Patent Application No. 202010606407.4, mailed on Jan. 27, 2021, 16 pages (7 pages of English Translation and 9 pages of Official Copy).
Office Action received for Chinese Patent Application No. 202010606407.4, mailed on Jun. 2, 2021, 12 pages (5 pages of English Translation and 7 pages of Official Copy).
Office Action received for Chinese Patent Application No. 202010606407.4, mailed on Nov. 18, 2021, 6 pages (3 pages of English Translation and 3 pages of Official Copy).
Office Action received for Danish Patent Application No. PA201870378, mailed on Feb. 25, 2019, 3 pages.
Office Action received for Danish Patent Application No. PA201870378, mailed on Jan. 6, 2020, 3 pages.
Office Action received for Danish Patent Application No. PA201870379, mailed on Feb. 28, 2019, 3 pages.
Office Action received for Danish Patent Application No. PA201870380, mailed on Mar. 5, 2020, 2 pages.
Office Action received for Danish Patent Application No. PA201870380, mailed on Mar. 27, 2019, 4 pages.
Office Action received for Danish Patent Application No. PA201870380, mailed on Sep. 11, 2018, 9 pages.
Office Action received for European Patent Application No. 19721883.7, mailed on Jan. 10, 2020, 4 pages.
Office Action received for European Patent Application No. 19721883.7, mailed on Jun. 15, 2021, 9 pages.
Office Action received for European Patent Application No. 19721883.7, mailed on May 28, 2020, 11 pages.
Office Action received for European Patent Application No. 20182116.2, mailed on May 25, 2021, 9 pages.
Office Action received for European Patent Application No. 20182116.2, mailed on Nov. 6, 2020, 9 pages.
Office Action received for European Patent Application No. 20203526.7, mailed on Nov. 23, 2021, 9 pages.
Office Action received for Japanese Patent Application No. 2018-184532, mailed on Mar. 1, 2021, 11 pages (6 pages of English Translation and 5 pages of Official Copy).
Office Action received for Japanese Patent Application No. 2019-162293, mailed on Jan. 31, 2020, 8 pages (4 pages of English Translation and 4 pages of Official Copy).
Office Action received for Japanese Patent Application No. 2019-162293, mailed on Jul. 27, 2020, 9 pages (5 pages of English Translation and 4 pages of Official Copy).
Office Action received for Japanese Patent Application No. 2020-104679, mailed on Sep. 18, 2020, 13 pages (7 pages of English Translation and 6 pages of Official Copy).
Office Action received for Korean Patent Application No. 10-2019-7025538, mailed on Aug. 15, 2020, 8 pages (4 pages of English Translation and 4 pages of Official Copy).
Office Action received for Korean Patent Application No. 10-2019-7025538, mailed on Feb. 17, 2020, 12 pages (6 pages of English Translation and 6 pages of Official Copy).
Office Action received for Korean Patent Application No. 10-2020-7026035, mailed on Feb. 19, 2021, 13 pages (6 pages of English Translation and 7 pages of Official Copy).
Result of Consultation received for European Patent Application No. 19721883.7, mailed on Oct. 7, 2020, 3 pages.
Rizknows, "TomTom Multisport Cardio Review", Online available at: https://www.youtube.com/watch?v=WoVCzLrSN9A, Sep. 4, 2015, 1 page.
Search Report and Opinion received for Danish Patent Application No. PA201870378, mailed on Sep. 10, 2018, 9 pages.
Search Report and Opinion received for Danish Patent Application No. PA201870379, mailed on Sep. 14, 2018, 9 pages.
Smith, "Garmin Fenix 5 Activity/Smart Watch Review", Online available at: https://www.youtube.com/watch?v=6PkQxXQxpoU, Sep. 2, 2017, 1 page.
SportsTechGuides, "Garmin Fenix 5: How to Add Power Data Fields", Online available at: https://www.youtube.com/watch?v=ZkPptnnXEiQ, Apr. 29, 2017, 2 pages.
SportsTechGuides, "Garmin Fenix 5: How To Set Up Run Alerts", Online available at: https://www.youtube.com/watch?v=gSMwv8vlhB4, May 13, 2017, 2 pages.
Summons to Attend Oral Proceedings received for European Patent Application No. 20182116.2, mailed on Dec. 21, 2021, 7 pages.
Supplemental Notice of Allowance received for U.S. Appl. No. 16/144,849, mailed on Mar. 31, 2020, 2 pages.
Supplemental Notice of Allowance received for U.S. Appl. No. 16/894,309, mailed on Apr. 8, 2022, 3 pages.
Supplemental Notice of Allowance received for U.S. Appl. No. 16/894,309, mailed on Dec. 24, 2021, 2 pages.
Supplemental Notice of Allowance received for U.S. Appl. No. 16/894,309, mailed on Jan. 25, 2022, 2 pages.
"Suunto Spartan Trainer Wrist HR 1.12", Online available at: https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.

(56) References Cited

OTHER PUBLICATIONS

Suunto, "Suunto Spartan—Heart Rate Zones", Online available at: https://www.youtube.com/watch?v=aixfoCnS0OU, Mar. 19, 2018, 2 pages.
Teunmo, "Data field: Visual Pace Alarm", Garmin Forum, Available online at: https://forums.garmin.com/forum/developers/connect-iq/connect-iq-showcase/115996-data-field-visual-pace-alarm, Nov. 17, 2015, 10 pages.
Tomtom, "TomTom Runner & Multi-Sport Reference Guide", Online available at: https://web.archive.org/web/20150908075934/http://download.tomtom.com/open/manuals/Runner_Multi-Sport/refman/TomTom-Runner-Multi-Sport-RG-en-GB.pdf, Sep. 8, 2015, 44 pages.
"Visual Pace Alarm app", Available Online at: https://apps.garmin.com/en-US/apps/3940f3a2-4847-4078-a911-d77422966c82, Oct. 19, 2016, 1 page.
Wesley, "Apple Watch Series 1", Online available at: http://toolbox.info/blog/archives/1737-unknown.html, May 28, 2015, 5 pages (Official Copy Only). {See Communication under 37 CFR § 1.98(a) (3)}.
YouTube, "Apple Watch Series 3", Online available at: https://www.youtube.com/watch?v=iBPr9gEfkK8, Nov. 21, 2017, 15 pages (Official Copy Only). {See Communication under 37 CFR § 1.98(a) (3)}.
Zlelik, "Garmin Fenix 5 Open Water Swimming Activity Demo", Online available at: https://www.youtube.com/watch?v=iSVhdvw2dcs, Jun. 9, 2017, 1 page.
Applicant Initiated Interview Summary received for U.S. Appl. No. 17/483,380, mailed on Apr. 26, 2022, 4 pages.
Applicant-Initiated Interview Summary received for U.S. Appl. No. 16/851,451, mailed on Aug. 5, 2022, 3 pages.
Applicant-Initiated Interview Summary received for U.S. Appl. No. 16/851,451, mailed on Nov. 29, 2022, 4 pages.
Applicant-Initiated Interview Summary received for U.S. Appl. No. 17/483,380, mailed on Aug. 29, 2022, 5 pages.
Brief Communication Regarding Oral Proceedings received for European Patent Application No. 20203526.7, mailed on Dec. 23, 2022, 4 pages.
Brief Communication Regarding Oral Proceedings received for European Patent Application No. 20203526.7, mailed on Jan. 18, 2023, 1 page.
Care Zone Inc., "Manage your health, without the headache", Available online at: https://carezone.com/, 2020, 3 pages.
Careclinic Software Inc., "CareClinic—Tracker, Reminder", Version 3.5, retrieved on Jun. 14, 2022, 2 pages.
Circadian Design, Inc., "Round Health", Version 2.5.5, retrieved on Jun. 14, 2022, 1 page.
Devpost, "RxMinder", Availabe online at: https://devpost.com/software/rxminder-jocltp, retrieved on Apr. 5, 2022, 7 pages.
Final Office Action received for U.S. Appl. No. 16/851,451, mailed on Oct. 20, 2022, 31 pages.
Final Office Action received for U.S. Appl. No. 17/483,380, mailed on Jun. 2, 2022, 21 pages.
Groove Health, "EveryDose: Medication Reminder", Version 3.1.12, retrieved on Jun. 14, 2022, 1 page.
"How it works—mediteo-App", Available online at: https://www.mediteo.com/en/features/, retrieved on Apr. 5, 2022, 3 pages.
Intention to Grant received for European Patent Application No. 20182116.2, mailed on Nov. 11, 2022, 9 pages.
Intention to Grant received for European Patent Application No. 20203526.7, mailed on Feb. 10, 2023, 9 pages.
International Search Report and Written Opinion received for PCT Patent Application No. PCT/US2022/030491, mailed on Sep. 5, 2022, 15 pages.
Licea Sergio, "Pill Reminder—All in One", retrieved on Jun. 14, 2022, 1 page.
"Mango Health", Version 4.1.5.18644, retrieved on Jun. 14, 2022, 1 page.
Medfox Digital, S.R.O., "Medfox Pill Reminder & Tracker", Version 1.5, retrieved on Jun. 14, 2022, 1 page.
Medisafe Project Ltd., "Medisafe", Version 8.0.23, Build 11241, 2020, 1 page.
Nakasuji, Yoshito, "Apple Watch", First Edition 1st Printing, Japan, Incorporated Company Technical Hyoronsha, Jun. 15, 2015, 4 pages (Official copy only).
Non-Final Office Action received for U.S. Appl. No. 16/851,451, mailed on Feb. 24, 2023, 28 pages.
Non-Final Office Action received for U.S. Appl. No. 17/483,380, mailed on Feb. 2, 2022, 19 pages.
Office Action received for U.S. Appl. No. 17/483,380, mailed on Feb. 9, 2023, 25 pages.
Non-Final Office Action received for U.S. Appl. No. 17/666,301, mailed on Feb. 16, 2023, 24 pages.
Notice of Acceptance received for Australian Patent Application No. 2021266294, mailed on Mar. 3, 2023, 3 pages.
Notice of Allowance received for Chinese Patent Application No. 202210238202.4, mailed on Jan. 13, 2023, 7 pages (3 pages of English Translation and 4 pages of Official Copy).
Office Action received for Australian Patent Application No. 2020313970, mailed on Dec. 22, 2022, 3 pages.
Office Action received for Australian Patent Application No. 2021266294, mailed on Nov. 11, 2022, 3 pages.
Office Action received for Japanese Patent Application No. 2022-022159, mailed on Feb. 20, 2023, 10 pages (5 pages of English Translation and 5 pages of Official Copy).
Result of Consultation received for European Patent Application No. 20203526.7, mailed on Jan. 13, 2023, 3 pages.
Selby Karen, "10 Best Medication Tracker Apps", Available online at: https://www.asbestos.com/treatment/drugs/medication-tracker-apps/, retrieved on Apr. 5, 2022, 18 pages.
Smartpatient GMBH, "MyTherapy: Medication Reminder", Version 3.89, retrieved on Jun. 14, 2022, 2 pages.
Summons to Attend Oral Proceedings received for European Patent Application No. 20203526.7, mailed on Jun. 23, 2022, 9 pages.
Final Office Action received for U.S. Appl. No. 17/952,133, mailed on Sep. 26, 2023, 20 pages.
Advisory Action received for U.S. Appl. No. 17/952,133, mailed on Oct. 20, 2023, 7 pages.
Office Action received for European Patent Application No. 20751022.3, mailed on Oct. 19, 2023, 8 pages.
Advisory Action received for U.S. Appl. No. 17/483,380, mailed on Aug. 30, 2023, 4 pages.
Decision to Grant received for European Patent Application No. 19721883.7, mailed on Aug. 31, 2023, 4 pages.
Applicant-Initiated Interview Summary received for U.S. Appl. No. 17/483,380, mailed on Jul. 3, 2023, 4 pages.
Applicant-Initiated Interview Summary received for U.S. Appl. No. 17/952,133, mailed on Jul. 3, 2023, 4 pages.
Decision to Grant received for European Patent Application No. 20203526.7, mailed on Jun. 22, 2023, 4 pages.
Notice of Acceptance received for Australian Patent Application No. 2020313970, mailed on Jun. 22, 2023, 3 pages.
Examiner-Initiated Interview received for U.S. Appl. No. 18/418,029, mailed on Nov. 26, 2024, 5 pages.
International Preliminary Report on Patentability received for PCT Patent Application No. PCT/US2023/017428, mailed on Oct. 24, 2024, 11 pages.
International Preliminary Report on Patentability received for PCT Patent Application No. PCT/US2023/024338, mailed on Dec. 19, 2024, 11 pages.
Non-Final Office Action received for U.S. Appl. No. 18/418,029, mailed on Nov. 7, 2024, 32 pages.
Notice of Acceptance received for Australian Patent Application No. 2023241370, mailed on Sep. 20, 2024, 3 pages.
Notice of Allowance received for Chinese Patent Application No. 202280040622.X, mailed on Sep. 2, 2024, 4 pages (1 page of English Translation and 3 pages of Official Copy).
Notice of Allowance received for Japanese Patent Application No. 2023-133506, mailed on Nov. 22, 2024, 4 pages (1 page of English Translation and 3 pages of Official Copy).
Notice of Allowance received for Korean Patent Application No. 10-2022-7026884, mailed on Jul. 30, 2024, 8 pages (2 pages of English Translation and 6 pages of Official Copy).
Office Action received for Australian Patent Application No. 2024200284, mailed on Sep. 30, 2024, 2 pages.

(56) References Cited

OTHER PUBLICATIONS

Office Action received for European Patent Application No. 23192409.3, mailed on Dec. 10, 2024, 9 pages.

Office Action received for Japanese Patent Application No. 2023-128646, mailed on Nov. 25, 2024, 6 pages (3 pages of English Translation and 3 pages of Official Copy).

Office Action received for Japanese Patent Application No. 2023-133506, mailed on Sep. 20, 2024, 6 pages (3 pages of English Translation and 3 pages of Official Copy).

Office Action received for Korean Patent Application No. 10-2022-7001604, mailed on Nov. 15, 2024, 17 pages (7 pages of English Translation and 10 pages of Official Copy).

Notice of Acceptance received for Australian Patent Application No. 2024200284, mailed on Jan. 16, 2025, 3 pages.

Office Action received for Chinese Patent Application No. 202210189383.6, mailed on Jan. 13, 2025, 23 pages (13 pages of English Translation and 10 pages of Official Copy).

Notice of Allowance received for Japanese Patent Application No. 2022-502594, mailed on Jul. 7, 2023, 4 pages (1 page of English Translation and 3 pages of Official Copy).

Board Opinion received for Chinese Patent Application No. 201910858933.7, mailed on Mar. 24, 2025, 13 pages (5 pages of English Translation and 8 pages of Official Copy).

Final Office Action received for U.S. Appl. No. 18/418,029, mailed on Mar. 18, 2025, 42 pages.

Notice of Allowance received for Japanese Patent Application No. 2023-128646, mailed on Mar. 7, 2025, 4 pages (1 page of English Translation and 3 pages of Official Copy).

Office Action received for European Patent Application No. 22743618.5, mailed on Mar. 5, 2025, 7 pages.

Office Action received for Chinese Patent Application No. 202080051210.7, mailed on Feb. 11, 2025, 15 pages (7 pages of English Translation and 8 pages of Official Copy).

Dan—Dan et al., "National Physical Monitoring and Scientific Fitness Exercise Guidance Client Based on iOS", Computer Technology and Development, vol. 27, No. 12, Dec. 2017, pp. 161-165 (Official Copy Only). {See Communication under Rule 37 CFR § 1.98(a)(3)}.

\* cited by examiner

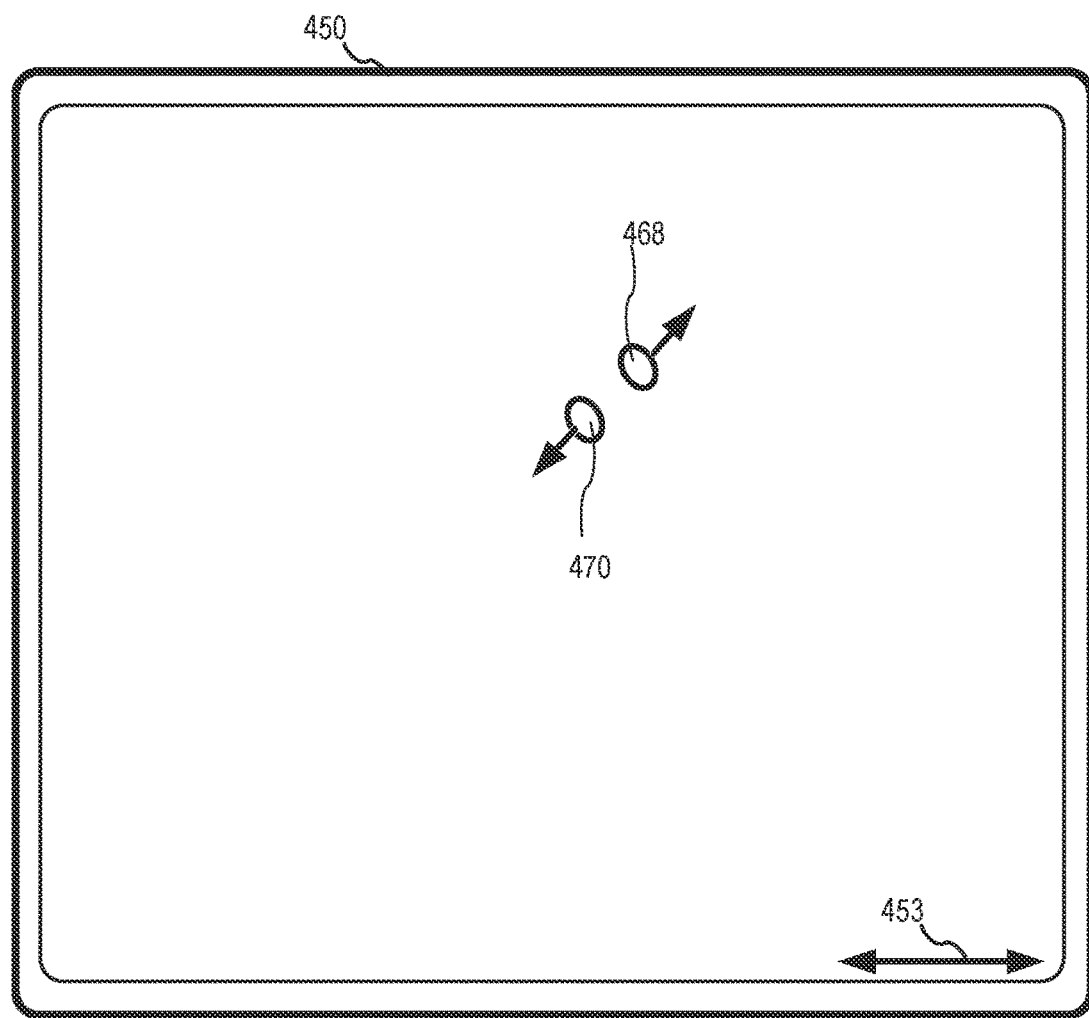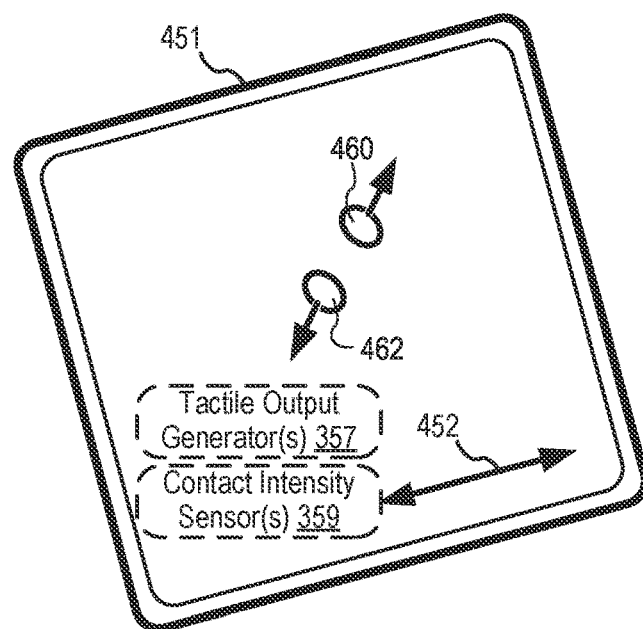
*FIG. 4B*

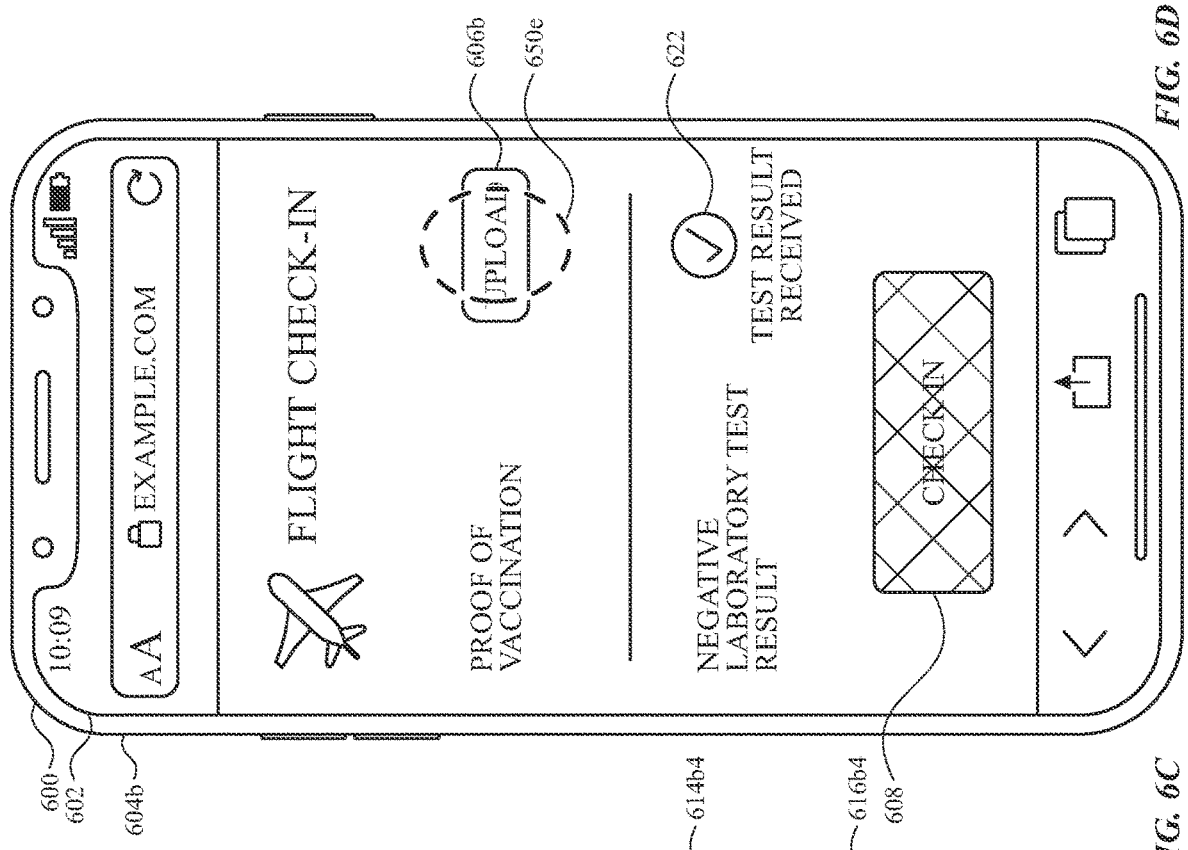
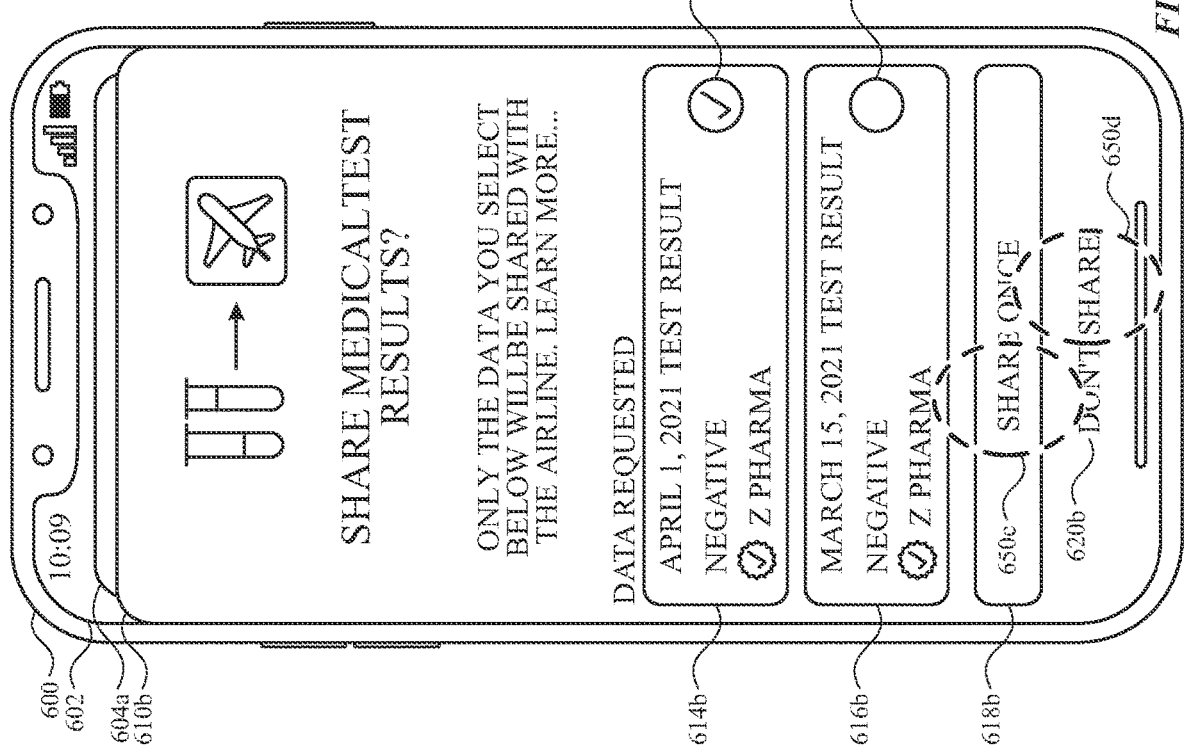
FIG. 6C
FIG. 6D

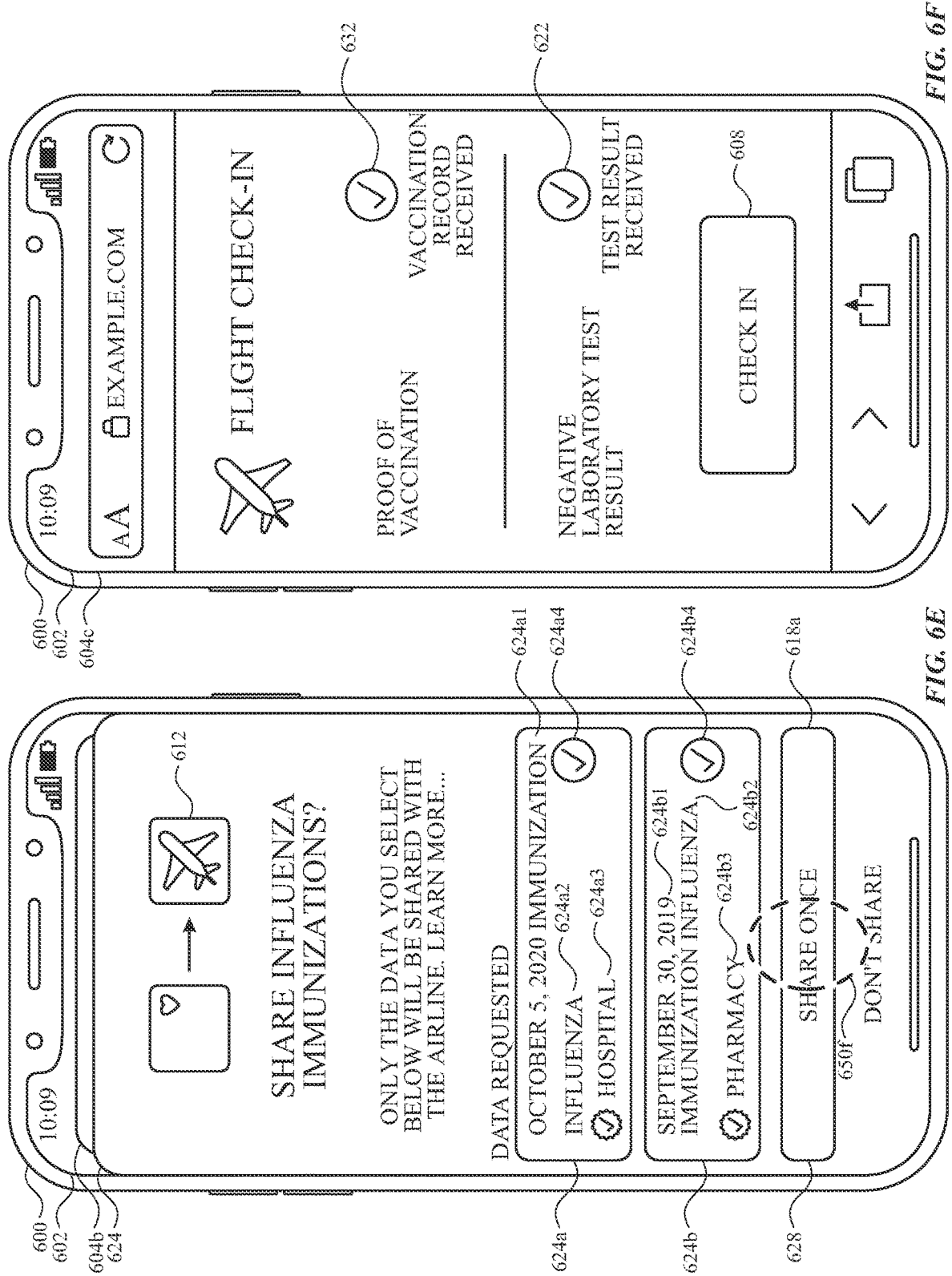

700

702
Receiving, via the one or more input devices, a request for a clinical record that satisfies a first set of criteria.

704
In response to receiving the request for a clinical record that satisfies the first set of criteria:

706
In accordance with a determination that the computer system has access to one or more clinical records that satisfy the first set of criteria, displaying, via the display generation component a sharing user interface, wherein the sharing user interface includes a user-interactive graphical user interface object that, when selected, initiates a process for sharing a first clinical record of the one or more clinical records with one or more external electronic devices.

708
In accordance with a determination that the computer system does not have access to one or more clinical records that satisfy the first set of criteria, forego displaying the sharing user interface.

*FIG. 7*

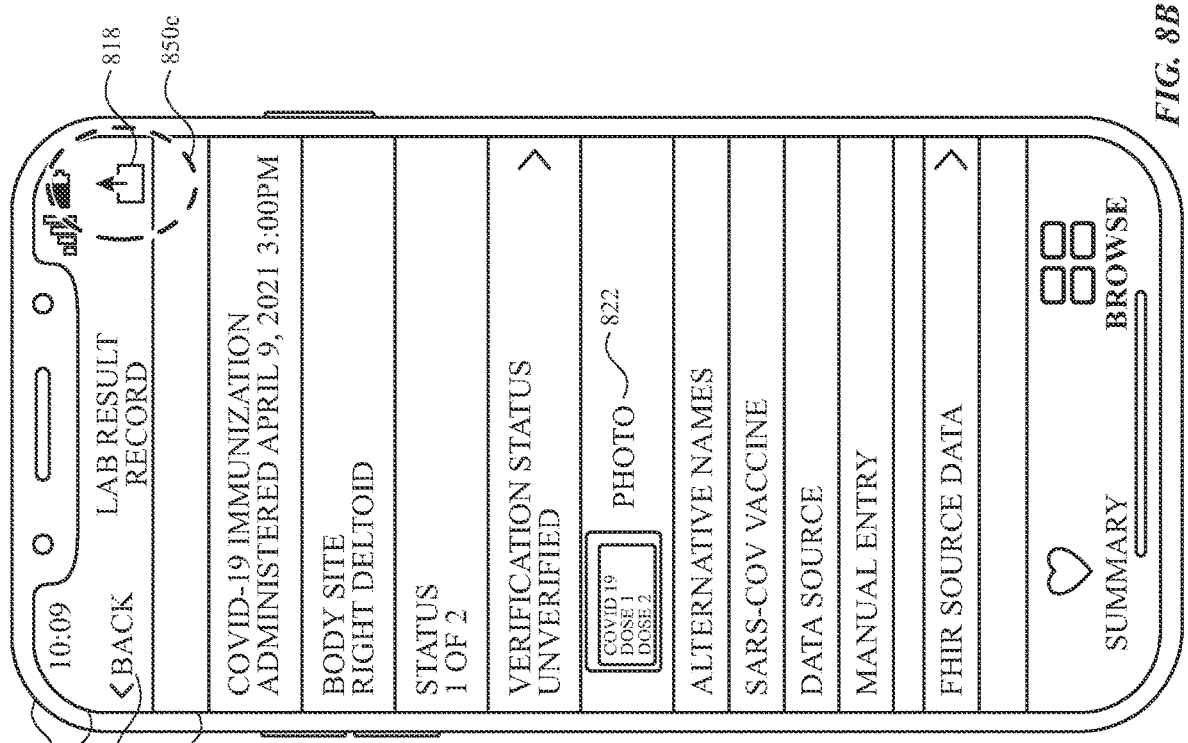
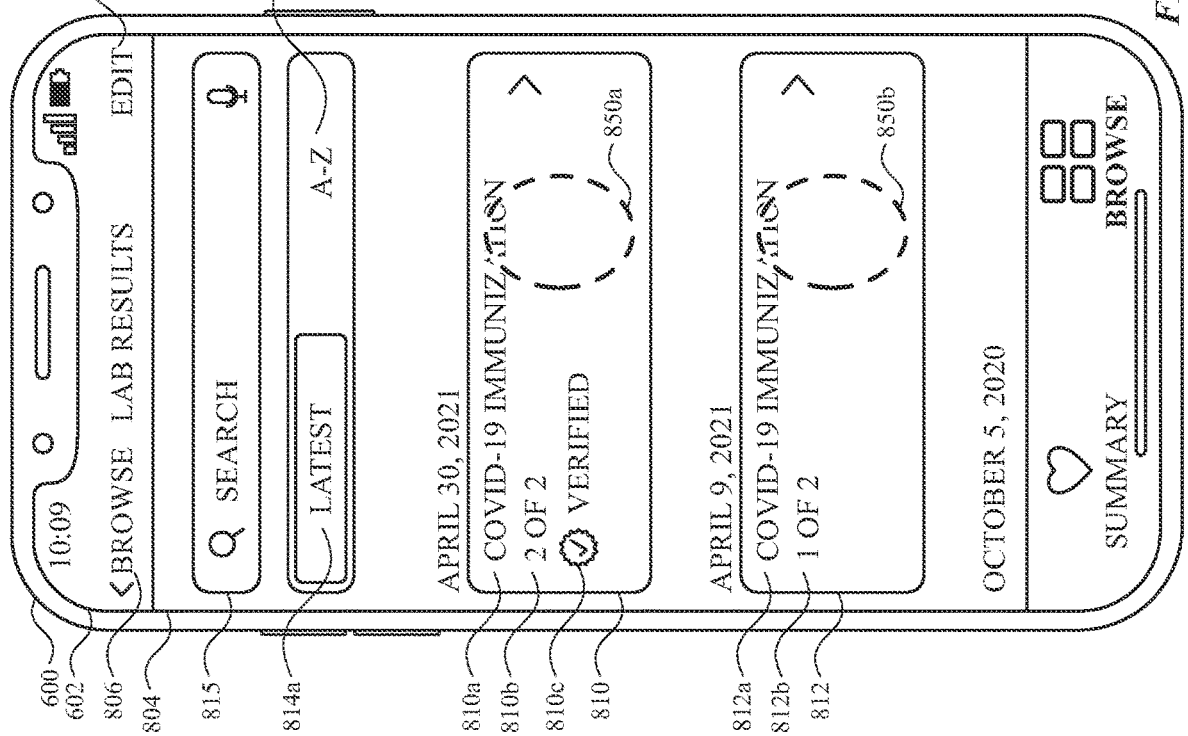

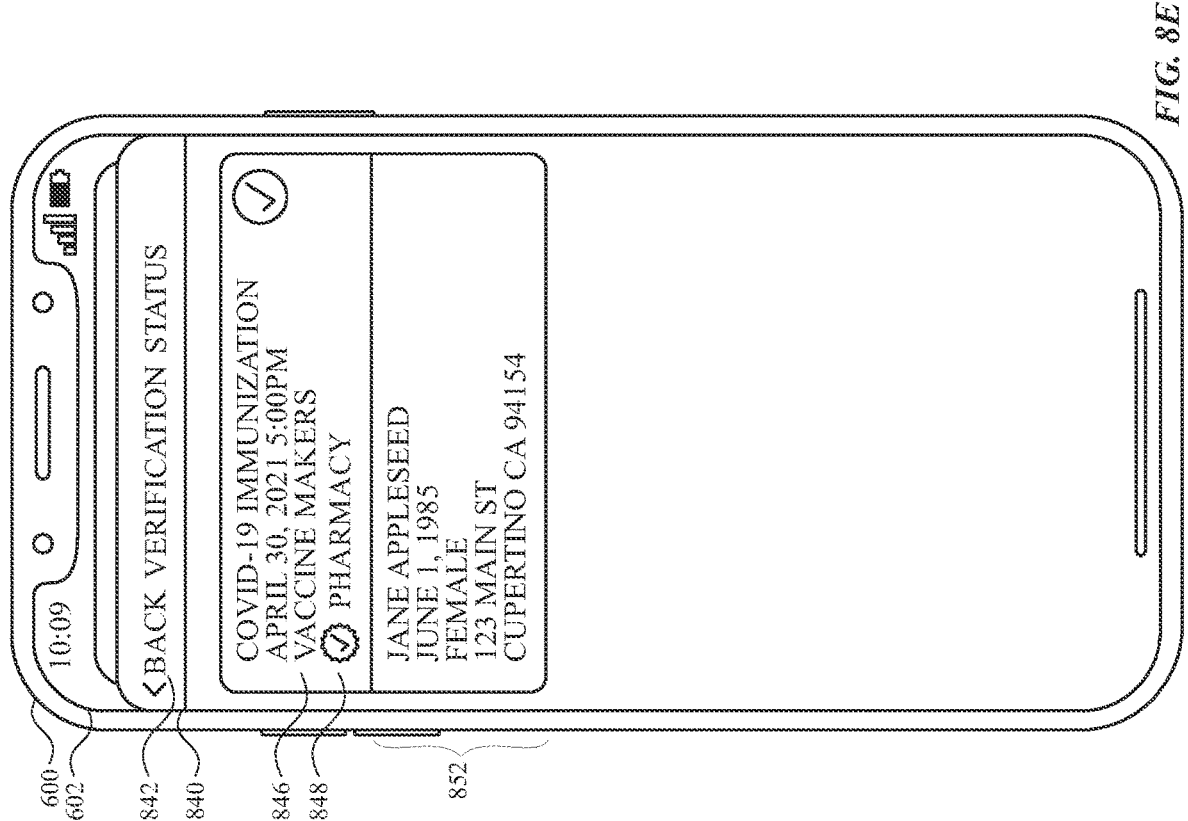

900

902
Displaying, via the display generation component, a clinical record user interface that includes a first set of information corresponding to a first clinical record, wherein displaying the clinical record user interface includes:

904
In accordance with a determination that the first clinical record is a signed clinical record, displaying, via the display generation component, a verification information user-interactive graphical user interface object.

906
In accordance with a determination that the first clinical record is an unsigned clinical record, foregoing displaying the verification information user-interactive graphical user interface object.

908
Receiving, via the one or more input devices, a user input that corresponds to selection of the verification information user-interactive graphical user interface object.

910
In response to receiving the user input that corresponds to selection of the verification information user-interactive graphical user interface object, displaying a verification user interface, wherein the verification user interface includes physiological information corresponding to the first clinical record that was not included in the clinical record user interface.

*FIG. 9*

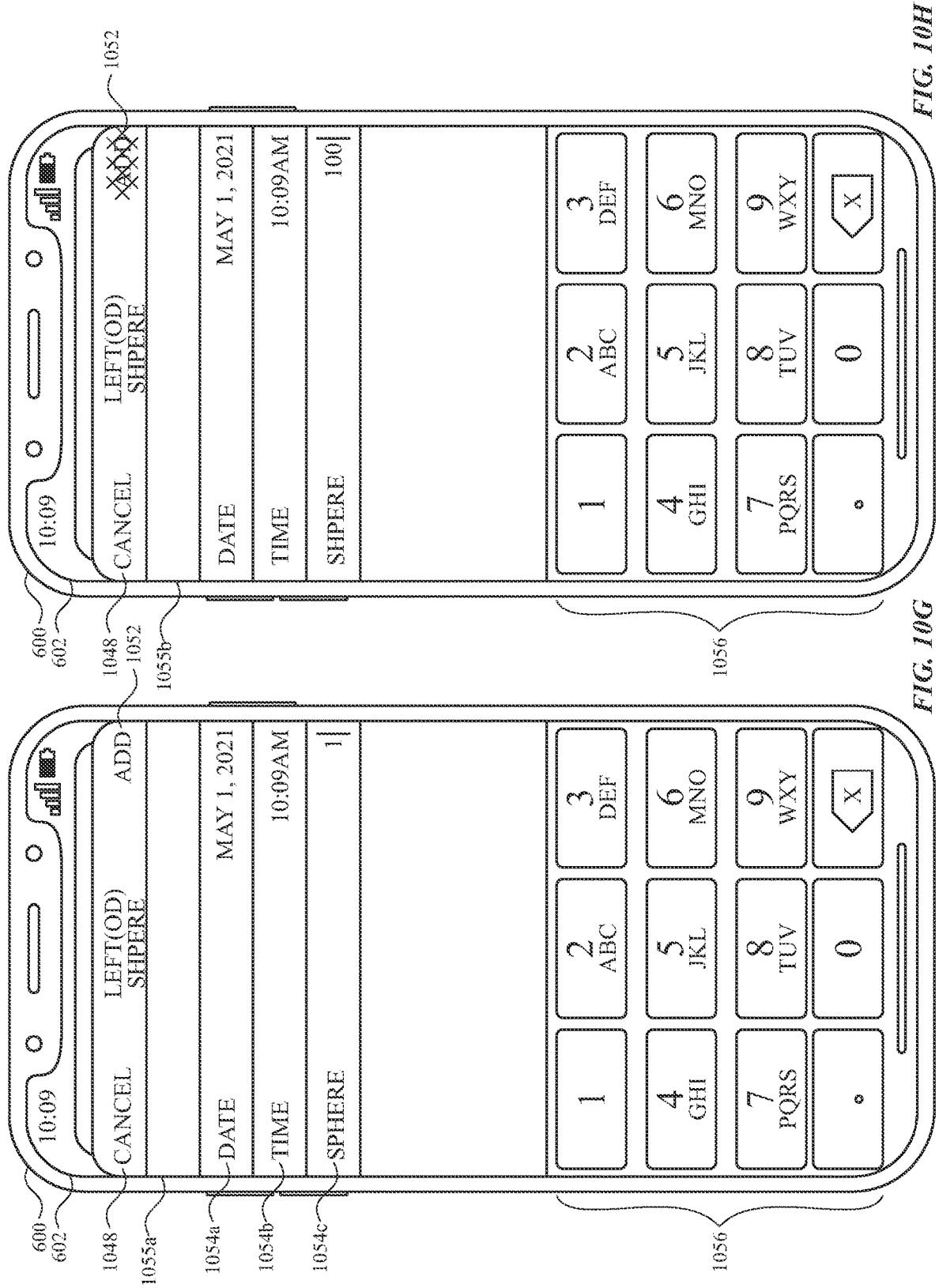

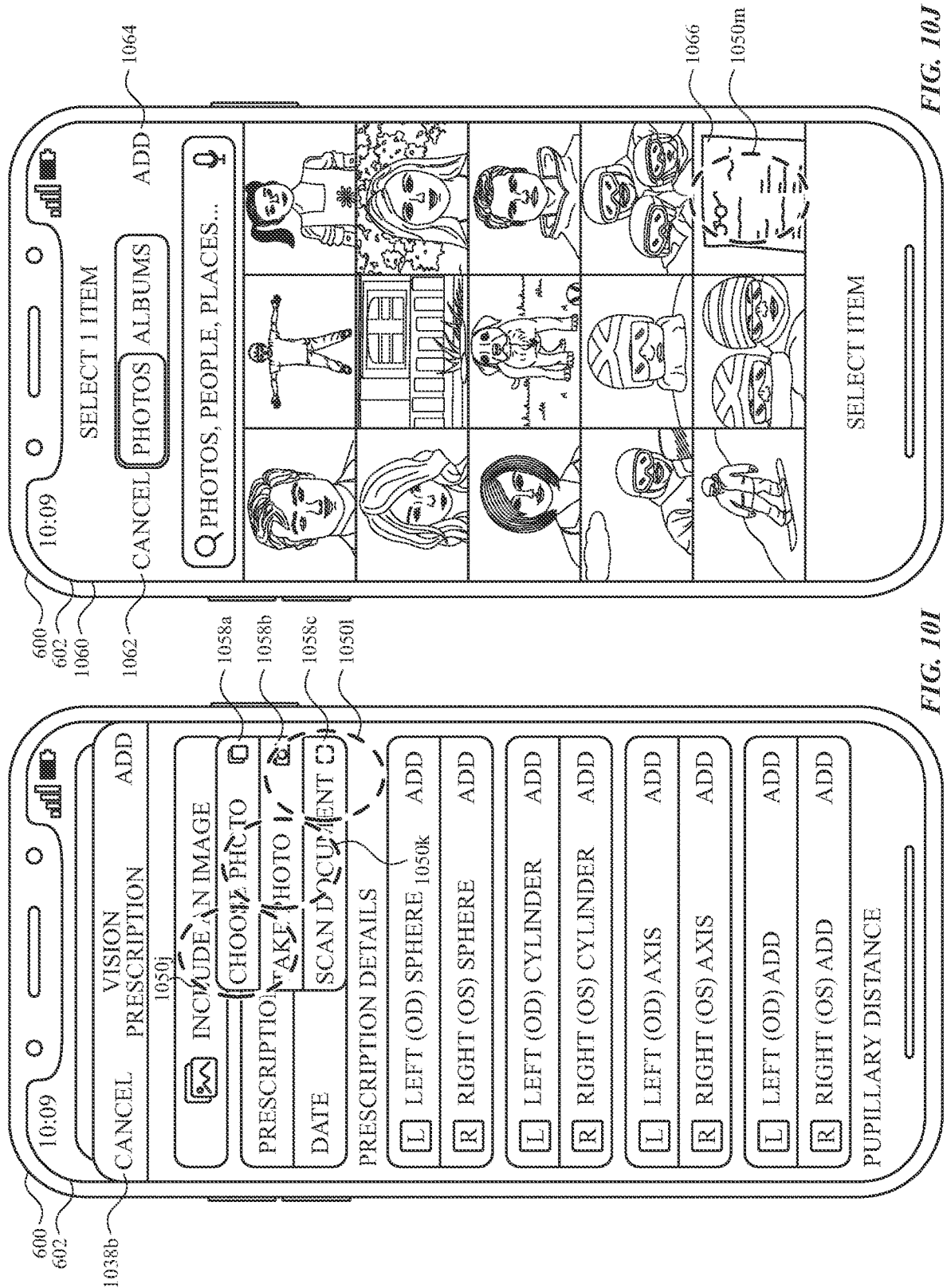

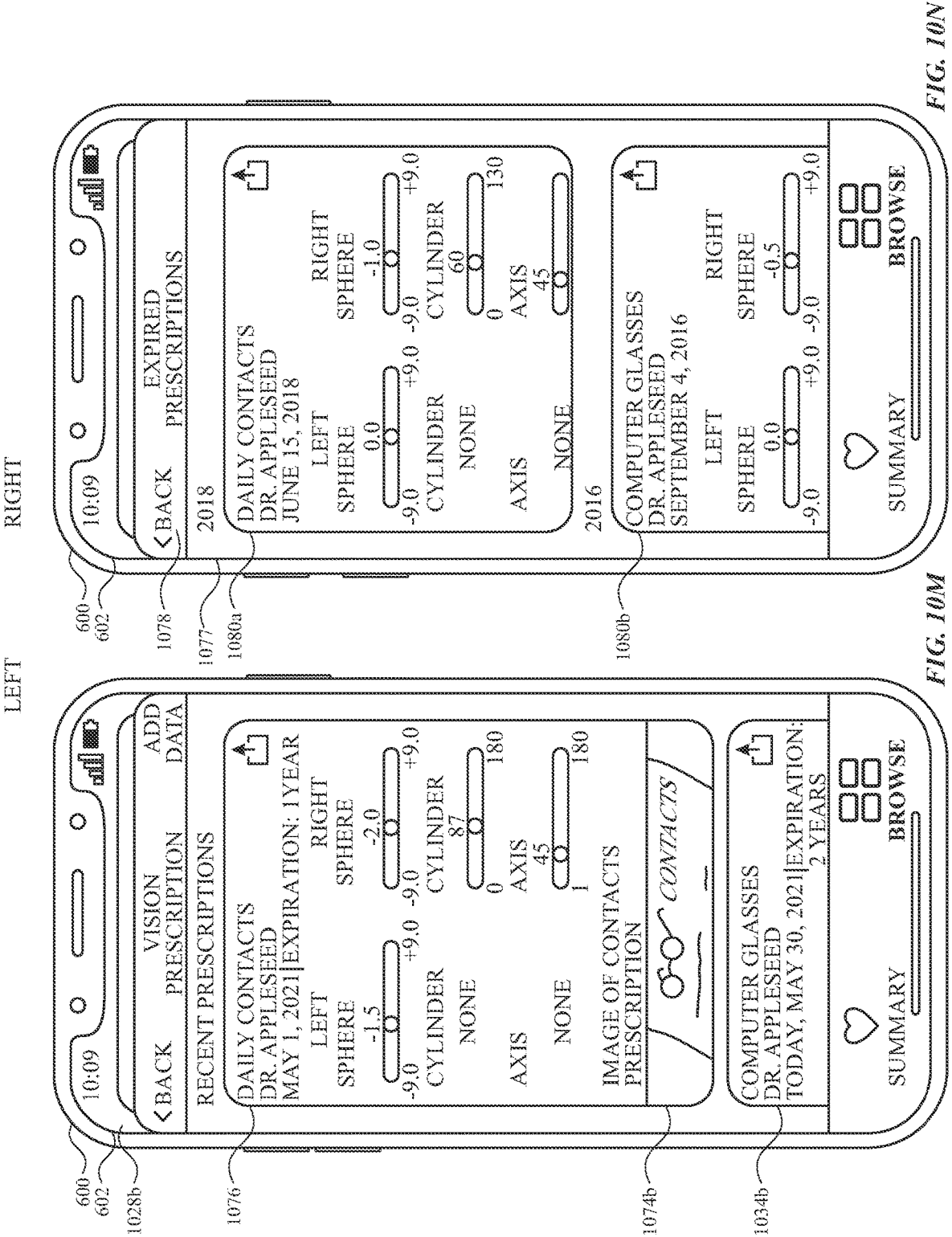

1100

1102
Displaying, via the display generation component, an active prescriptions user interface, wherein the active prescriptions user interface includes:

1104
First information corresponding to one or more prescriptions that satisfy a set of active prescription criteria.

1106
An expired prescriptions user-interactive graphical user interface object.

1108
Receiving, via the one or more input devices, a user input that corresponds to selection of the expired prescriptions user-interactive graphical user interface object.

1110
In response to receiving the user input that corresponds to selection of the expired prescriptions user-interactive graphical user interface object, displaying an expired prescriptions user interface, wherein the expired prescriptions user interface includes second information corresponding to one or more prescriptions that do not satisfy the set of active prescription criteria.

*FIG. 11*

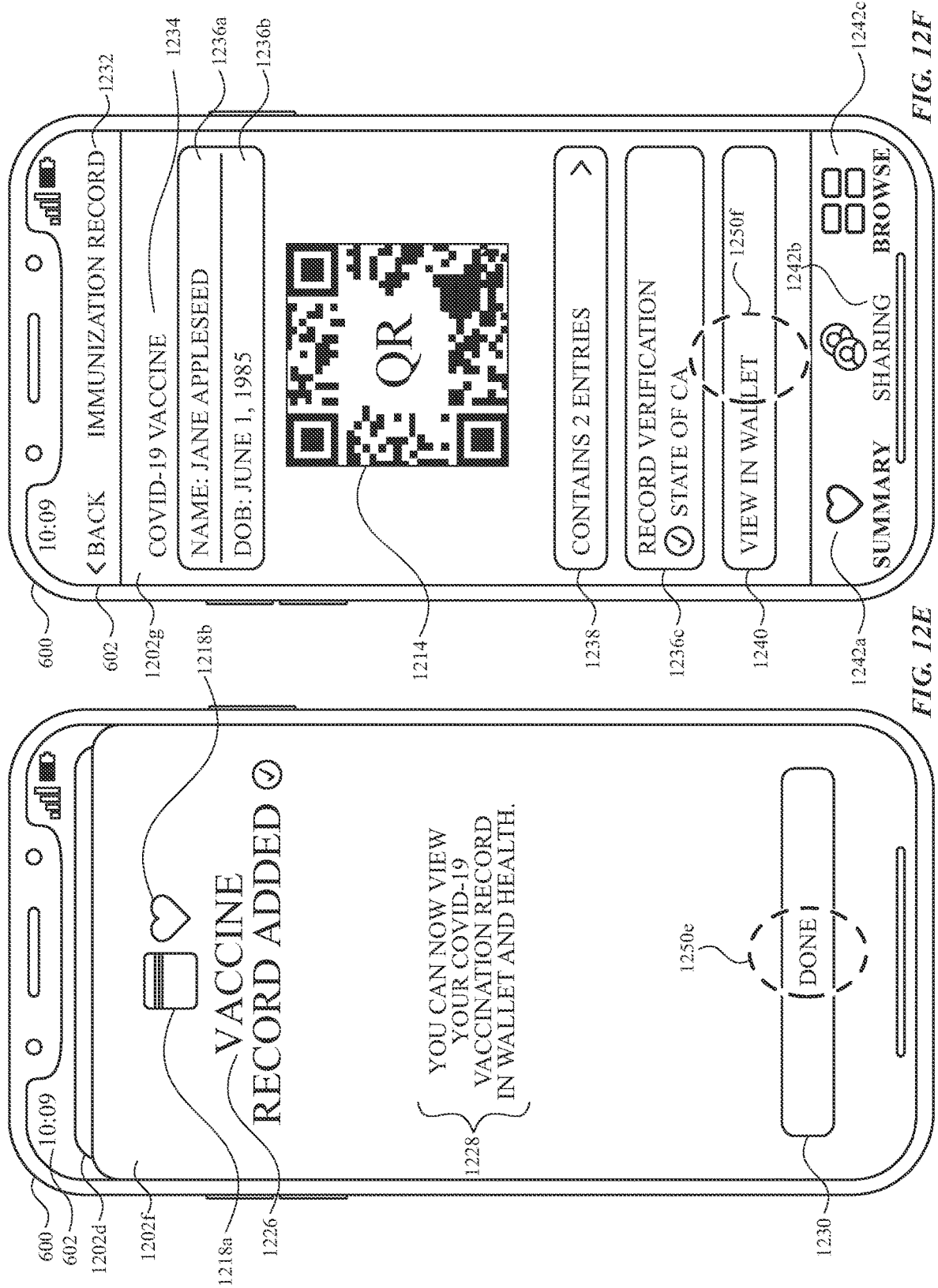

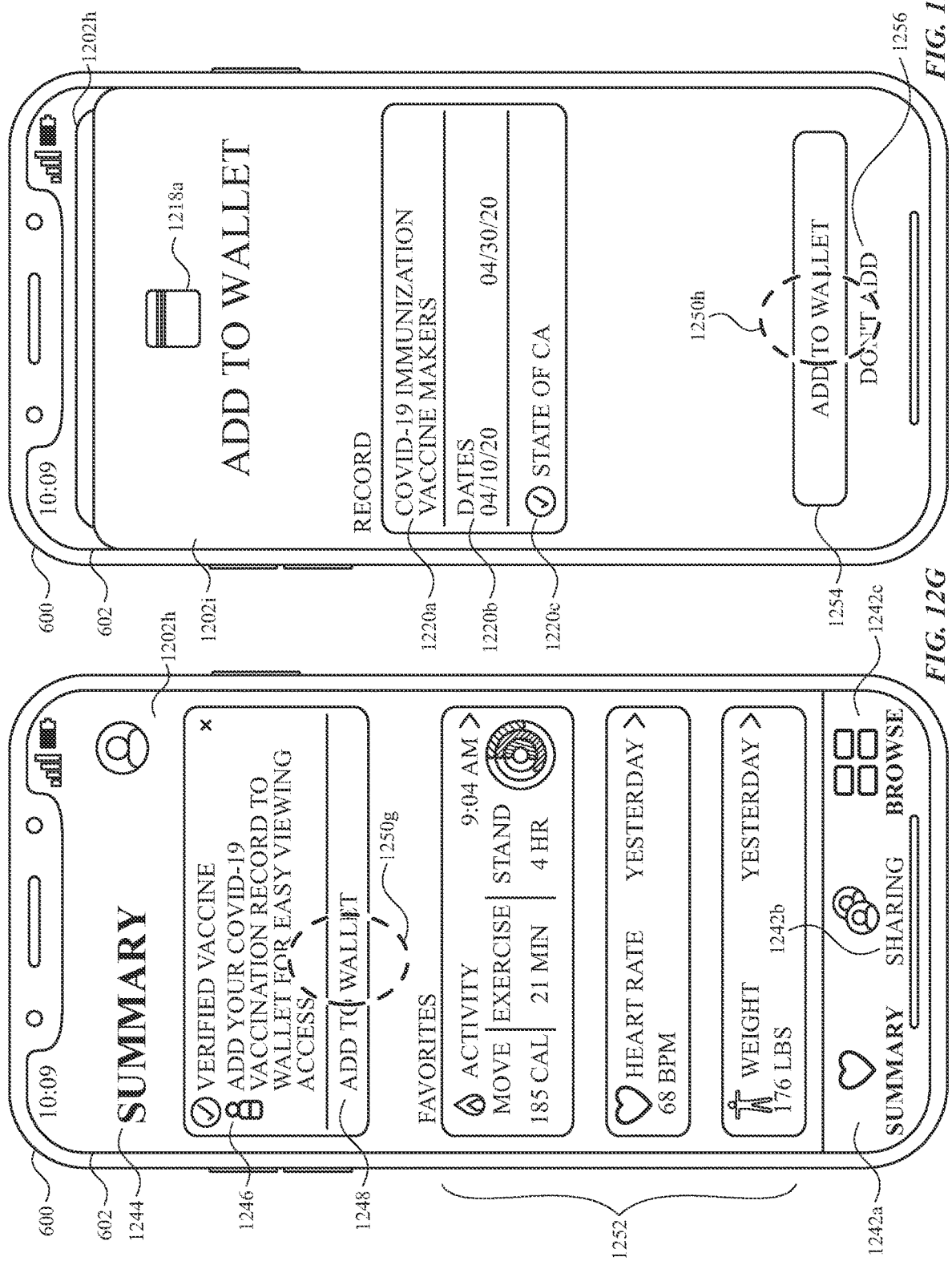

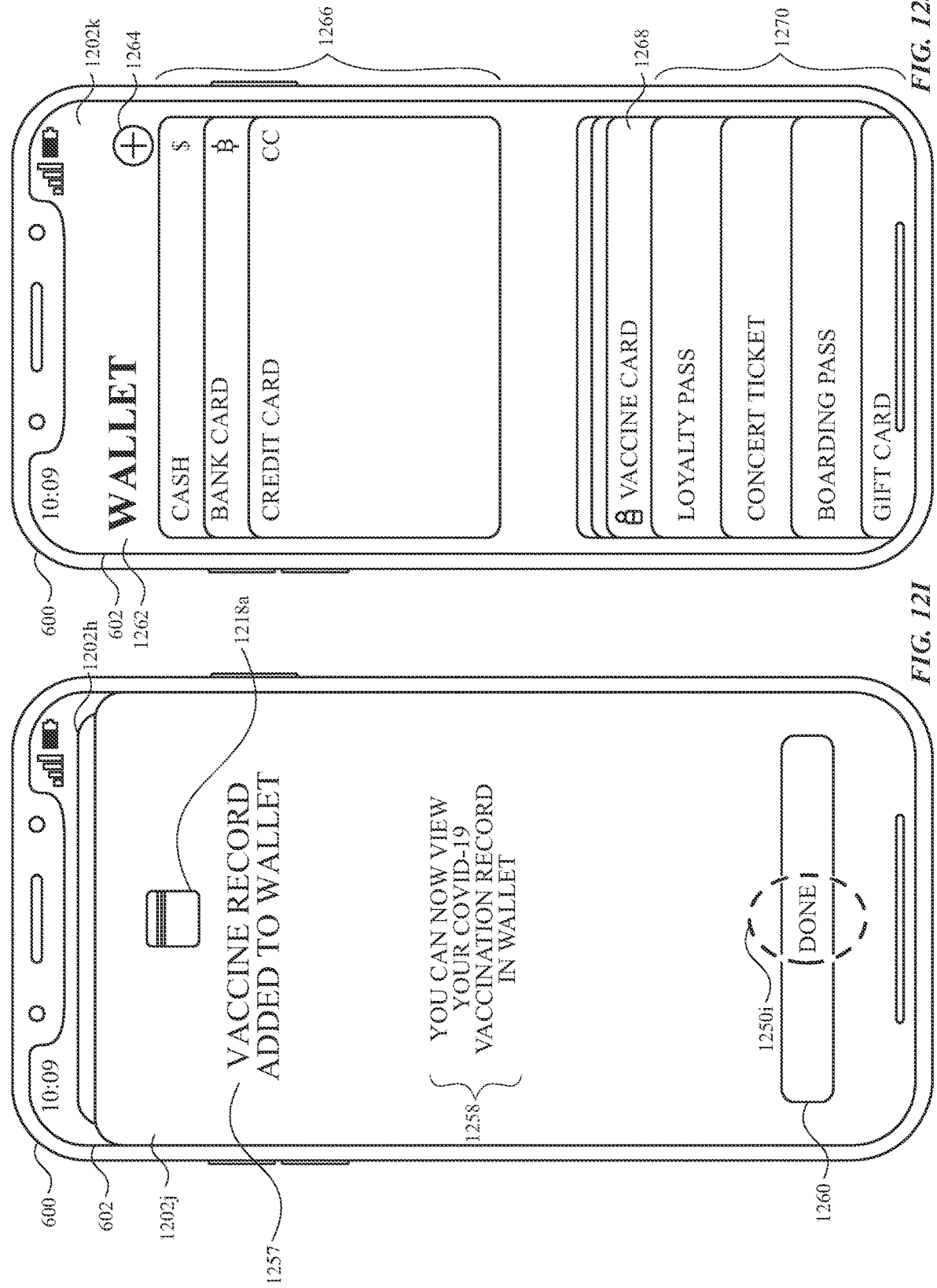

1300

1302
Displaying, via the display generation component, a clinical record user interface, wherein displaying the clinical record user interface includes concurrently displaying:

1304
A set of information corresponding to a clinical record.

1306
A user-interactive graphical user interface object that, when selected, initiates a process for adding data corresponding to at least a portion of the set of information corresponding to the clinical record to both a health application and a wallet application different from the health application.

1308
While displaying the clinical record user interface, receiving, via the one or more input devices, a user input that corresponds to selection of the user-interactive graphical user interface object.

1310
In response to receiving the user input that corresponds to selection of the user-interactive graphical user interface object, initiating the process for adding data corresponding to at least the portion of the set of information corresponding to the clinical record to the health application and the wallet application.

*FIG. 13*

USER INTERFACES RELATED TO SIGNED CLINICAL DATA

CROSS REFERENCE TO RELATED APPLICATIONS

This application claims priority to: U.S. Provisional Patent Application No. 63/197,458, entitled "USER INTERFACES RELATED TO SIGNED CLINICAL DATA," filed Jun. 6, 2021; and U.S. Provisional Patent Application No. 63/243,664, entitled "USER INTERFACES RELATED TO SIGNED CLINICAL DATA," filed Sep. 13, 2021, the contents of each of which are hereby incorporated by reference in their entirety.

FIELD

The present disclosure relates generally to computer user interfaces, and more specifically to techniques for displaying and managing user interfaces for interacting with clinical data.

BACKGROUND

Personal electronic devices allow users to display and manage user interfaces for interacting with clinical data.

BRIEF SUMMARY

Some techniques for displaying and managing user interfaces for interacting with clinical data using electronic devices, however, are generally cumbersome and inefficient. For example, some electronic devices use inefficient or unintuitive methods for adding signed clinical data to an electronic device, or fail to provide visual indications of differences between unsigned clinical data and signed clinical data. For another example, some existing techniques use a complex and time-consuming user interface, which may include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for displaying and managing user interfaces for interacting with clinical data. Such methods and interfaces optionally complement or replace other methods for displaying and managing user interfaces for interacting with clinical data. Such methods and interfaces reduce the cognitive burden on a user and produce a more efficient human-machine interface. For battery-operated computing devices, such methods and interfaces conserve power and increase the time between battery charges.

In accordance with some embodiments, a method performed at a computer system that is in communication with a display generation component and one or more input devices is described. The method comprises: receiving, via the one or more input devices, a request for a clinical record that satisfies a first set of criteria; and in response to receiving the request for a clinical record that satisfies the first set of criteria: in accordance with a determination that the computer system has access to one or more clinical records that satisfy the first set of criteria, displaying, via the display generation component a sharing user interface, wherein the sharing user interface includes a user-interactive graphical user interface object that, when selected, initiates a process for sharing a first clinical record of the one or more clinical records with one or more external electronic devices; and in accordance with a determination that the computer system does not have access to one or more clinical records that satisfy the first set of criteria, forego displaying the sharing user interface.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: receiving, via the one or more input devices, a request for a clinical record that satisfies a first set of criteria; and in response to receiving the request for a clinical record that satisfies the first set of criteria: in accordance with a determination that the computer system has access to one or more clinical records that satisfy the first set of criteria, displaying, via the display generation component a sharing user interface, wherein the sharing user interface includes a user-interactive graphical user interface object that, when selected, initiates a process for sharing a first clinical record of the one or more clinical records with one or more external electronic devices; and in accordance with a determination that the computer system does not have access to one or more clinical records that satisfy the first set of criteria, forego displaying the sharing user interface.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: receiving, via the one or more input devices, a request for a clinical record that satisfies a first set of criteria; and in response to receiving the request for a clinical record that satisfies the first set of criteria: in accordance with a determination that the computer system has access to one or more clinical records that satisfy the first set of criteria, displaying, via the display generation component a sharing user interface, wherein the sharing user interface includes a user-interactive graphical user interface object that, when selected, initiates a process for sharing a first clinical record of the one or more clinical records with one or more external electronic devices; and in accordance with a determination that the computer system does not have access to one or more clinical records that satisfy the first set of criteria, forego displaying the sharing user interface.

In accordance with some embodiments, a computer system that is configured to communicate with a display generation component and one or more input devices is described. The computer system comprises: one or more processors; and memory storing one or more programs configured to be executed by the one or more processors, the one or more programs including instructions for: receiving, via the one or more input devices, a request for a clinical record that satisfies a first set of criteria; and in response to receiving the request for a clinical record that satisfies the first set of criteria: in accordance with a determination that the computer system has access to one or more clinical records that satisfy the first set of criteria, displaying, via the display generation component a sharing user interface, wherein the sharing user interface includes a user-interactive graphical user interface object that, when selected, initiates a process for sharing a first clinical record of the one or more clinical records with one or more external electronic devices; and in accordance with a determination that the computer system does not have access to one or more clinical records that satisfy the first set of criteria, forego displaying the sharing user interface.

In accordance with some embodiments, a computer system that is configured to communicate with a display generation component and one or more input devices is described. The computer system comprises: means for receiving, via the one or more input devices, a request for a clinical record that satisfies a first set of criteria; and means for, in response to receiving the request for a clinical record that satisfies the first set of criteria: in accordance with a determination that the computer system has access to one or more clinical records that satisfy the first set of criteria, displaying, via the display generation component a sharing user interface, wherein the sharing user interface includes a user-interactive graphical user interface object that, when selected, initiates a process for sharing a first clinical record of the one or more clinical records with one or more external electronic devices; and in accordance with a determination that the computer system does not have access to one or more clinical records that satisfy the first set of criteria, forego displaying the sharing user interface.

In accordance with some embodiments, a computer program product is described. The computer program product comprises one or more programs configured to be executed by one or more processors of a computer system that is in communication with a display generation component and one or more input devices. The one or more programs include instructions for: receiving, via the one or more input devices, a request for a clinical record that satisfies a first set of criteria; and in response to receiving the request for a clinical record that satisfies the first set of criteria: in accordance with a determination that the computer system has access to one or more clinical records that satisfy the first set of criteria, displaying, via the display generation component a sharing user interface, wherein the sharing user interface includes a user-interactive graphical user interface object that, when selected, initiates a process for sharing a first clinical record of the one or more clinical records with one or more external electronic devices; and in accordance with a determination that the computer system does not have access to one or more clinical records that satisfy the first set of criteria, forego displaying the sharing user interface.

In accordance with some embodiments, a method performed at a computer system that is in communication with a display generation component and one or more input devices is described. The method comprises: displaying, via the display generation component, a clinical record user interface that includes a first set of information corresponding to a first clinical record, wherein displaying the clinical record user interface includes: in accordance with a determination that the first clinical record is a signed clinical record, displaying, via the display generation component, a verification information user-interactive graphical user interface object; and in accordance with a determination that the first clinical record is an unsigned clinical record, foregoing displaying the verification information user-interactive graphical user interface object; and receiving, via the one or more input devices, a user input that corresponds to selection of the verification information user-interactive graphical user interface object; and in response to receiving the user input that corresponds to selection of the verification information user-interactive graphical user interface object, displaying a verification user interface, wherein the verification user interface includes physiological information corresponding to the first clinical record that was not included in the clinical record user interface.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: displaying, via the display generation component, a clinical record user interface that includes a first set of information corresponding to a first clinical record, wherein displaying the clinical record user interface includes: in accordance with a determination that the first clinical record is a signed clinical record, displaying, via the display generation component, a verification information user-interactive graphical user interface object; and in accordance with a determination that the first clinical record is an unsigned clinical record, foregoing displaying the verification information user-interactive graphical user interface object; and receiving, via the one or more input devices, a user input that corresponds to selection of the verification information user-interactive graphical user interface object; and in response to receiving the user input that corresponds to selection of the verification information user-interactive graphical user interface object, displaying a verification user interface, wherein the verification user interface includes physiological information corresponding to the first clinical record that was not included in the clinical record user interface.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: displaying, via the display generation component, a clinical record user interface that includes a first set of information corresponding to a first clinical record, wherein displaying the clinical record user interface includes: in accordance with a determination that the first clinical record is a signed clinical record, displaying, via the display generation component, a verification information user-interactive graphical user interface object; and in accordance with a determination that the first clinical record is an unsigned clinical record, foregoing displaying the verification information user-interactive graphical user interface object; and receiving, via the one or more input devices, a user input that corresponds to selection of the verification information user-interactive graphical user interface object; and in response to receiving the user input that corresponds to selection of the verification information user-interactive graphical user interface object, displaying a verification user interface, wherein the verification user interface includes physiological information corresponding to the first clinical record that was not included in the clinical record user interface.

In accordance with some embodiments, a computer system that is configured to communicate with a display generation component and one or more input devices is described. The computer system comprises: one or more processors; and memory storing one or more programs configured to be executed by the one or more processors, the one or more programs including instructions for: displaying, via the display generation component, a clinical record user interface that includes a first set of information corresponding to a first clinical record, wherein displaying the clinical record user interface includes: in accordance with a determination that the first clinical record is a signed clinical record, displaying, via the display generation component, a verification information user-interactive graphical user interface object; and in accordance with a determination that the first clinical record is an unsigned clinical record, foregoing displaying the verification information user-interactive graphical user interface object; and receiving, via the one or more input devices, a user input that corresponds to selection of the verification information user-interactive graphical user interface object; and in response to receiving the user input that corresponds to selection of the verification information user-interactive graphical user interface object, displaying a verification user interface, wherein the verification user interface includes physiological information corresponding to the first clinical record that was not included in the clinical record user interface.

In accordance with some embodiments, a computer system that is configured to communicate with a display generation component and one or more input devices is described. The computer system comprises: means for displaying, via the display generation component, a clinical record user interface that includes a first set of information corresponding to a first clinical record, wherein displaying the clinical record user interface includes: in accordance with a determination that the first clinical record is a signed clinical record, displaying, via the display generation component, a verification information user-interactive graphical user interface object; and in accordance with a determination that the first clinical record is an unsigned clinical record, foregoing displaying the verification information user-interactive graphical user interface object; and means for receiving, via the one or more input devices, a user input that corresponds to selection of the verification information user-interactive graphical user interface object; and means for, in response to receiving the user input that corresponds to selection of the verification information user-interactive graphical user interface object, displaying a verification user interface, wherein the verification user interface includes physiological information corresponding to the first clinical record that was not included in the clinical record user interface.

In accordance with some embodiments, a computer program product is described. The computer program product comprises one or more programs configured to be executed by one or more processors of a computer system that is in communication with a display generation component and one or more input devices. The one or more programs include instructions for: displaying, via the display generation component, a clinical record user interface that includes a first set of information corresponding to a first clinical record, wherein displaying the clinical record user interface includes: in accordance with a determination that the first clinical record is a signed clinical record, displaying, via the display generation component, a verification information user-interactive graphical user interface object; and in accordance with a determination that the first clinical record is an unsigned clinical record, foregoing displaying the verification information user-interactive graphical user interface object; and receiving, via the one or more input devices, a user input that corresponds to selection of the verification information user-interactive graphical user interface object; and in response to receiving the user input that corresponds to selection of the verification information user-interactive graphical user interface object, displaying a verification user interface, wherein the verification user interface includes physiological information corresponding to the first clinical record that was not included in the clinical record user interface.

In accordance with some embodiments, a method performed at a computer system that is in communication with a display generation component and one or more input devices is described. The method comprises: displaying, via the display generation component, an active prescriptions user interface, wherein the active prescriptions user interface includes: first information corresponding to one or more prescriptions that satisfy a set of active prescription criteria; and an expired prescriptions user-interactive graphical user interface object; and receiving, via the one or more input devices, a user input that corresponds to selection of the expired prescriptions user-interactive graphical user interface object; and in response to receiving the user input that corresponds to selection of the expired prescriptions user-interactive graphical user interface object, displaying an expired prescriptions user interface, wherein the expired prescriptions user interface includes second information corresponding to one or more prescriptions that do not satisfy the set of active prescription criteria.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: displaying, via the display generation component, an active prescriptions user interface, wherein the active prescriptions user interface includes: first information corresponding to one or more prescriptions that satisfy a set of active prescription criteria; and an expired prescriptions user-interactive graphical user interface object; and receiving, via the one or more input devices, a user input that corresponds to selection of the expired prescriptions user-interactive graphical user interface object; and in response to receiving the user input that corresponds to selection of the expired prescriptions user-interactive graphical user interface object, displaying an expired prescriptions user interface, wherein the expired prescriptions user interface includes second information corresponding to one or more prescriptions that do not satisfy the set of active prescription criteria.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: displaying, via the display generation component, an active prescriptions user interface, wherein the active prescriptions user interface includes: first information corresponding to one or more prescriptions that satisfy a set of active prescription criteria; and an expired prescriptions user-interactive graphical user interface object; and receiving, via the one or more input devices, a user input that corresponds to selection of the expired prescriptions user-interactive graphical user interface object; and in response to receiving the user input that corresponds to selection of the expired prescriptions user-interactive graphical user interface object, displaying an expired prescriptions user interface, wherein the expired prescriptions user interface includes second information corresponding to one or more prescriptions that do not satisfy the set of active prescription criteria.

In accordance with some embodiments, a computer system that is configured to communicate with a display generation component and one or more input devices is described. The computer system comprises: one or more processors; and memory storing one or more programs configured to be executed by the one or more processors, the one or more programs including instructions for: displaying, via the display generation component, an active prescriptions user interface, wherein the active prescriptions user interface includes: first information corresponding to one or more prescriptions that satisfy a set of active prescription criteria; and an expired prescriptions user-interactive graphical user interface object; and receiving, via the one or more input devices, a user input that corresponds to selection of the expired prescriptions user-interactive graphical user interface object; and in response to receiving the user input that corresponds to selection of the expired prescriptions user-interactive graphical user interface object, displaying an expired prescriptions user interface, wherein the expired prescriptions user interface includes second information corresponding to one or more prescriptions that do not satisfy the set of active prescription criteria.

In accordance with some embodiments, a computer system that is configured to communicate with a display generation component and one or more input devices is described. The computer system comprises: means for displaying, via the display generation component, an active prescriptions user interface, wherein the active prescriptions user interface includes: first information corresponding to one or more prescriptions that satisfy a set of active prescription criteria; and an expired prescriptions user-interactive graphical user interface object; and means for receiving, via the one or more input devices, a user input that corresponds to selection of the expired prescriptions user-interactive graphical user interface object; and means for, in response to receiving the user input that corresponds to selection of the expired prescriptions user-interactive graphical user interface object, displaying an expired prescriptions user interface, wherein the expired prescriptions user interface includes second information corresponding to one or more prescriptions that do not satisfy the set of active prescription criteria.

In accordance with some embodiments, a computer program product is described. The computer program product comprises one or more programs configured to be executed by one or more processors of a computer system that is in communication with a display generation component and one or more input devices. The one or more programs include instructions for: displaying, via the display generation component, an active prescriptions user interface, wherein the active prescriptions user interface includes: first information corresponding to one or more prescriptions that satisfy a set of active prescription criteria; and an expired prescriptions user-interactive graphical user interface object; and receiving, via the one or more input devices, a user input that corresponds to selection of the expired prescriptions user-interactive graphical user interface object; and in response to receiving the user input that corresponds to selection of the expired prescriptions user-interactive graphical user interface object, displaying an expired prescriptions user interface, wherein the expired prescriptions user interface includes second information corresponding to one or more prescriptions that do not satisfy the set of active prescription criteria.

In accordance with some embodiments, a method performed at a computer system that is in communication with a display generation component and one or more input devices is described. The method comprises: displaying, via the display generation component, a clinical record user interface, wherein displaying the clinical record user interface includes concurrently displaying: a set of information corresponding to a clinical record; and a user-interactive graphical user interface object that, when selected, initiates a process for adding data corresponding to at least a portion of the set of information corresponding to the clinical record to both a health application and a wallet application different from the health application; and while displaying the clinical record user interface, receiving, via the one or more input devices, a user input that corresponds to selection of the user-interactive graphical user interface object; and in response to receiving the user input that corresponds to selection of the user-interactive graphical user interface object, initiating the process for adding data corresponding to at least the portion of the set of information corresponding to the clinical record to the health application and the wallet application.

In accordance with some embodiments, a non-transitory computer-readable storage medium storing one or more programs configured to be executed by one or more processors of a computer system that is in communication with a display generation component and one or more input devices is described. The one or more programs include instructions for: displaying, via the display generation component, a clinical record user interface, wherein displaying the clinical record user interface includes concurrently displaying: a set of information corresponding to a clinical record; and a user-interactive graphical user interface object that, when selected, initiates a process for adding data corresponding to at least a portion of the set of information corresponding to the clinical record to both a health application and a wallet application different from the health application; and while displaying the clinical record user interface, receiving, via the one or more input devices, a user input that corresponds to selection of the user-interactive graphical user interface object; and in response to receiving the user input that corresponds to selection of the user-interactive graphical user interface object, initiating the process for adding data corresponding to at least the portion of the set of information corresponding to the clinical record to the health application and the wallet application.

In accordance with some embodiments, a transitory computer-readable storage medium storing one or more programs configured to be executed by one or more processors of a computer system that is in communication with a display generation component and one or more input devices is described. The one or more programs include instructions for: displaying, via the display generation component, a clinical record user interface, wherein displaying the clinical record user interface includes concurrently displaying: a set of information corresponding to a clinical record; and a user-interactive graphical user interface object that, when selected, initiates a process for adding data corresponding to at least a portion of the set of information corresponding to the clinical record to both a health application and a wallet application different from the health application; and while displaying the clinical record user interface, receiving, via the one or more input devices, a user input that corresponds to selection of the user-interactive graphical user interface object; and in response to receiving the user input that corresponds to selection of the user-interactive graphical user interface object, initiating the process for adding data corresponding to at least the portion of the set of information corresponding to the clinical record to the health application and the wallet application.

In accordance with some embodiments, a computer system comprising a display generation component, and one or more input devices, one or more processors, and memory storing one or more programs configured to be executed by the one or more processors is described. The one or more programs including instructions for: displaying, via the display generation component, a clinical record user interface, wherein displaying the clinical record user interface includes concurrently displaying: a set of information corresponding to a clinical record; and a user-interactive graphical user interface object that, when selected, initiates a process for adding data corresponding to at least a portion of the set of information corresponding to the clinical record to both a health application and a wallet application different from the health application; and while displaying the clinical record user interface, receiving, via the one or more input devices, a user input that corresponds to selection of the user-interactive graphical user interface object; and in response to receiving the user input that corresponds to selection of the user-interactive graphical user interface object, initiating the process for adding data corresponding to at least the portion of the set of information corresponding to the clinical record to the health application and the wallet application.

In accordance with some embodiments, a computer system that is configured to communicate with a display generation component and one or more input devices is described. The computer system comprises: means for displaying, via the display generation component, a clinical record user interface, wherein displaying the clinical record user interface includes concurrently displaying: a set of information corresponding to a clinical record; and a user-interactive graphical user interface object that, when selected, initiates a process for adding data corresponding to at least a portion of the set of information corresponding to the clinical record to both a health application and a wallet application different from the health application; and means for, while displaying the clinical record user interface, receiving, via the one or more input devices, a user input that corresponds to selection of the user-interactive graphical user interface object; and means for, in response to receiving the user input that corresponds to selection of the user-interactive graphical user interface object, initiating the process for adding data corresponding to at least the portion of the set of information corresponding to the clinical record to the health application and the wallet application.

In accordance with some embodiments, a computer program product is described. The computer program product comprises one or more programs configured to be executed by one or more processors of a computer system that is in communication with a display generation component and one or more input devices. The one or more programs include instructions for: displaying, via the display generation component, a clinical record user interface, wherein displaying the clinical record user interface includes concurrently displaying: a set of information corresponding to a clinical record; and a user-interactive graphical user interface object that, when selected, initiates a process for adding data corresponding to at least a portion of the set of information corresponding to the clinical record to both a health application and a wallet application different from the health application; and while displaying the clinical record user interface, receiving, via the one or more input devices, a user input that corresponds to selection of the user-interactive graphical user interface object; and in response to receiving the user input that corresponds to selection of the user-interactive graphical user interface object, initiating the process for adding data corresponding to at least the portion of the set of information corresponding to the clinical record to the health application and the wallet application.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for displaying and managing user interfaces for interacting with clinical data, thereby increasing the effectiveness, efficiency, and user satisfaction with such devices. Such methods and interfaces may complement or replace other methods for displaying and managing user interfaces for interacting with clinical data.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 4B illustrates an exemplary user interface for a multifunction device with a touch-sensitive surface that is separate from the display in accordance with some embodiments.

FIGS. 6A-6G illustrate exemplary user interfaces for adding a signed clinical record to a computer system.

FIG. 7 is a flow diagram illustrating a method for displaying user interfaces for adding a signed clinical record to a computer system in accordance with some embodiments.

FIGS. 8A-8E illustrate exemplary user interfaces for displaying signed and unsigned clinical records.

FIG. 9 is a flow diagram illustrating a method for displaying user interfaces for displaying signed and unsigned clinical records in accordance with some embodiments.

FIG. 11 is a flow diagram illustrating a method for displaying user interfaces for adding a vision prescription to a computer system in accordance with some embodiments.

FIGS. 12A-12J illustrate exemplary user interfaces for adding clinical records to applications.

FIG. 13 is a flow diagram illustrating a method for displaying user interfaces for adding clinical records to applications.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for displaying and managing user interfaces for interacting with clinical data. For example, there is a need for devices that enable an intuitive and efficient method for displaying user interfaces for interacting with clinical data that can be easily understood and managed by a user. Such techniques can reduce the cognitive burden on a user who view and manage signed clinical records, thereby enhancing productivity. Further, such techniques can reduce processor and battery power otherwise wasted on redundant user inputs.

Figure 10A:
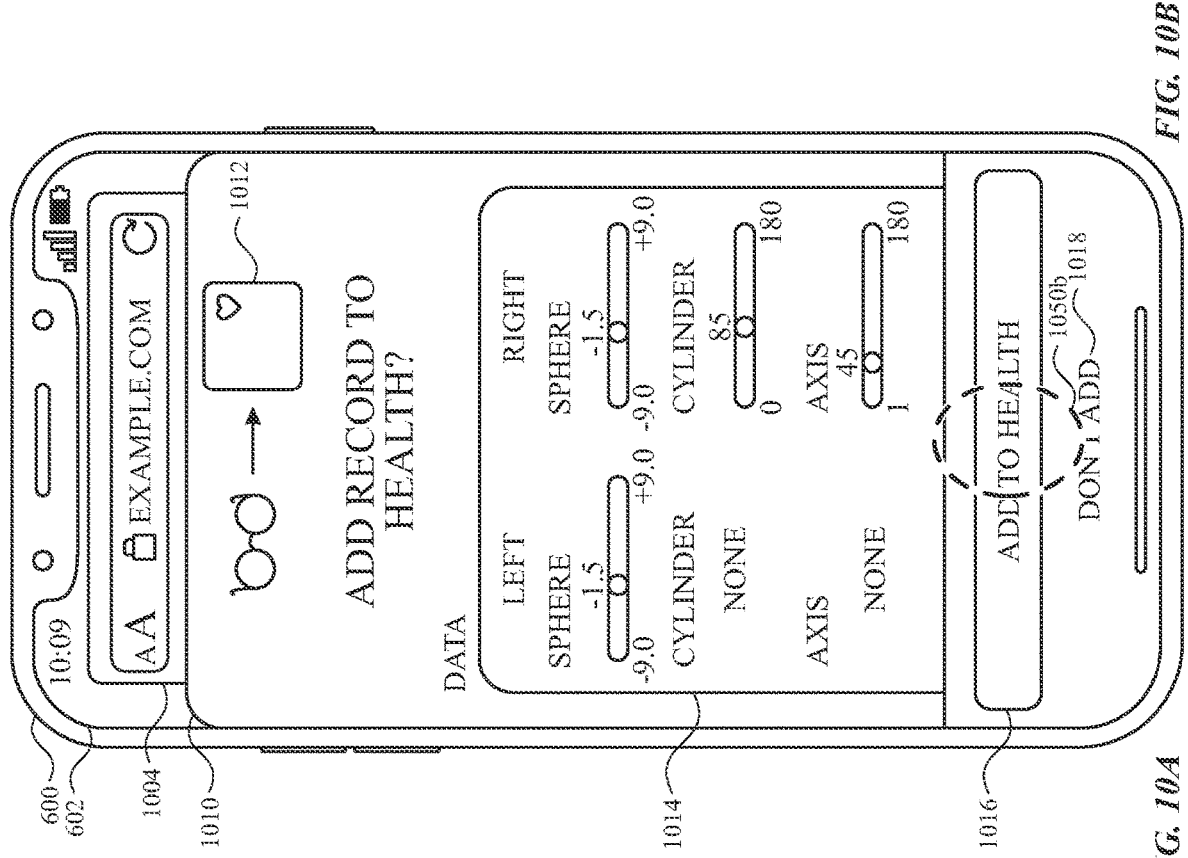
FIGS. 10A-10O illustrate exemplary user interfaces for adding a vision prescription to a computer system.

Below, FIGS. 1A-1B, 2, 3, 4A-4B, and 5A-5B provide a description of exemplary devices for performing the techniques for managing event notifications. FIGS. 6A-6G illustrate exemplary user interfaces for adding a signed clinical record to a computer system. FIG. 7 is a flow diagram illustrating methods for adding a signed clinical record to a computer system in accordance with some embodiments. The user interfaces in FIGS. 6A-6G are used to illustrate the processes described below, including the processes in FIG. 7. FIGS. 8A-8E illustrate exemplary user interfaces for displaying signed and unsigned clinical records. FIG. 9 is a flow diagram illustrating methods of displaying signed and unsigned clinical records in accordance with some embodiments. The user interfaces in FIGS. 8A-8E are used to illustrate the processes described below, including the processes in FIG. 9. FIGS. 10A-10O illustrate exemplary user interfaces for adding a vision prescription to a computer system. FIG. 11 is a flow diagram illustrating methods for adding a vision prescription to a computer system in accordance with some embodiments. The user interfaces in FIGS. 10A-10O are used to illustrate the process described below, including the processes in FIG. 11. FIGS. 12A-12J illustrate exemplary user interfaces for adding clinical records to applications. FIG. 13 is a flow diagram illustrating methods for displaying user interfaces for adding clinical records to applications. The user interfaces in FIGS. 12A-12J are used to illustrate the processes described below, including the processes in FIG. 13.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer readable medium claims where the system or computer readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that, similar to a method with contingent steps, a system or computer readable storage medium can repeat the steps of a method as many times as are needed to ensure that all of the contingent steps have been performed.

The processes described below enhance the operability of the devices and make the user-device interfaces more efficient (e.g., by helping the user to provide proper inputs and reducing user mistakes when operating/interacting with the device) through various techniques, including by providing improved visual feedback to the user, reducing the number of inputs needed to perform an operation, providing additional control options without cluttering the user interface with additional displayed controls, performing an operation when a set of conditions has been met without requiring further user input, and/or additional techniques. These techniques also reduce power usage and improve battery life of the device by enabling the user to use the device more quickly and efficiently.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer readable medium claims where the system or computer readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that, similar to a method with contingent steps, a system or computer readable storage medium can repeat the steps of a method as many times as are needed to ensure that all of the contingent steps have been performed.

Although the following description uses terms "first," "second," etc. to describe various elements, these elements should not be limited by the terms. In some embodiments, these terms are used to distinguish one element from another. For example, a first touch could be termed a second touch, and, similarly, a second touch could be termed a first touch, without departing from the scope of the various described embodiments. In some embodiments, the first touch and the second touch are two separate references to the same touch. In some embodiments, the first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
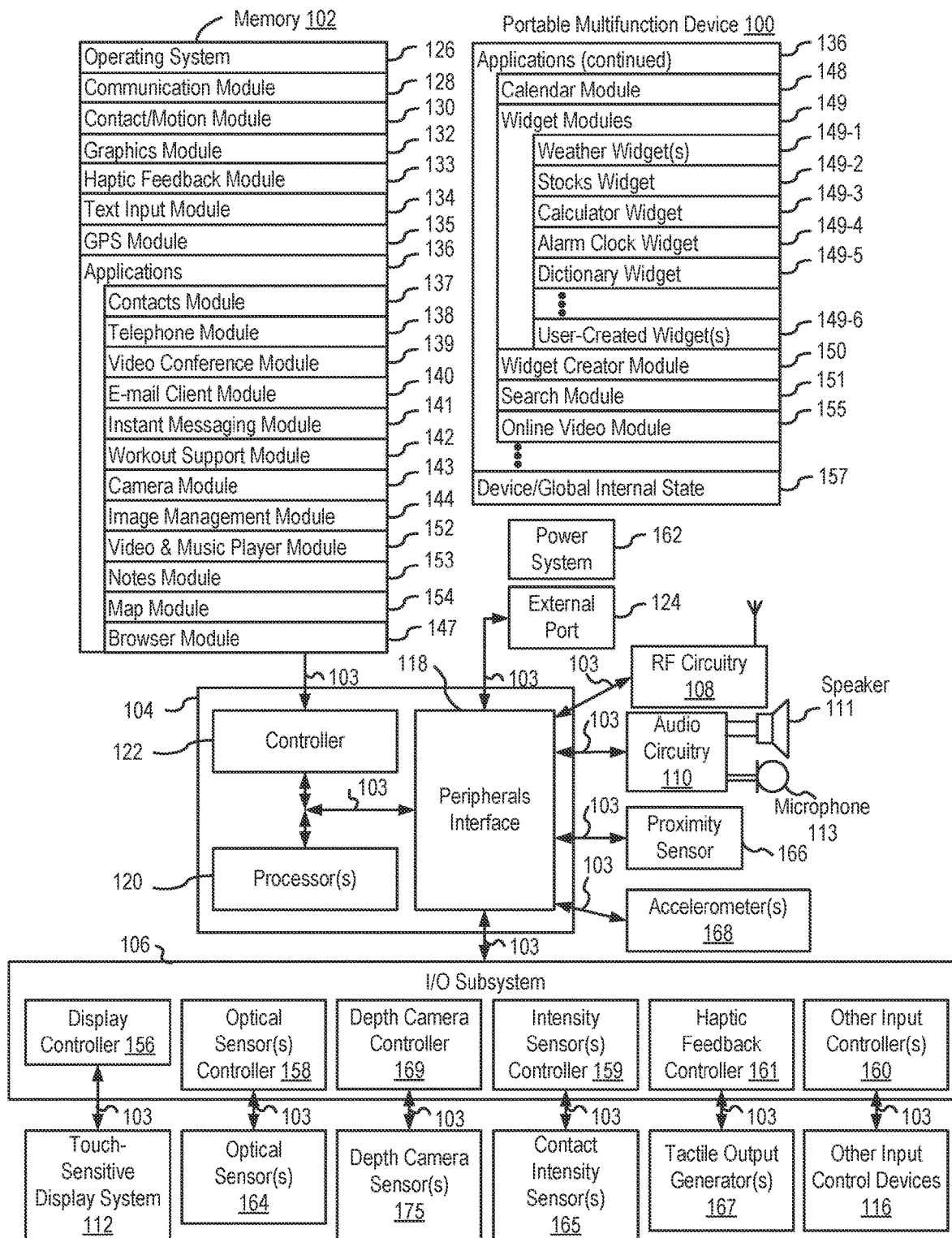
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs (such as computer programs (e.g., including instructions)) and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures and/or air gestures) as input. In some embodiments, the one or more input devices are integrated with the computer system. In some embodiments, the one or more input devices are separate from the computer system. In some embodiments, an air gesture is a gesture that is detected without the user touching an input element that is part of the device (or independently of an input element that is a part of the device) and is based on detected motion of a portion of the user's body through the air including motion of the user's body relative to an absolute reference (e.g., an angle of the user's arm relative to the ground or a distance of the user's hand relative to the ground), relative to another portion of the user's body (e.g., movement of a hand of the user relative to a shoulder of the user, movement of one hand of the user relative to another hand of the user, and/or movement of a finger of the user relative to another finger or portion of a hand of the user), and/or absolute motion of a portion of the user's body (e.g., a tap gesture that includes movement of a hand in a predetermined pose by a predetermined amount and/or speed, or a shake gesture that includes a predetermined speed or amount of rotation of a portion of the user's body).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
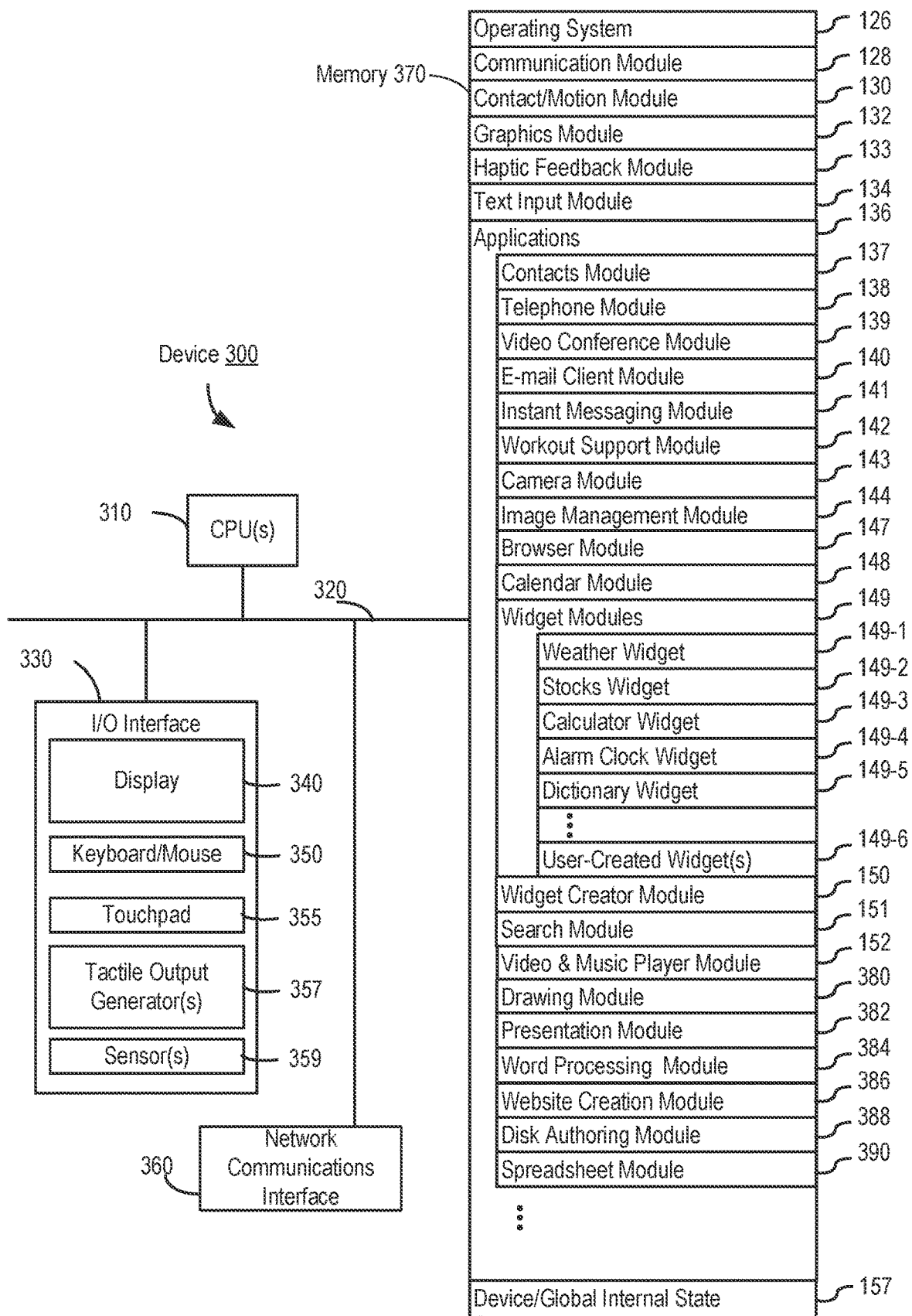
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts module 137, e-mail client module 140, IM module 141, browser module 147, and any other application that needs text input).

GPS module 135 determines the location of the device and provides this information for use in various applications (e.g., to telephone module 138 for use in location-based dialing; to camera module 143 as picture/video metadata; and to applications that provide location-based services such as weather widgets, local yellow page widgets, and map/navigation widgets).

Applications 136 optionally include the following modules (or sets of instructions), or a subset or superset thereof:
- Contacts module 137 (sometimes called an address book or contact list);
- Telephone module 138;
- Video conference module 139;
- E-mail client module 140;
- Instant messaging (IM) module 141;
- Workout support module 142;
- Camera module 143 for still and/or video images;
- Image management module 144;
- Video player module;
- Music player module;
- Browser module 147;
- Calendar module 148;
- Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
- Widget creator module 150 for making user-created widgets 149-6;
- Search module 151;
- Video and music player module 152, which merges video player module and music player module;
- Notes module 153;
- Map module 154; and/or
- Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone module 138, video conference module 139, e-mail client module 140, or IM module 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs (such as computer programs (e.g., including instructions)), procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
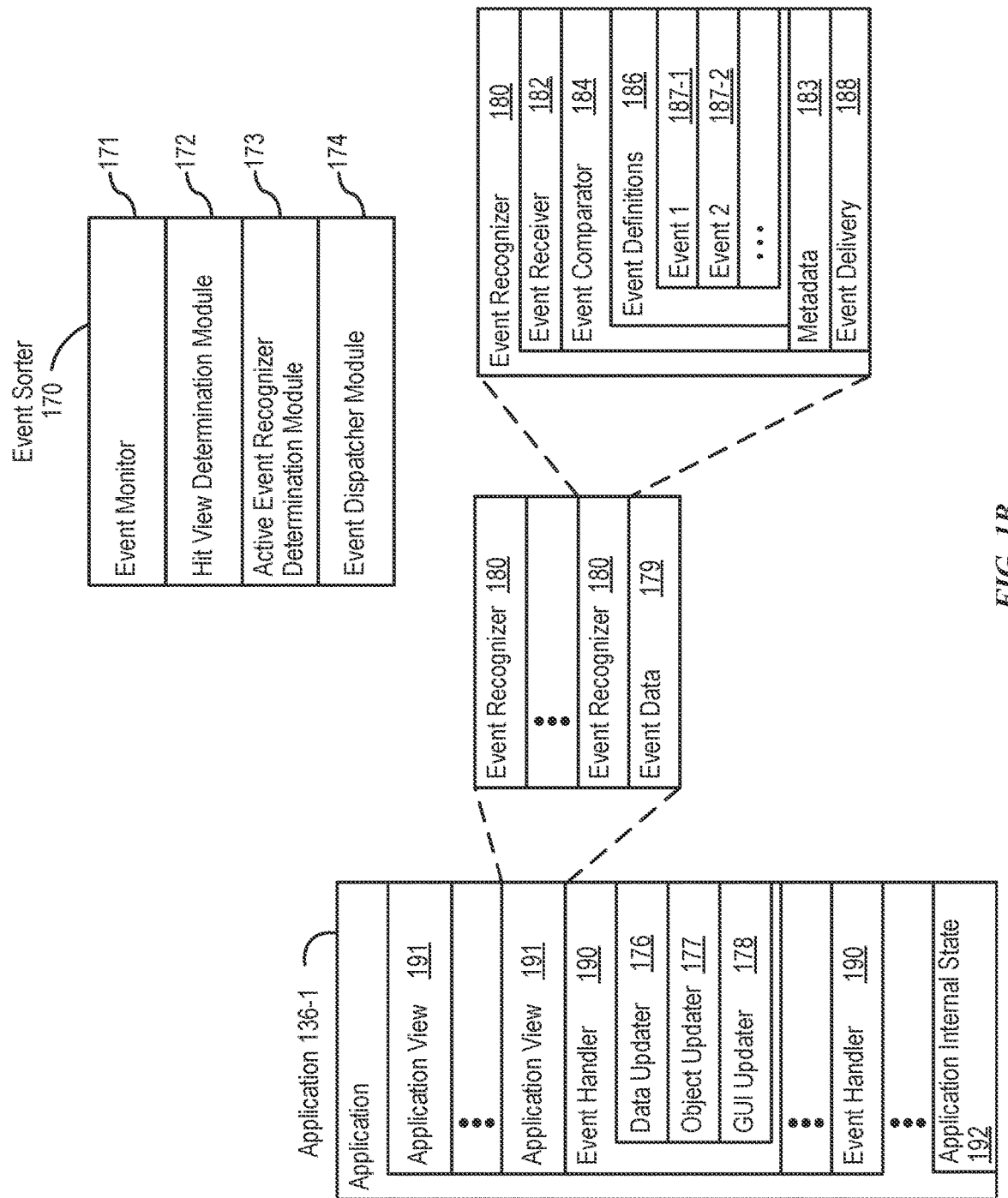
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (e.g., 187-1 and/or 187-2) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definitions 186 include a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
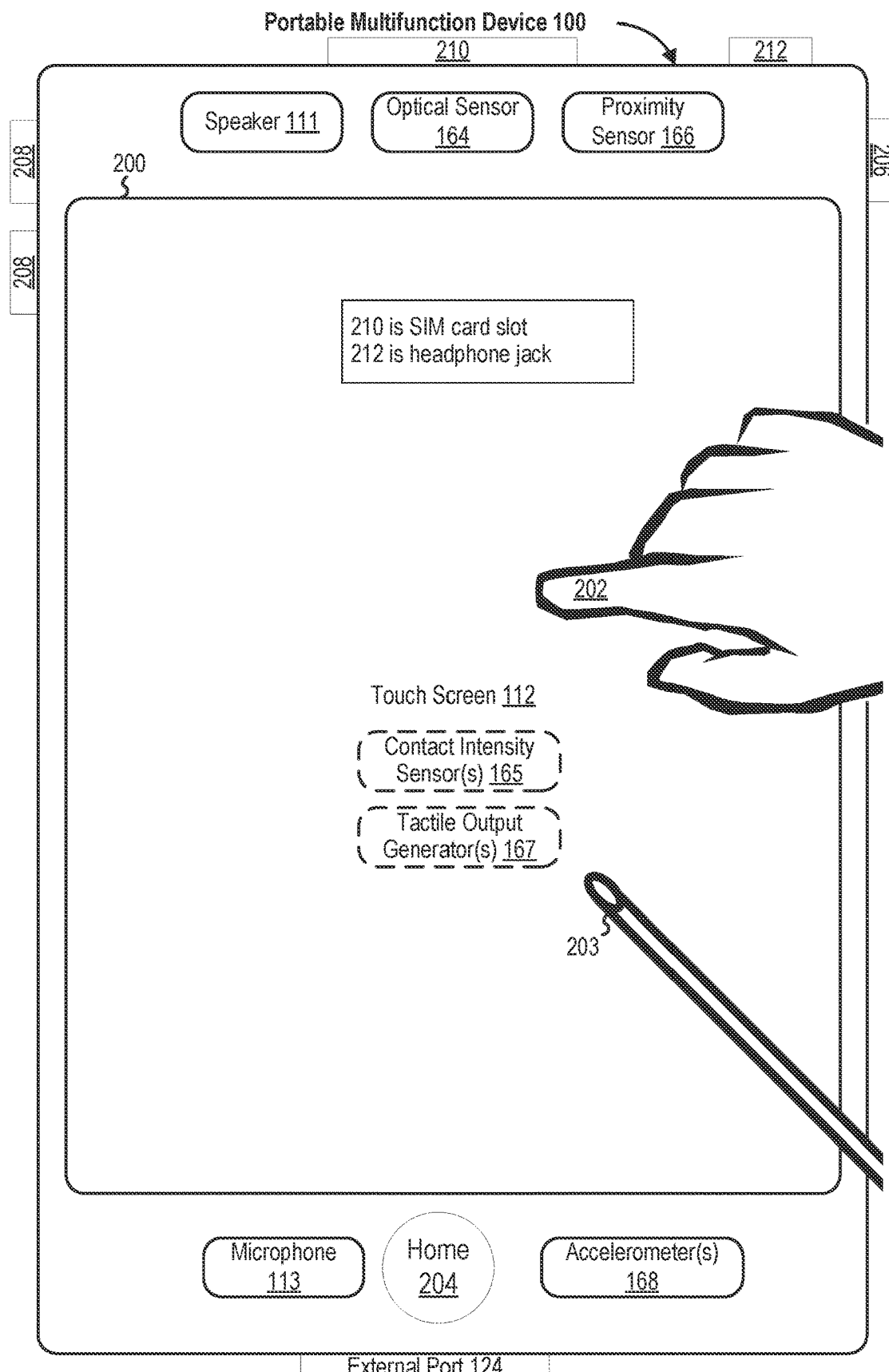
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or computer programs (e.g., sets of instructions or including instructions) need not be implemented as separate software programs (such as computer programs (e.g., including instructions)), procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
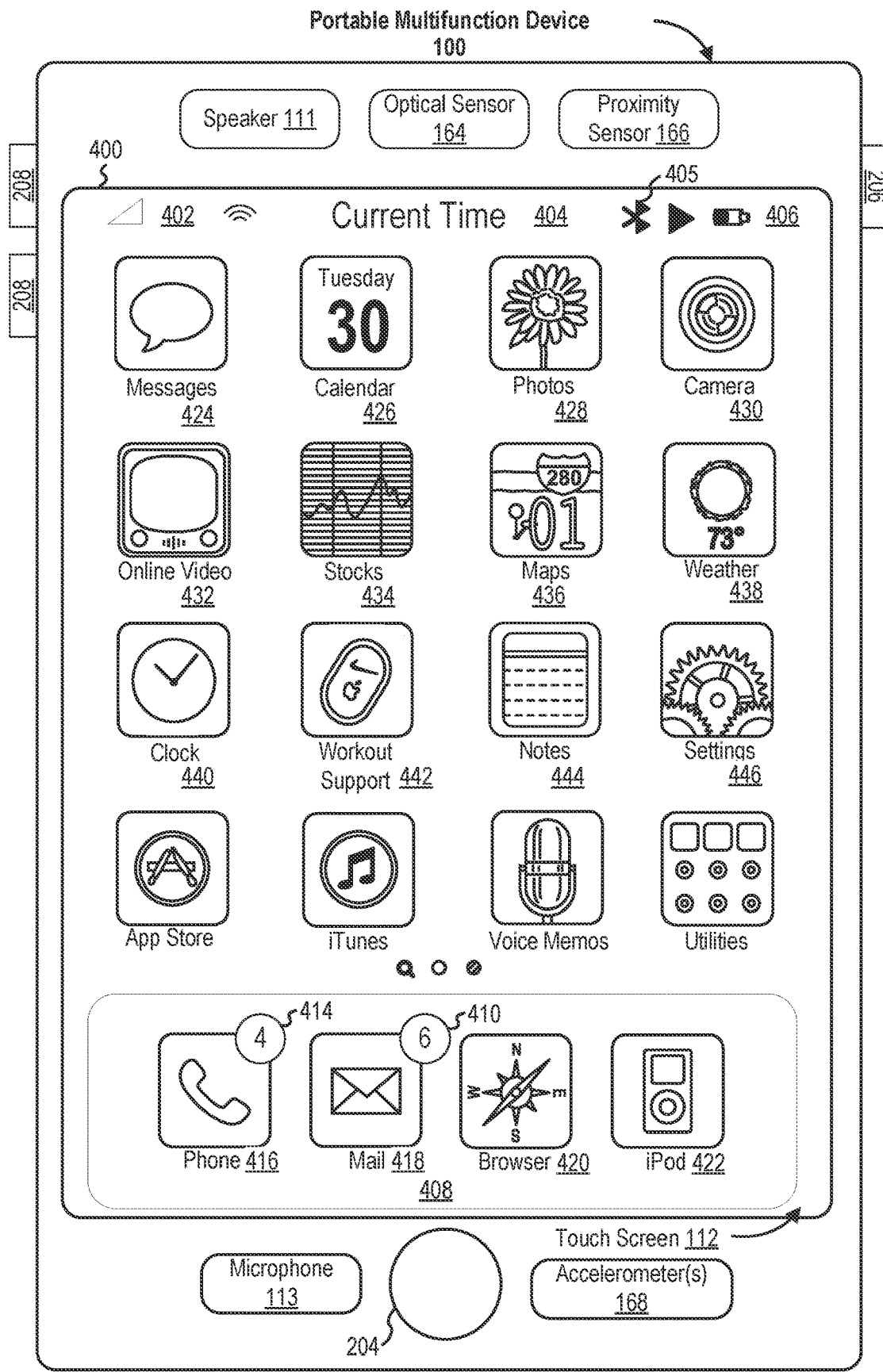
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar;"

Icon 428 for image management module 144, labeled "Photos;"

Icon 430 for camera module 143, labeled "Camera;"

Icon 432 for online video module 155, labeled "Online Video;"

Icon 434 for stocks widget 149-2, labeled "Stocks;"

Icon 436 for map module 154, labeled "Maps;"

Icon 438 for weather widget 149-1, labeled "Weather;"

Icon 440 for alarm clock widget 149-4, labeled "Clock;"

Icon 442 for workout support module 142, labeled "Workout Support;"

Icon 444 for notes module 153, labeled "Notes;" and

Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
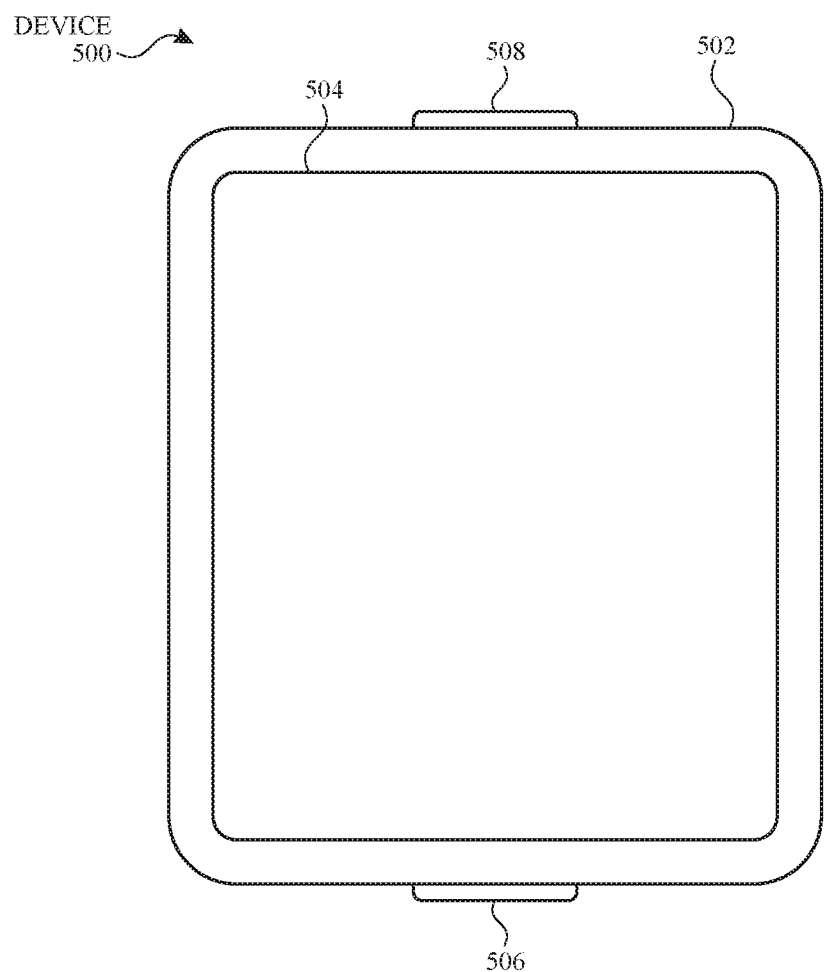
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
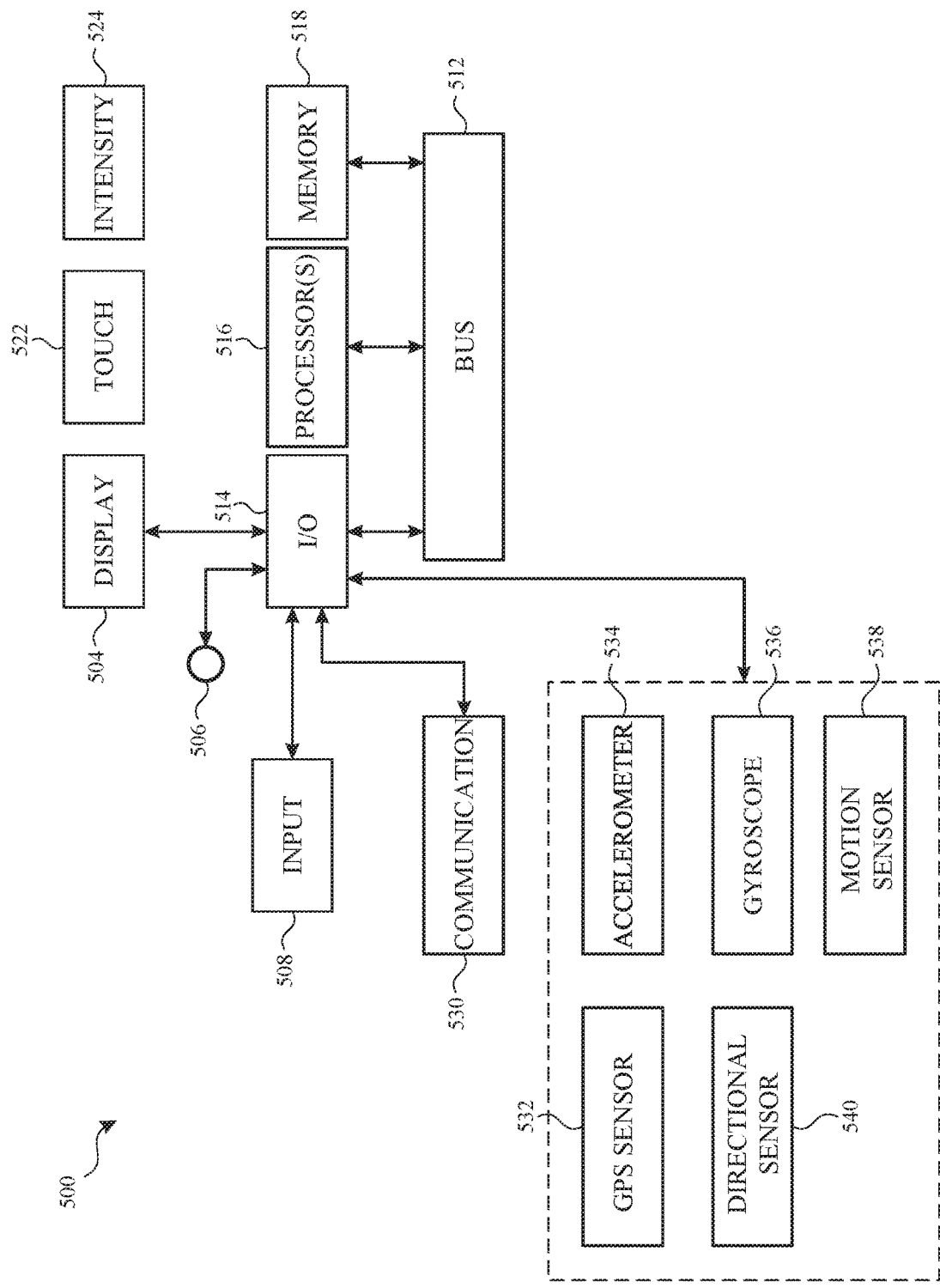
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to touch screen 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700, 900, 1100, and 1300 (FIGS. 7, 9, 11, and 13). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

Attention is now directed towards embodiments of user interfaces ("UI") and associated processes that are implemented on an electronic device, such as portable multifunction device 100, device 300, or device 500.

FIGS. 6A-6G illustrate exemplary user interfaces for adding a signed clinical record to a computer system, in accordance with some embodiments. The user interfaces in these figures are used to illustrate the processes described below, including the processes in FIG. 7.

Figure 6B:
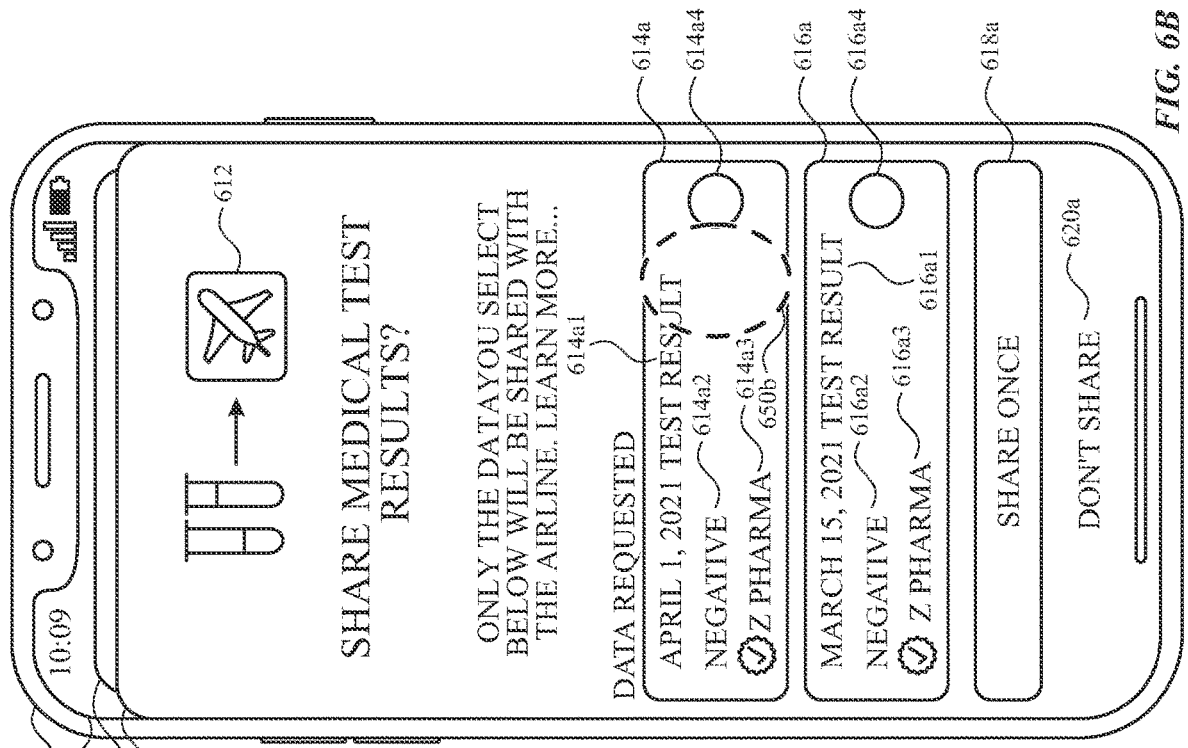
Figure 6A:
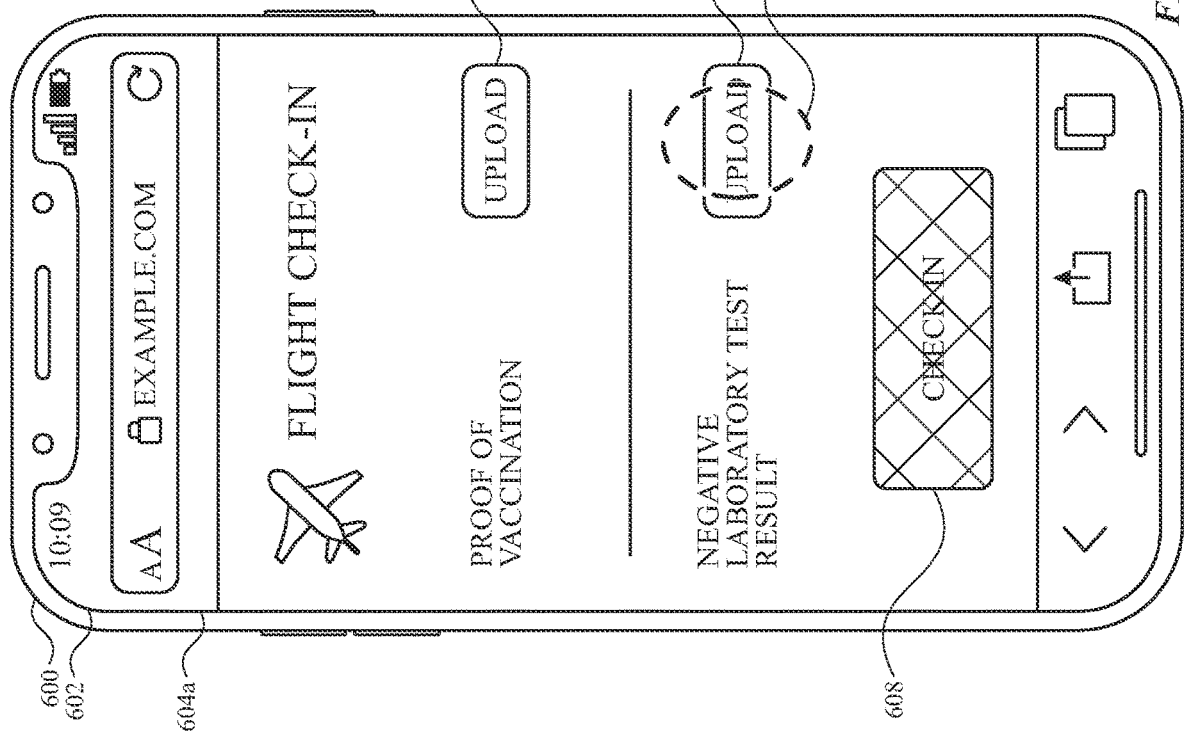

In FIG. 6A, computer system 600 displays check-in user interface 604a, which is a third-party airline's website. The third party airline is neither the manufacturer of computer system 600, nor the creator of the operating system running on computer system 600. Check-in user interface 604a is a webpage for checking into a flight associated with the third-party airline. Check-in user interface website includes check in affordance 608 which, at check-in user interface

604*a*, is grayed out to indicate that check in affordance 608 is not selectable. Check-in user interface 604*a* includes affordances for submitting proof of vaccination and negative laboratory test results, which are required before a user is able to check in to the flight associated with the third-party airline. In particular, check-in user interface 604*a* includes upload affordance 606*a* and upload affordance 606*b* which, when selected, cause the third-party airline (e.g., the third-party requestor) to request one or more clinical records from computer system 600. In some embodiments, in response to receiving the request for one or more clinical records, computer system 600 initiates a process for sharing a corresponding clinical record (e.g., by uploading proof of vaccination and/or a negative laboratory test result). In some embodiments, computer system 600 includes one or more features of devices 100, 300, and/or 500.

In FIG. 6A, computer system 600 receives input 650*a* (e.g., a tap input) on upload affordance 606*b* and, in response, initiates a process for uploading a negative laboratory test result. In some embodiments, initiating the process for uploading a negative laboratory test result causes computer system 600 to display a sharing user interface (e.g., sharing user interface 610*a*), as illustrated in FIG. 6B. In some embodiments, initiating the process for uploading the negative laboratory test result causes computer system 600 to display files user interface 634 (as discussed in reference to FIG. 6G). In some embodiments, the process for uploading the negative laboratory test result involves displaying files user interface 634 at least partially based on a determination that computer system 600 does not have a clinical record satisfying certain criteria available (e.g., computer system 600 does not have access to a signed clinical record that includes proof of vaccination).

In FIG. 6B, in response to receiving tap input 650*a* on upload affordance 606*b*, computer system 600 displays sharing user interface 610*a*. Sharing user interface 610*a* is a user interface for selecting one or more clinical records to be shared with the third party associated with third-party user interface 604*a* (e.g., the third-party airline). Sharing user interface 610*a* includes affordances corresponding to clinical records that satisfy criteria provided by the third-party airline (e.g., a test result with a negative result, a test result received within a threshold time period (e.g., the last 2 weeks, the last 30 days)).

Sharing user interface 610*a* includes visual indications of the third-party requestor (e.g., the third-party airline). For example, sharing user interface 610*a* is displayed partially overlapping check-in user interface 604*a*, such that at least a portion of check-in user interface 604*a* remains visible while sharing user interface 610*a* is displayed. Further, sharing user interface 610*a* includes icon 612, which is a graphical indication (e.g., a logo) that corresponds to the third-party (e.g., the third-party airline) with which the clinical records are being shared.

Sharing user interface 610*a* includes affordances corresponding to clinical records that satisfy criteria provided by the third-party airline. The affordances can be selected via user inputs (e.g., a tap input) to share corresponding clinical records with the third-party airline.

Sharing user interface 610*a* further includes result affordance 614*a*, which corresponds to a clinical record that includes a negative test result. Result affordance 614*a* includes test info 614*a*1 that includes an indication of the type of clinical record and/or the time and/or date on which the corresponding test was performed, result 614*a*2 that indicates the results of the corresponding lab test (e.g., negative), provider 614*a*3 that indicates the lab test administrator (e.g., Z Pharma), and selection indicator 614*a*4 that indicates whether result affordance 614*a* is currently selected to be shared with the third-party airline. In FIG. 6B, result affordance 614*a* has not been selected to be shared with the third-party airline, so selection indicator 614*a*4 provides a graphical indication that result affordance 614*a* is not selected (e.g., a circle without a checkmark inside).

Sharing user interface 610*a* further includes result affordance 616*a*, which corresponds to a second clinical record that includes a negative test result. Like result affordance 614*a*, result affordance 616*a* includes test info 616*a*1 that includes an indication of the type of clinical record and/or the time and/or date on which the corresponding test was performed, result 616*a*2 that indicates the results of the corresponding lab test (e.g., negative), provider 616*a*3 that indicates the lab test administrator (e.g., Z Pharma), and selection indicator 616*a*4 that indicates that result affordance 616*a* has not been selected to be shared with the third-party airline. In some embodiments, if the requested criteria are not met by the result that corresponds to result affordance 616*a* (e.g., a request for only results in the current month), result affordance 616*a* would not be included in sharing user interface 610*a*.

Sharing user interface 610*a* further includes share once affordance 618*a* that, when selected, causes computer system 600 to share (e.g., transmit) selected clinical records to the third-party requestor (e.g., the third-party airline). Sharing user interface further includes do not share affordance 620*a* that, when selected, causes computer system 600 to forego sharing selected clinical records with the third-party requestor (e.g., the third-party airline) and display a previously displayed interface (e.g., check-in user interface 604*a*) without displaying sharing user interface 610*a*. In FIG. 6B, computer system 600 receives user input 650*b* (e.g., a tap input) on result affordance 614*a*, which causes computer system 600 to select the clinical record corresponding to result affordance 614*a* to be shared with the third-party airline.

In FIG. 6C, in response to receiving input 650*b* on result affordance 614*a*, computer system 600 displays sharing user interface 610*b*, which is an updated version of sharing user interface 610*a* wherein selection indicator 614*b*4 has been updated to indicate that the clinical record associated with result affordance 614*b* is now selected to be shared (e.g., with the third-party airline). Sharing user interface 610*b* further includes result affordance 616*b*, which corresponds to 616*a*, and which includes indicator 616*b*4 that indicates that result affordance 616*b* is still not selected.

Sharing user interface 610*b* further includes share once affordance 618*b* and do not share affordance 620*b*, which correspond to share once affordance 618*a* and do not share affordance 620*a* as described above. In sharing user interface 610*b*, computer system 600 receives input 650*c* (e.g., a tap input) on share once affordance 618*b*, and receives input 650*d* (e.g., a tap input) on do not share affordance 620*b*.

In FIG. 6D, in response to receiving input 650*c* on share once affordance 618*b*, computer system 600 displays check-in user interface 604*b*. Check-in user interface 604*b* is an updated version of check-in user interface 604*a*, and has been updated to reflect that the negative laboratory test result has been received by the third-party airline. In contrast to check-in user interface 604*a*, check-in user interface 604*b* includes received indicator 622 indicating that the negative laboratory test results were received by the third-party airline, and does not include upload affordance 606*a* (as the corresponding clinical records have already been received).

Check-in user interface 604b further includes check in affordance 608, which is still grayed out to indicate that it is still not selectable. Check-in user interface 604b indicates that proof of vaccination is still required before check in is available, as it still includes upload affordance 606b (which corresponds to upload affordance 606a) for uploading (e.g., sharing) proof of vaccination. In some embodiments, a third party may request more than or fewer than two clinical records to be shared. In some embodiments, a check in affordance would become selectable after uploading a negative laboratory test result or proof of vaccination (as opposed to requiring both, as illustrated in FIG. 6D). In some embodiments, a third-party requestor may require a user to upload (e.g., share) three or more types of clinical records before proceeding in an analogous manner (e.g., to proceed with a transaction, to purchase a ticket, to book an appointment). In FIG. 6D, computer system 600 receives input 650e (e.g., a tap input) on upload affordance 606b.

In FIG. 6E, in response to receiving input 650e on upload affordance 606b, computer system 600 displays sharing user interface 624. Sharing user interface 624 is a user interface for sharing proof of vaccination (e.g., in the same manner as the negative laboratory test result was shared as described above with reference to FIGS. 6B-6C). Sharing user interface 624 includes contents similar to sharing user interface 604a, but for clinical records that correspond to proof of vaccination instead of a negative laboratory test result. Sharing user interface 624 includes dose affordance 624a, which corresponds to a first clinical record corresponding to a vaccine (e.g., a dose of a vaccine) and dose affordance 624b which corresponds to a second clinical record corresponding to a vaccine (e.g., a second dose of a vaccine). As illustrated in FIG. 6E, dose affordance 624a and dose affordance 624b have been selected to be shared with the third-party requestor (e.g., the third party airline). In some embodiments, sharing user interface 624 is initially displayed with both dose affordances unselected.

Like sharing user interface 604a, sharing user interface 624 includes visual indications of the third-party requestor (e.g., the third-party airline). For example, sharing user interface 624 is displayed partially overlapping check-in user interface 604b, such that at least a portion of check-in user interface 604b remains visible while sharing user interface 624 is displayed. Further, sharing user interface 624 includes icon 612.

Sharing user interface 624 includes dose affordance 624a, which includes date 624a1 that indicates the time and/or date on which the corresponding dose was received, type 624a2 that indicates the type of vaccine dose administered, and source 624a3 that indicates the provider of the clinical record (e.g., the location at which the dose was administered, the entity that generated and/or provided the signed clinical record corresponding to dose affordance 624a), and selection indicator 624a4 that indicates whether dose affordance 624a is currently selected to be shared with the third-party airline. Similarly, sharing user interface includes dose affordance 624b, which includes date 624b1 that indicates the time and/or date on which the corresponding dose was received, type 624b2 that indicates the type of vaccine dose administered, and source 624b3 that indicates the provider of the clinical record, and selection indicator 624b4 that indicates whether result affordance 624b is currently selected to be shared with the third-party airline. In sharing user interface 625, selection indicator 624a4 and selection indicator 624b4 indicate that the corresponding dose affordances are selected to be shared with the third-party airline. At FIG. 6E, computer system 600 receives input 650f (e.g., a tap input) and, in response, shares the selected proof of vaccination information (e.g., the clinical record corresponding to dose affordance 624a and the clinical record corresponding to dose affordance 624b) with the third-party airline.

In FIG. 6F, in response to receiving input 650f on share once affordance 628, computer system 600 displays check-in user interface 604c. Check-in user interface 604c is an updated version of check-in user interface 604c, and has been updated to reflect that the proof of vaccination has been received by the third-party airline. In contrast to check-in user interface 604b, check-in user interface 604c includes received indicator 632 that indicates that the proof of vaccination was received by the third-party airline. Accordingly, check-in user interface 604c does not include upload affordance 606b, as the proof of vaccination has already been received. Notably, check in affordance 608 is selectable (e.g., not grayed out) in FIG. 6F, in accordance with the requisite clinical records data (proof of vaccination and negative laboratory test results) having been submitted to the third-party airline.

Figure 6G:
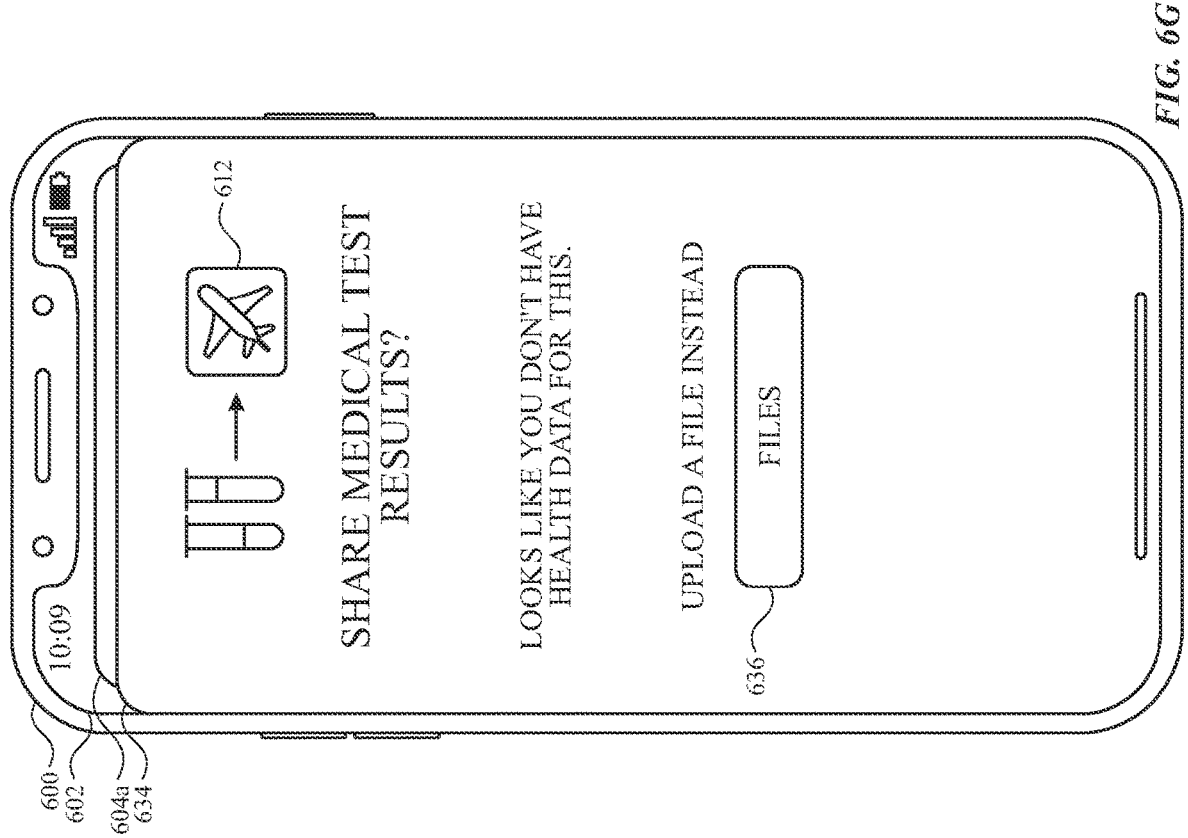

In FIG. 6G, computer system 600 displays files user interface 634 in response to receiving a request for a clinical record based on a determination that computer system 600 does not have a clinical record satisfying certain criteria available (e.g., computer system 600 does not have access to a signed clinical record that includes proof of vaccination). For example, in response to receiving input 650a on upload affordance 606a, if computer system 600 receives a request for a clinical record that includes a negative laboratory test result but does not have access to a clinical record that includes a negative laboratory test result, computer system 600 displays files user interface 634 instead of displaying sharing user interface 604a.

Files user interface 634 includes visual indications of the third-party requestor (e.g., the third-party airline), similar to sharing user interface 604a. For example, sharing user interface 634 is displayed partially overlapping check-in user interface 604a, such that at least a portion of check-in user interface 604a remains visible while sharing user interface 634 is displayed. Further, sharing user interface 610a includes icon 612.

Files user interface 634 further includes an indication that computer system 600 does not have a clinical record that was requested, and includes files affordance 636 which, when selected, causes computer system 600 to display a files navigation user interface for selecting one or more files to share with the third-party airline (e.g., a picture of a physical health record, such as a vaccine card and/or a test result).

FIG. 7 is a flow diagram illustrating a method for adding a signed clinical record to a computer system using a computer system (e.g., a smartphone, a smartwatch, a wearable electronic device, a desktop computer, a laptop, a tablet) in accordance with some embodiments. Method 700 is performed at a computer system (e.g., 100, 300, 500) that is in communication with a display generation component and one or more input devices (e.g., a mouse, a keyboard, a touch-sensitive surface). Some operations in method 700 are, optionally, combined, the orders of some operations are, optionally, changed, and some operations are, optionally, omitted.

As described below, method 700 provides an intuitive way for adding a signed clinical record to a computer system. The method reduces the cognitive burden on a user for adding a signed clinical record to a computer system, thereby creating a more efficient human-machine interface. For battery-operated computing devices, enabling a user to add a signed clinical record to a computer system faster and more efficiently conserves power and increases the time between battery charges.

The computer system (e.g., 600) receives (702), via the one or more input devices (e.g., 602), a request (e.g., a request triggered by input 650a or input 650e) (e.g., from a third-party website, from a second computer system different from the computer system, from a remote server) for a clinical record (e.g., a vaccine record, a test result, a lab result, a physiological measurement) that satisfies a first set of criteria (e.g., criteria transmitted with a request triggered by input 650a or input 650e) (e.g., a type of clinical record, a positive test result, a negative test result).

In response to receiving the request for a clinical record that satisfies the first set of criteria: in accordance with a determination that the computer system (e.g., 600) has access to (706) (e.g., the one or more records are stored at the computer system; stored on an external computer system in communication with the computer system) one or more clinical records that satisfy the first set of criteria, the computer system displays (704), via the display generation component (e.g., automatically, without additional user inputs) a sharing user interface (e.g., 610a), wherein the sharing user interface includes a user-interactive graphical user interface object (e.g., 614a) (e.g., an affordance) that, when selected, initiates a process for sharing a first (e.g., at least a first) clinical record (e.g., 614a, 616a, 624a, 624b) of the one or more clinical records with one or more external electronic devices (e.g., with the third-party website, with a second computer system different from the computer system, with a remote server).

Further in response to receiving the request for a clinical record that satisfied the first set of criteria: in accordance with a determination that the computer system does not have access to one or more clinical records that satisfy the first set of criteria, the computer system (e.g., 600) foregoes displaying (708) the sharing user interface (e.g., 610a). In some embodiments, the computer system displays an indication that no matching clinical record was found (e.g., 634). Conditionally displaying a sharing user interface in response to receiving a request for a clinical record that satisfies a first set of criteria based on a determination about whether the computer system has access to one or more clinical records that satisfy the first set of criteria provides the user with a user interface for sharing the clinical records that satisfy the first set of criteria if the computer system has access to such clinical records, without requiring the user to manually determine whether they have access to clinical records that satisfy the criteria, which performs an operation when a set of conditions has been met without requiring further user input.

In some embodiments, the first set of criteria includes a criterion that is satisfied when the one or more clinical records are signed (e.g., digitally signed/certified) (e.g., as indicated by 614a3). In some embodiments, a signed clinical record is a clinical record that includes electronic verification information (e.g., information related to a prescribing doctor and/or information indicating that the clinical record was received electronically from a testing/lab facility) and/or information that includes data (e.g., a public key of a public-private key pair) for validating the integrity and/or authenticity of the record. In some embodiments, the first set of criteria includes a criterion that is satisfied when the one or more clinical records are signed with a valid/validated digital signature/certification. Conditionally displaying a sharing user interface (e.g., 610a) in response to receiving a request for a clinical record that satisfies a first set of criteria, wherein the first set of criteria includes a criterion that is satisfied when the one or more clinical records are signed, provides the user with a user interface for sharing the clinical records if the computer system has access to signed clinical records, without requiring the user to manually determine whether they have access to signed clinical records, which performs an operation when a set of conditions has been met without requiring further user input.

In some embodiments, the first clinical record (e.g., 614a) corresponds to a clinical event selected from the group consisting of: an eye examination (e.g., a medical examination performed by an optometrist or an ophthalmologist), a lab test (e.g., 614a, 616a) (e.g., the administration of an antibodies test, a strep test, a blood type test), a vaccination (e.g., 624a, 624b) (e.g., the administration or recordation of a vaccination), a prescription (e.g., a doctor's writing or issuance of a prescription), a physiological measurement (e.g., a measurement of a person's blood glucose, creatinine, iron, or LDL cholesterol), and a combination thereof. Conditionally displaying a sharing user interface (e.g., 610a) in response to receiving a request for a clinical record that satisfies a first set of criteria based on a determination about whether the computer system (e.g., 600) has access to one or more clinical records that satisfy the first set of criteria, wherein the clinical record corresponds to a clinical event selected from the group consisting of an eye exam, a lab test, a vaccination, a prescription, or a physiological measurement, and a combination thereof, provides the user with a user interface for sharing the clinical records corresponding to a corresponding clinical event if the computer system has access to a clinical record that corresponds to one of the designated clinical events, without requiring the user to manually determine whether they have access to a clinical record that corresponds to one of the designated clinical events, which performs an operation when a set of conditions has been met without requiring further user input.

In some embodiments, the request for a clinical record that satisfies a first set of criteria is received while the computer system (e.g., 600) is displaying, via the display generation component (e.g., 602), a first user interface that corresponds to a third party (e.g., 604a) (e.g., a website corresponding to a third party (e.g., an airline, a pharmacy, a glasses vendor) different from the manufacturer of the computer system (e.g., the provider of the operating system of the computer system), an application provided by (e.g., developed by) a third party different from the manufacturer of the computer system). In some embodiments, the request is a user input (e.g., 650a) corresponding to a user-interactive graphical user interface object (e.g., 606) that is included in the user interface that corresponds to the third party.

In some embodiments, after initiating the process for sharing the first clinical record of the one or more clinical records with one or more external electronic devices, the computer system (e.g., 600) detects completion of the process for sharing the first clinical record of the one or more clinical records with one or more external electronic devices (e.g., as indicated by 622). In some embodiments, in response to detecting completion of the process for sharing the first clinical record of the one or more clinical records with one or more external electronic devices, the computer system displays (e.g., re-displaying; automatically displaying without requiring further user input), via the display generation component, (e.g., 602) a second user interface (e.g., 604b) that corresponds to the third party. In some embodiments, the second user interface that corresponds to the third party is different from the first user interface (e.g.,

604a) that corresponds to the third party (e.g., is a confirmation user interface corresponding to the third party. In some embodiments, the second user interface that corresponds to the third party is displayed (e.g., automatically) after the first clinical record has been shared with the one or more external electronic devices. In some embodiments, displaying the second user interface that corresponds to the third party after initiating the process for sharing the first clinical record of the one or more clinical records with one or more external electronic devices includes displaying an updated version of the first user interface that corresponds to the third party that includes an indication (e.g., 622) that the process for sharing the first clinical record has been initiated and/or completed. Displaying a second user interface that corresponds to the third party in response to detecting completion of the process for sharing the first clinical record with one or more external devices enables the computer system to display the second user interface that corresponds to the third party when the clinical record has been shared without requiring the user to navigate (e.g., manually) to the second user interface that corresponds to the third party, which performs an operation when a set of conditions has been met without requiring further user input.

In some embodiments, while displaying the sharing user interface (e.g., 610a), the computer system (e.g., 600) detects, via the one or more input devices, a user input (e.g., 650c) (e.g., a tap input) corresponding to selection of the user-interactive graphical user interface object (e.g., 618a). In some embodiments, in response to detecting the user input, the computer system (e.g., 600) shares (e.g., transmitting) data corresponding to one or more clinical records that satisfy the first set of criteria with the third party. In some embodiments, sharing data corresponding to one or more clinical records that satisfy the first set of criteria with the third party includes transmitting data corresponding to one or more clinical records that satisfy the first set of criteria to a computer system associated with the third party (e.g., a remote server owned and/or maintained by the third party). Sharing data corresponding to one or more clinical records that satisfy the first set of criteria with the third party in response to detecting a user input while displaying the sharing user interface reduces the number of inputs needed to perform an operation (e.g., to share data corresponding to one or more clinical records that satisfy a first set of criteria).

In some embodiments, the sharing user interface (e.g., 610a) includes a graphical indicator (e.g., 612) that corresponds to the third party (e.g., a logo, an icon). In some embodiments, the sharing user interface is partially overlaid on the user interface (e.g., 604a) that corresponds to the third party such that at least a portion of the user interface that corresponds to the third party is still visible while displaying the sharing user interface. Displaying a graphical indicator that corresponds to the third party in the sharing user interface allows the user to quickly recognize the potential recipient of the clinical records data that a user may choose to share from the sharing user interface, thereby providing improved visual feedback to the user.

In some embodiments, the first set of criteria includes a criterion that is satisfied when the one or more clinical records satisfy a time range requirement (e.g., as discussed with reference to FIG. 6B) (e.g., one or more clinical records are dated within the last 5, 10, 15 days; dated from January 1st to February 1st of a specific year) provided by the request. In some embodiments, the request provides a user-inputted time range requirement. In some embodiments, the request is made by selecting a user-interactive graphical user interface object that corresponds to a predetermined time range requirement). Conditionally displaying a sharing user interface in response to receiving a request for a clinical record that satisfies a first set of criteria, wherein the first set of criteria includes a criterion that is satisfied when the one or more clinical records satisfy a time range requirement provided by the request, provides the user with a user interface for sharing the clinical records that satisfy the time range requirement provided by the request, without requiring the user to manually determine whether the clinical records satisfy the time range requirement provided by the request, which performs an operation when a set of conditions has been met without requiring further user input.

In some embodiments, the first set of criteria includes a criterion that is satisfied when the one or more clinical records include a requested result type (e.g., as discussed with reference to FIG. 6B) (e.g., a positive result; a negative result; a result having a value within a specified range (e.g., heart rate between 50 BPM and 120 BPM)). Conditionally displaying a sharing user interface in response to receiving a request for a clinical record that satisfies a first set of criteria, wherein the first set of criteria includes a criterion that is satisfied when the one or more clinical records includes a requested result type, provides the user with a user interface for sharing the clinical records that include the requested result type, without requiring the user to manually determine whether the clinical records include the requested result type, which performs an operation when a set of conditions has been met without requiring further user input.

In some embodiments, the first clinical record satisfies the first set of criteria, a second clinical record satisfies the first set of criteria, and the sharing user interface (e.g., 610a) includes: the user-interactive graphical user interface object (e.g., 614a) that, when selected, initiates the process for sharing the first clinical record of the one or more clinical records with one or more external electronic devices and a second user-interactive graphical user interface object (e.g., 616a) that, when selected, initiates a process for sharing the second clinical record of the one or more clinical records with one or more external electronic devices. In some embodiments, multiple, discrete sharing affordances are displayed when a plurality of qualifying clinical records are identified, thereby allowing the user to selectively share individual qualifying clinical records. Displaying multiple options for initiating the process for sharing one or more clinical record in the sharing user interface reduces the number of inputs needed to perform an operation (e.g., to select and share data corresponding to one or more clinical records).

In some embodiments, the process for sharing the first clinical record of the one or more clinical records with one or more external electronic devices includes sharing the first clinical record of the one or more clinical records with one or more external electronic devices without enabling ongoing sharing of clinical records (e.g., future clinical records that become accessible to the computer system later) that satisfy the first set of criteria. In some embodiments, the sharing user interface includes a separate "do not share user-interactive graphical user-interactive object" (e.g., 620a) that, when selected, causes the computer system to return to a previously displayed user interface corresponding to a third party without sharing data corresponding to clinical records. In some embodiments, the sharing user interface includes indications of one or more clinical records that will be shared as part of the process for sharing that is initiated by selection of the user-interactive graphical user interface object that, when selected, initiates a process for sharing a first (e.g., at least a first) clinical record of the one or more clinical records with one or more external electronic devices. Sharing current data corresponding to one or more clinical records that satisfy the first criteria without enabling ongoing sharing of the one or more clinical records enables the user to share clinical records for a limited duration of time without requiring the user to manually turn off sharing and/or configure sharing preferences to expire after a particular amount of time, which performs an operation when a set of conditions has been met without requiring further user input.

In some embodiments, the sharing user interface (e.g., 624) includes a graphical indication (e.g., 624a4) that the first clinical record is selected (e.g., currently selected via received user input) for sharing. In some embodiments, the sharing user interface includes a graphical indication (e.g., 624b4) that a third clinical record that satisfies the first set of criteria is selected for sharing. In some embodiments, the computer system (e.g., 600) receives, via the one or more input devices, a second user input (e.g., 650f) corresponding to the user-interactive graphical user interface object (e.g., 628) (e.g., an affordance) that, when selected, initiates a process for sharing the first clinical record of the one or more clinical records with one or more external electronic devices. In some embodiments, in response to receiving the second user input, the computer system shares the first clinical record and the third clinical record of the one or more clinical records with the one or more external electronic devices. Transmitting the first clinical record and the third clinical record in response to detecting a second user input corresponding to selection of the user-interactive graphical user interface object reduces the number of inputs needed to perform an operation (e.g., to share multiple clinical records (e.g., the selected clinical records) at once).

In some embodiments, the first clinical record is a first type of clinical record (e.g., a clinical record corresponding to specific type of health record (e.g., a specific test, physiological parameter (e.g., blood pressure; heart rate; blood glucose level); specific diagnosis for a specific disease; specific vaccination)). In some embodiments, after sharing the first clinical record of the one or more clinical records with the one or more external electronic devices, the computer system (e.g., 600) receives data corresponding to the first type of clinical record (e.g., an update to the first clinical record; a new clinical record that is the same type as the first clinical record). In some embodiments, in response to receiving the data corresponding to the first type of clinical record, foregoing sharing (e.g., automatically sharing) the data corresponding to the first type of clinical record with the one or more external devices (e.g., as discussed with reference to 618a). In some embodiments, selecting the share once user-interactive graphical user interface object causes current selected clinical records to be shared without causing future updates to the selected clinical records to be automatically shared. After sharing the first clinical record of a first type with one or more external devices, and in response to receiving data corresponding to the first type of clinical record, foregoing sharing the data corresponding to the first type of clinical record with the one or more external devices reduces the number of inputs required to perform an operation (e.g., to forego sharing data corresponding to the first lab type indefinitely and/or to turn off sharing).

Note that details of the processes described above with respect to method 700 (e.g., FIG. 7) are also applicable in an analogous manner to the methods described below. For example, method 900 optionally includes one or more of the characteristics of the various methods described above with reference to method 700. For example, a signed clinical record that is added to a computer system in the method described above could be displayed with an unsigned lab manually entered by a user, and the signed clinical record could be displayed with a verification identifier as described below with reference to method 900. For brevity, these details are not repeated below.

FIGS. 8A-8E illustrate exemplary user interfaces for displaying signed and unsigned clinical records, in accordance with some embodiments. The user interfaces in these figures are used to illustrate the processes described below, including the processes in FIG. 9.

In FIG. 8A, computer system 600 displays labs user interface 804, which includes clinical record affordance 810 that corresponds to a signed clinical record and clinical record affordance 812 that corresponds to an unsigned clinical record. Labs user interface 804 illustrates that signed clinical record and unsigned clinical records are concurrently displayed in labs user interface 804.

Clinical record affordance 810 includes record type 810a that indicates the type of clinical record that clinical record affordance 810 corresponds to, record details 810b that includes relevant information about the clinical record to which clinical record affordance 810 corresponds, and verification identifier 810c that indicates that the clinical record corresponding to clinical record affordance 810 is signed (e.g., a clinical record that includes electronic verification information (e.g., information related to a prescribing doctor, information indicating that the clinical record was received electronically from a testing/lab facility); information that includes data (e.g., a public key of a public-private key pair) for validating the integrity and/or authenticity of the record)).

Clinical record affordance 812 includes record type 812a that indicates the type of clinical record that clinical record affordance 812 corresponds to and record details 812b that includes relevant information about the clinical record to which clinical record affordance 812 corresponds. Notably, clinical record 812 does not include a verification identifier. In some embodiments, unsigned clinical record affordances included in labs user interface 804 are displayed without a verification identifier.

Figure 8D:
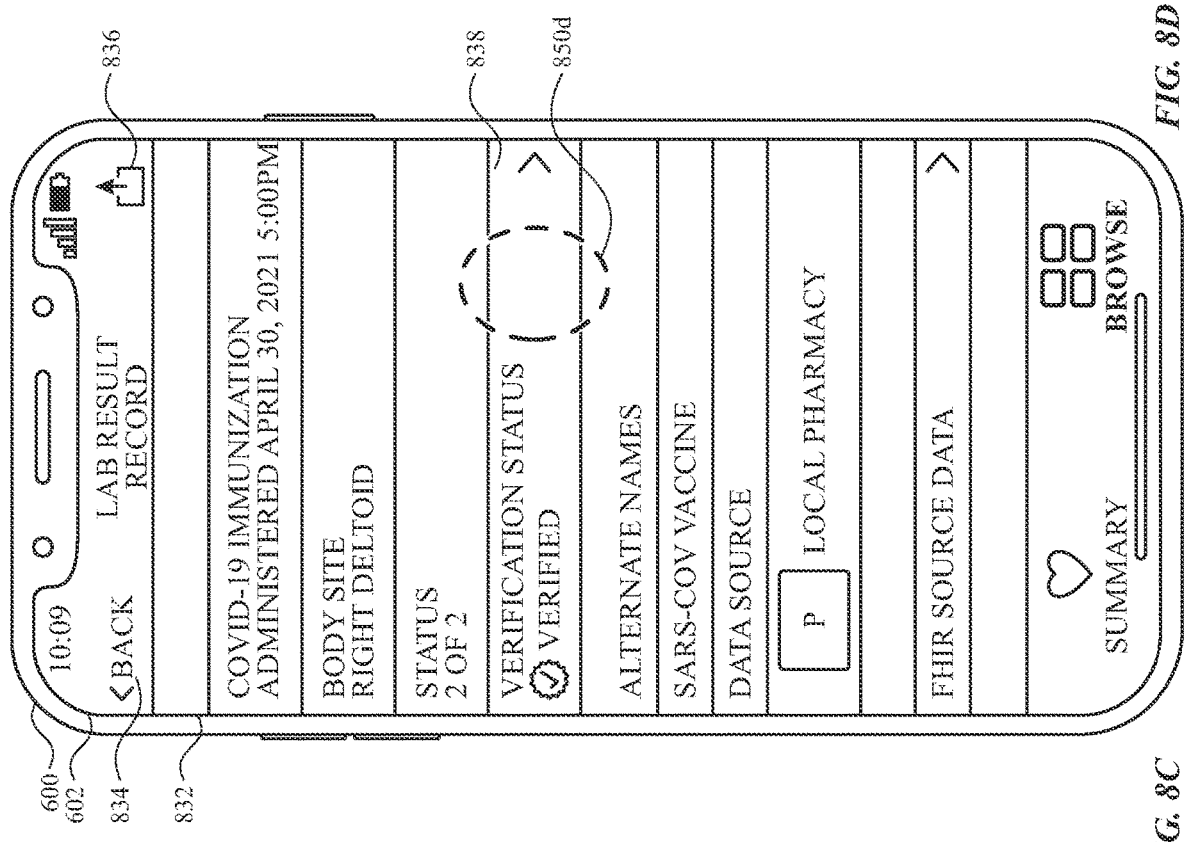

Labs user interface 804 further includes browse affordance 806 that, when selected, causes computer system 600 to display a previously displayed user interface. Labs user interface further includes edit affordance 808 which, when selected, displays a user interface for editing the labs information included in labs user interface 804 (e.g., by pinning and/or unpinning lab types, by deleting lab data, by manually entering lab data). Labs user interface 804 further includes search bar 815 which, when selected, causes computer 600 to display options for searching among the labs data that can be displayed in labs user interface 804 (e.g., by inputting letters corresponding to lab data via a touch keyboard, via voice inputs received via a microphone). Labs user interface 804 further includes chronological sort affordance 814a and alphabetical sort affordance 814b. Selecting chronological sort affordance 814a causes the labs data included in labs user interface 804 to be sorted (e.g., positioned) at least partially based on a chronological sorting criteria (e.g., most recent data on top). For example, selecting 814a (which is currently selected in FIG. 8A, as illustrated by the line around sort affordance 814a) causes the labs data to be sorted based on recency. In contrast, selecting sort affordance 814b causes the labs data to be sorted at least partially based on alphabetical order of corresponding labs information (e.g., alphabetical order according to a corresponding lab type). In FIG. 8A, computer system 600 receives input 850a on clinical record affordance 810, the response to which is discussed with reference to FIG. 8D. Computer system 600 also receives input 850b on clinical record affordance 812.

In FIG. 8B, in response to receiving input 850b, computer system 600 displays lab user interface 820. Lab user interface 820 includes the details of the clinical record that corresponds to clinical record affordance 812 (e.g., the COVID-19 Immunization dose 1 of 2 received on Apr. 9, 2021). Lab user interface 820 includes details such as the type of vaccine that was administered, the date and time on which the vaccine was administered, the body site at which the vaccine was administered, and the number dose that the administered vaccination corresponds to in a series of vaccine doses (e.g., 1 of 2). Lab user interface further includes an indication of the verification status of the vaccination record (e.g., vaccination status unverified), which indicates that the clinical record corresponding to the vaccination is unsigned. In some embodiments, the indication of the verification status corresponding to an unsigned clinical record is not selectable, whereas selecting the indication of the verification status corresponding to a signed clinical record causes computer system 600 to display a verified user interface as discussed below with reference to FIG. 8E.

Lab user interface 820 further includes photo 822, which is a photo that corresponds to the clinical record associated with lab user interface 820. In FIG. 8B, photo 822 is a photograph of a physical vaccine card that corresponds to the vaccination being represented in lab user interface 820.

Lab user interface further includes back affordance 816 which, when selected, causes computer system 600 to return to displaying lab user interface 804, as illustrated in FIG. 8A. Lab user interface 820 further includes share affordance 818 which, when selected, initiates a process for sharing information included in lab user interface 820 with a recipient (e.g., a recipient device). In FIG. 8B, computer system 600 receives input 850c (e.g., a tap input) on share affordance 818.

Figure 8C:
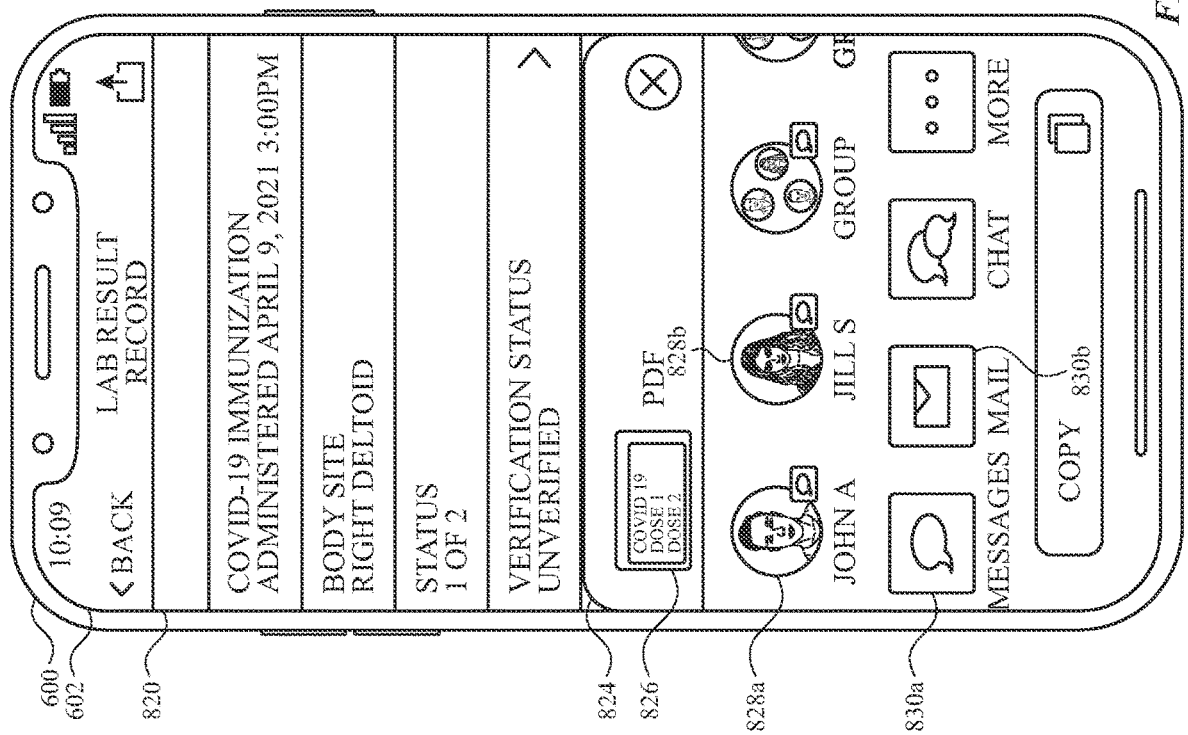

In FIG. 8C, in response to receiving input 850c, computer system 600 displays sharing user interface 824 overlaid on labs user interface 820 such that at least a portion of labs user interface 820 is still displayed concurrently with sharing user interface 824. Displaying sharing user interface 824 corresponds to initiating a process for sharing information included in lab user interface 820 with a recipient. In response to receiving input 850c, computer system 600 generates a file (e.g., a .pdf, a .jpg) containing information corresponding to the clinical record corresponding to labs user interface 820. Sharing user interface 824 includes preview image 826, which corresponds to a preview of the file.

Sharing user interface 824 includes options for sharing the file with a recipient (e.g., a recipient device) via various means. Sharing user interface includes recipient affordance 828a which, when selected, initiates a process for sharing the file with a first recipient, and recipient affordance 828b which, when selected, initiates a process for sharing the file with a second recipient different from the first recipient. Sharing user interface 824 further includes send method affordance 830a which, when selected, initiates a process for transmitting the file to a recipient using a first means of communication (e.g., a messaging application). Sharing user interface 824 further includes send method affordance 830b which, when selected, initiates a process for transmitting the file to a recipient using a second means of communication different from the first means of communication (e.g., an email application). Sharing user interface 824 further includes dismiss affordance 825 which, when selected, causes computer system 600 to return to displaying labs user interface 820 without displaying sharing user interface 824.

In FIG. 8D, in response to receiving input 850a on clinical record affordance 810 of FIG. 8A, computer system 600 displays lab user interface 832. Lab user interface 832 is similar to lab user interface 820 in that it includes the details of a clinical record, specifically the clinical record that corresponds to clinical record affordance 810 (e.g., the COVID-19 Immunization dose 2 of 2 received on Apr. 30, 2021). However, in contrast to lab user interface 820, lab user interface 832 includes verified affordance 838, which includes an indication that the clinical record corresponding to lab user interface 832 is signed. Lab user interface 832 further includes information related to the data source of the clinical record (e.g., "Data Source Local Pharmacy") which, in some embodiments, indicates the entity that provided verification information related to the signed clinical record. Lab user interface 832 further includes details related to the corresponding clinical record, such as the type of vaccine that was administered, the date and time on which the vaccine was administered, the body site at which the vaccine was administered, and the number dose that the administered vaccination corresponds to in a series of vaccine doses (e.g., 2 of 2).

Lab user interface 832 further includes back affordance 834 which, when selected, causes computer system 600 to return to labs user interface 804. Lab user interface 832 further includes share affordance 836 which, when selected, initiates a process for sharing the information related to the clinical record that corresponds to lab user interface 832 in a manner similar to that described above with reference to FIGS. 8B-8C. In FIG. 8D, computer system 600 receives input 850d (e.g., a tap input) on verified affordance 838 and, in response, displays additional related to the clinical record and/or physiological information about the recipient of the vaccine.

In FIG. 8E, in response to receiving input 850d on verified affordance 838, computer system 600 displays verified user interface 840. Verified user interface 840 is a screen containing details related to a signed clinical record, and contains information related to the clinical record and/or physiological information related to a patient associated with the signed clinical record that is not included in the lab user interface corresponding to the signed clinical record (e.g., lab user interface 832). For example, verified user interface includes manufacturer 846 that indicates the manufacturer and/or pharmaceutical entity associated with the signed clinical record (e.g., "Vaccine Makers"). Further, verified user interface includes verifying entity 848 that indicates a clinical establishment associated with the signed clinical record (e.g., the clinical establishment that administered a clinical procedure and, in some embodiments, provided the electronic signature information corresponding to the signed clinical record to computer system 600). Verified user interface 840 further includes patient information 852 that includes physiological information related to a person associated with the signed clinical record (e.g., the vaccine recipient). For example, in FIG. 8E, patient information 852 includes the name (e.g., "Jane Appleseed"), date of birth (Jun. 1, 1985), sex (Female), and home address (123 Main St., Cupertino, CA. 94154) of the patient who received the associated vaccine. Notably, at least some of the information included in verified user interface 840 is not included in lab user interface 832. Verified user interface further includes back affordance 842 which, when selected, causes computer system 600 to return to lab user interface 832, as described above with reference to FIG. 8D.

FIG. 9 is a flow diagram illustrating a method for displaying signed and unsigned clinical records using a computer system (e.g., a smartphone, a smartwatch, a wearable electronic device, a desktop computer, a laptop, a tablet) in accordance with some embodiments. Method 900 is performed at a computer system (e.g., 100, 300, 500) that is in communication with a display generation component and one or more input devices (e.g., a mouse, a keyboard, a touch-sensitive surface). Some operations in method 900 are, optionally, combined, the orders of some operations are, optionally, changed, and some operations are, optionally, omitted.

As described below, method 900 provides an intuitive way for adding a signed clinical record to a computer system. The method reduces the cognitive burden on a user for viewing and managing signed and unsigned clinical records, thereby creating a more efficient human-machine interface. For battery-operated computing devices, enabling a user to view and manage signed and unsigned clinical records faster and more efficiently conserves power and increases the time between battery charges.

The computer system (e.g., 600) displays (902), via the display generation component (e.g., 602), a clinical record user interface (e.g., 832) that includes a first set of information corresponding to a first clinical record (e.g., a vaccine record, a test result, a lab result, a physiological measurement).

Displaying the clinical record user interface includes in accordance with a determination that the first clinical record is a signed clinical record (e.g., a clinical record that includes electronic verification information (e.g., information related to a prescribing doctor, information indicating that the clinical record was received electronically from a testing/lab facility); information that includes data (e.g., a public key of a public-private key pair) for validating the integrity and/or authenticity of the record), displaying (904), via the display generation component (e.g., 602), a verification information user-interactive graphical user interface object (e.g., 838) (e.g., an affordance for viewing verification information corresponding to the clinical record).

Displaying the clinical record user interface (e.g., 820) includes in accordance with a determination that the first clinical record is an unsigned clinical record (e.g., a clinical record that does not include electronic verification information), foregoing displaying (906) the verification information user-interactive graphical user interface object (e.g., as seen in 812).

The computer system (e.g., 600) receives (908), via the one or more input devices, a user input (e.g., 850d) that corresponds to selection (e.g., a tap gesture, a swipe, a press input, and/or a mouse click) of the verification information user-interactive graphical user interface object (e.g., 838).

In response to receiving the user input (e.g., 850d) that corresponds to selection of the verification information user-interactive graphical user interface object (e.g., 838), the computer system (e.g., 600) displays (910) a verification user interface (e.g., 840), wherein the verification user interface includes physiological information (e.g., 852) corresponding to the first clinical record that was not included in the clinical record user interface (e.g., sex of a corresponding patient, date of birth of a corresponding patient). Conditionally displaying a verification information user-interactive graphical user interface object in accordance with a determination that a clinical record is signed allows a user to quickly recognize that the clinical record is signed, thereby providing improved visual feedback to the user.

In some embodiments, in accordance with a determination that the clinical record is an unsigned clinical record, the computer system (e.g., 600) displays the clinical record user interface (e.g., 820) with a photo user-interactive graphical user interface object (e.g., 822) that, when selected, causes the computer system to display a photo associated with the unsigned clinical record (e.g., picture of a test result, a picture of a vaccine card, a picture of a prescription). In some embodiments, in accordance with a determination that the clinical record is signed clinical record, the computer system displays the clinical record user interface (e.g., 832) without the photo user-interactive graphical user interface object that, when selected, causes the computer system to display a photo associated with the unsigned clinical record. In some embodiments, the photo user-interactive graphical user interface object includes at least a portion (e.g., a partial view) of the photo associated with the unsigned clinical record. Conditionally displaying a photo user-interactive graphical user interface object in accordance with a determination that a clinical record is unsigned provides visual feedback that the clinical record is unsigned, thereby providing improved visual feedback to the user.

In some embodiments, the clinical record user interface (e.g., 820) includes a plurality of physiological measurements (e.g., a measurements of a person's blood glucose, creatinine, iron, or LDL cholesterol, and/or eyes). Displaying a clinical record user interface that includes a plurality of physiological measurements, wherein displaying the clinical record user interface includes conditionally displaying a verification information user-interactive graphical user interface object (e.g., 838) in accordance with a determination that a clinical record is signed allows a user to quickly recognize which physiological measurements are signed (e.g., electronically verified) and which physiological measurements are unsigned (e.g., unverified), thereby providing improved visual feedback to the user.

In some embodiments, the clinical record user interface (e.g., 820) includes an audiogram. Displaying a clinical record user interface that includes an audiogram provides users with feedback as to the type of clinical records that are accessible at the computer system (e.g., 600), which provides improved visual feedback.

In some embodiments, the clinical record user interface (e.g., 600) includes an expired prescriptions user-interactive graphical user interface object (e.g., 1036). In some embodiments, the computer system (e.g., 600) detects, via the one or more input devices, a user input (e.g., a tap input) corresponding to selection of the expired prescriptions user-interactive graphical user interface object. In some embodiments, in response to detecting the user input corresponding to selection of the expired prescriptions user-interactive graphical user interface object, the computer system displays a user interface that includes information corresponding to one or more expired prescriptions (e.g., a glasses prescription, a contacts prescription, a drug prescription). Displaying an expired prescriptions user interface in response to an input corresponding to selection of an expired prescriptions user-interactive graphical user interface object reduces the number of inputs needed to perform an operation (e.g., to transition from a user interface for viewing active prescriptions to a user interface for viewing expired prescriptions).

In some embodiments, the clinical record user interface (e.g., 832) includes a share user-interactive graphical user interface object (e.g., 836) that, when selected, initiates a process for sharing information (e.g., outputting the information) corresponding to the first clinical record. In some embodiments, sharing a clinical record includes generating a file containing information related to the clinical record and transmitting the file to a recipient (e.g., a recipient's electronic device). Displaying a clinical record user interface that includes a share user-interactive graphical user interface object allows a user to quickly recognize that information included in the clinical record user interface can be shared, thereby providing improved visual feedback to the user. Generating a file containing information related to the clinical record and displaying a share user interface for sharing the file with a recipient in response to detecting the set of one or more user inputs reduces the number of inputs needed to perform an operation (e.g., to generate a file containing clinical record information and share the file).

In some embodiments, the computer system (e.g., 600) detects, via the one or more input devices, a set of one or more user inputs (e.g., a tap input) that includes an input (e.g., 850c) corresponding to selection of the share user-interactive graphical user interface object (e.g., 818). In some embodiments, in response to detecting the set of one or more user inputs, the computer system generates a file (e.g., a .pdf, a .doc, a jpg) containing information related to the first clinical record and displays, via the display generation component (e.g., 602), a share user interface (e.g., 824) for sharing the file (e.g., 826) with a recipient. In some embodiments, the share user interface includes options for selecting a recipient to send the file to and/or options for sending the file via various means (e.g., a messaging application, an email application).

In some embodiments, the computer system (e.g., 600) displays a summary user interface (e.g., 804), wherein displaying the summary user interface includes concurrently displaying a first user-interactive graphical user interface object (e.g., 810) for displaying information corresponding to a second signed clinical record, and a second user-interactive graphical user interface object (e.g., 812) for displaying information corresponding to a second unsigned clinical record. In some embodiments, the first user-interactive graphical user interface object is different from the second user-interactive graphical user interface object. Displaying a summary user interface that includes a user-interactive graphical user interface object for displaying information corresponding to a signed clinical record and a user-interactive graphical user interface object for displaying information corresponding to an unsigned clinical record reduces the number of inputs required to perform an operation (e.g., to view signed and unsigned clinical records by eliminating the need to switch between different user interfaces for displaying signed and unsigned clinical records).

In some embodiments, displaying the verification user interface (e.g., 840) includes displaying a visual indication (e.g., 848) (e.g., a graphical indication, a textual indication) corresponding to a geographical location (e.g., a vaccination site, a doctor's office, a lab facility) corresponding to the first clinical record that was not included in the clinical record user interface. Displaying the verification user interface with a visual indication corresponding to a geographical location corresponding to the clinical record allows the user to quickly recognize that the clinical record corresponds to the visually indicated geographical location, thereby providing improved visual feedback to the user.

In some embodiments, displaying the verification user interface (e.g., 840) includes displaying a second visual indication (e.g., 852) (e.g., a graphical indication, a textual indication) corresponding to a second geographical location (e.g., a home address) corresponding to a patient (e.g., the person on whom a lab was performed) associated with the first clinical record that was not included in the clinical record user interface. Displaying the verification user interface with a visual indication corresponding to a geographical location corresponding to a patient allows the user to quickly recognize that the clinical record corresponds to the visually indicated geographical location corresponding to the patient, thereby providing improved visual feedback to the user.

Note that details of the processes described above with respect to method 900 (e.g., FIG. 9) are also applicable in an analogous manner to the methods described below. For example, method 1100 optionally includes one or more of the characteristics of the various methods described above with reference to method 900. For example, a signed vision prescription could be displayed concurrently with an unsigned vision prescription, wherein the signed vision prescription is displayed with a verification identifier as described above with reference to method 900. For brevity, these details are not repeated below.

FIGS. 10A-10O illustrate exemplary user interfaces for adding a vision prescription to a computer system, in accordance with some embodiments. The user interfaces in these figures are used to illustrate the processes described below, including the processes in FIG. 11.

In FIG. 10A, computer system 600 displays third-party user interface 1004, which is a third-party website (e.g., a website associated with an ophthalmologist) that allows a user to download a vision prescription. Third-party user interface 1004 includes prescription 1008 that includes information corresponding to a vision prescription, and save affordance 1006 that, when selected, initiates a process for adding (e.g., saving) the vision prescription. At FIG. 10A, computer system 600 receives input 1050a (e.g., a tap input) on save affordance 1006.

Figure 10B:
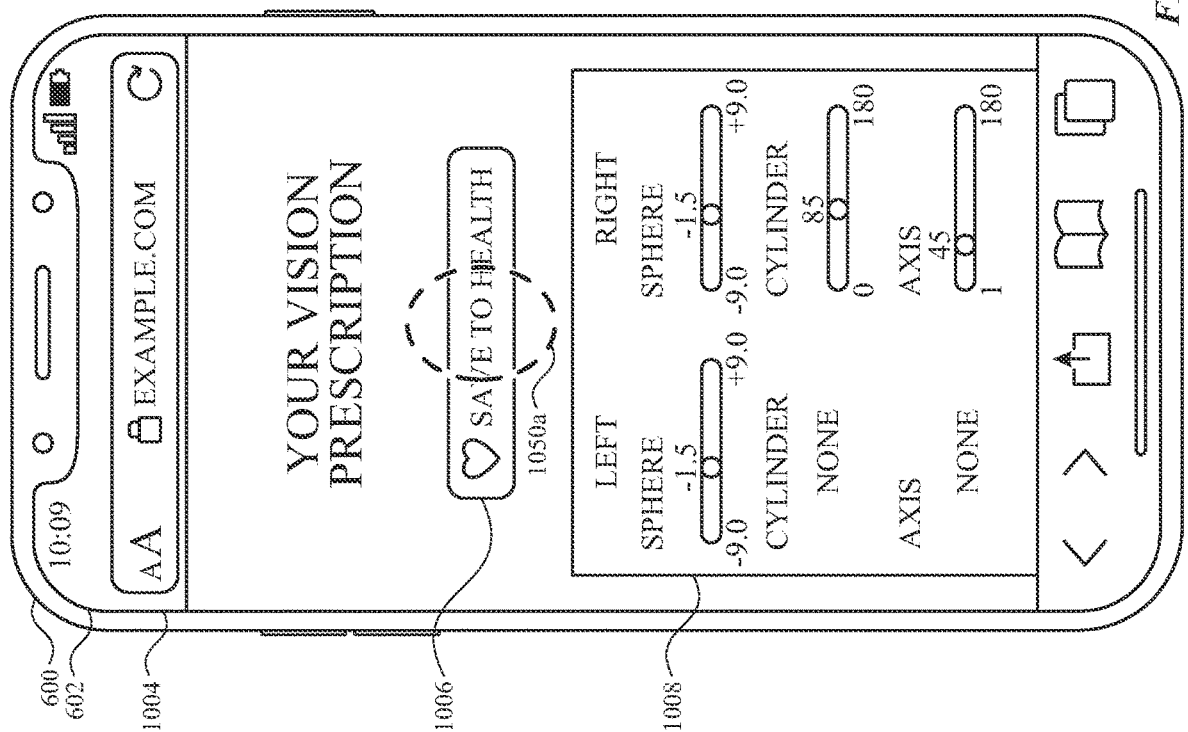

In FIG. 10B, in response to receiving input 1050a, computer system 600 displays add sheet user interface 1010. Add sheet user interface 1010 is a user interface for proceeding with the process for adding the vision prescription. Add sheet user interface 1010 includes add to health affordance 1016 which, when selected, causes computer system 600 to add the prescription (e.g., to download the prescription and/or associate it with a health application installed on computer system 600). Add sheet user interface 1010 further includes do not add affordance 1018 which, when selected, causes computer system 600 to return to displaying third-party user interface 1004 without displaying sheet user interface 1010 without saving the prescription. In FIG. 10B, computer system 600 receives input 1050b (e.g., a tap input) on add to health affordance 1016.

Add sheet user interface 1010 overlays third-party user interface 1004 such that at least a portion of third-party user interface is displayed concurrently while add-sheet user interface 1010 is displayed. Add sheet user interface 1010 further includes icon 1012 that includes a visual representation of a health application on computer system in which the saved prescription can be viewed and/or managed. Add sheet user interface 1010 further includes prescription 1014 that, like prescription 1008, includes information corresponding to the vision prescription.

Figure 10C:
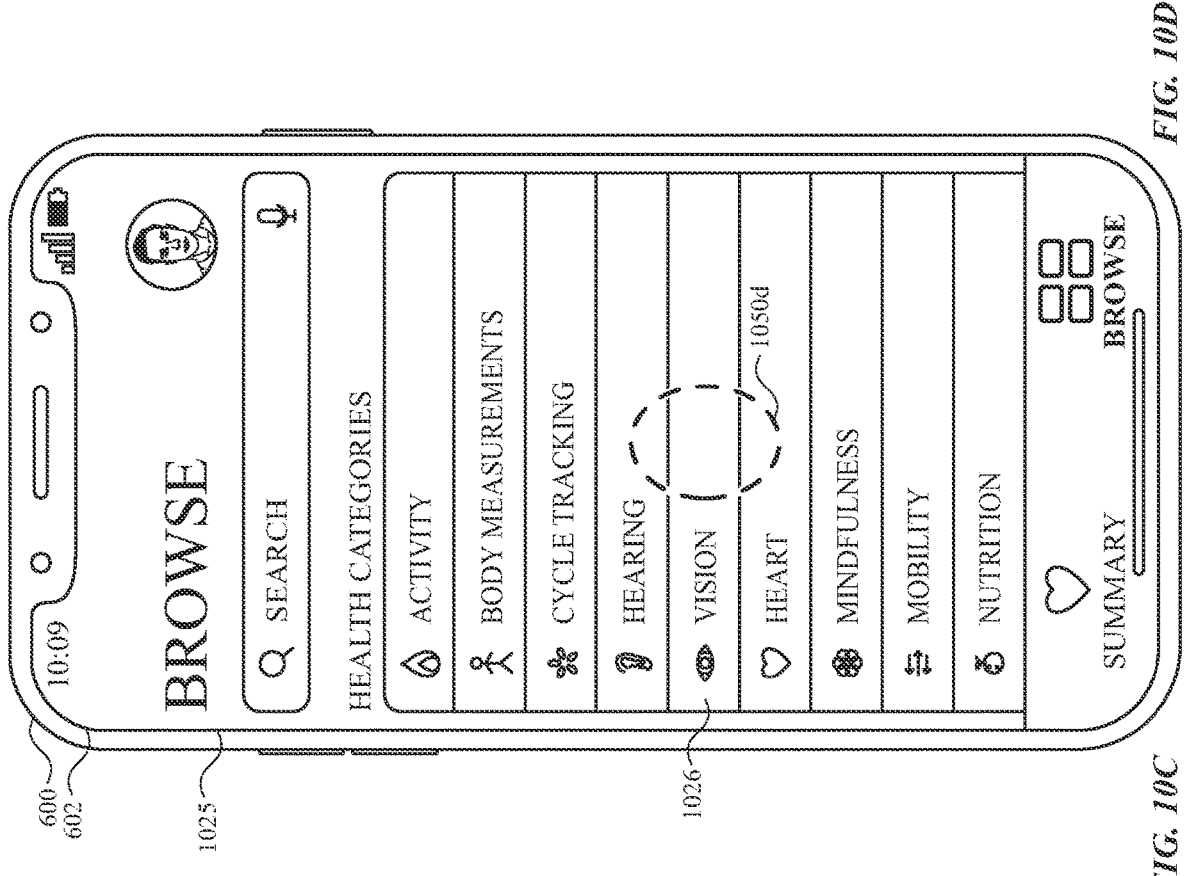

In FIG. 10C, after receiving tap input 1050b, computer system displays home screen user interface 1022. Home screen user interface 1022 includes icons corresponding to various applications available on computer system 600, including icon 1024, which corresponds to a health application with which the saved prescription can be viewed and/or managed. In FIG. 10C, computer system 600 receives input 1050c (e.g., a tap input) on icon 1024 and, in response, opens (e.g., launches) the health application.

Figure 10D:
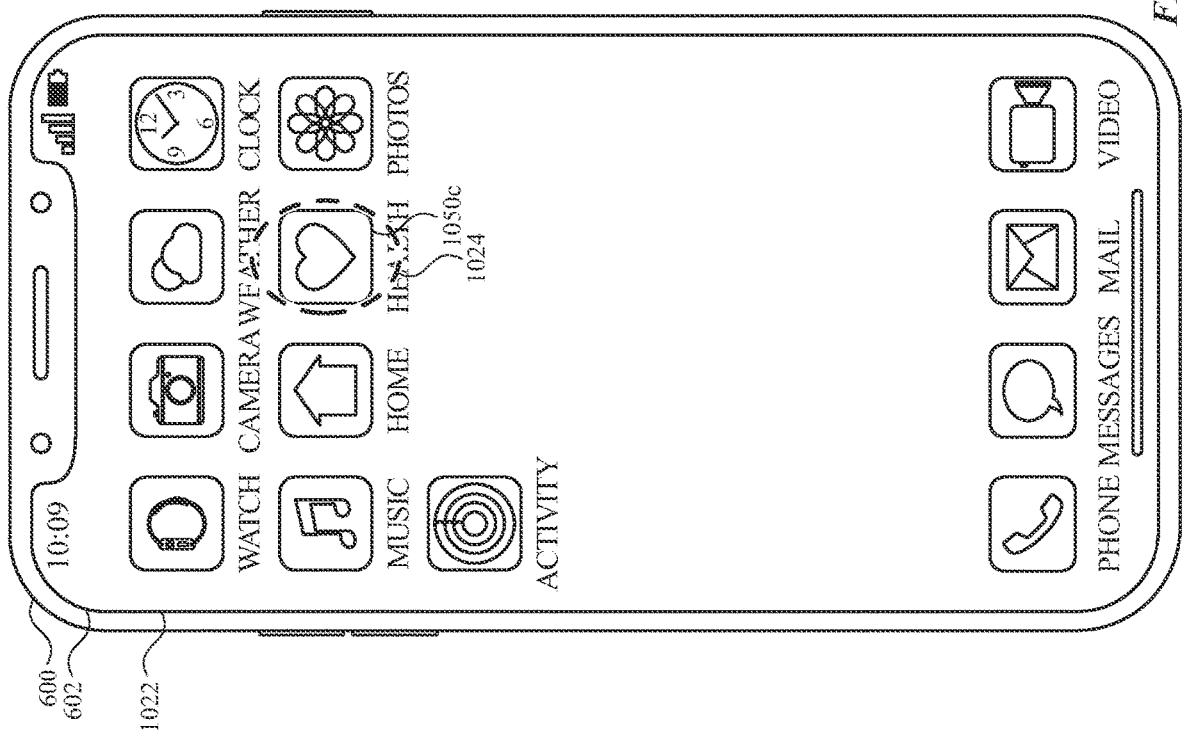

In FIG. 10D, after receiving input 1050c, computer system 600 displays health user interface 1025. Health user interface 1025 includes affordances corresponding to various clinical, physiological, and/or health-related topics that can be selected, including vision affordance 1026 which, when selected, causes computer system 600 to display information related to vision (e.g., vision prescriptions). In FIG. 10D, computer system 600 receives input 1050d (e.g., a tap input) on vision affordance 1026.

Figure 10E:
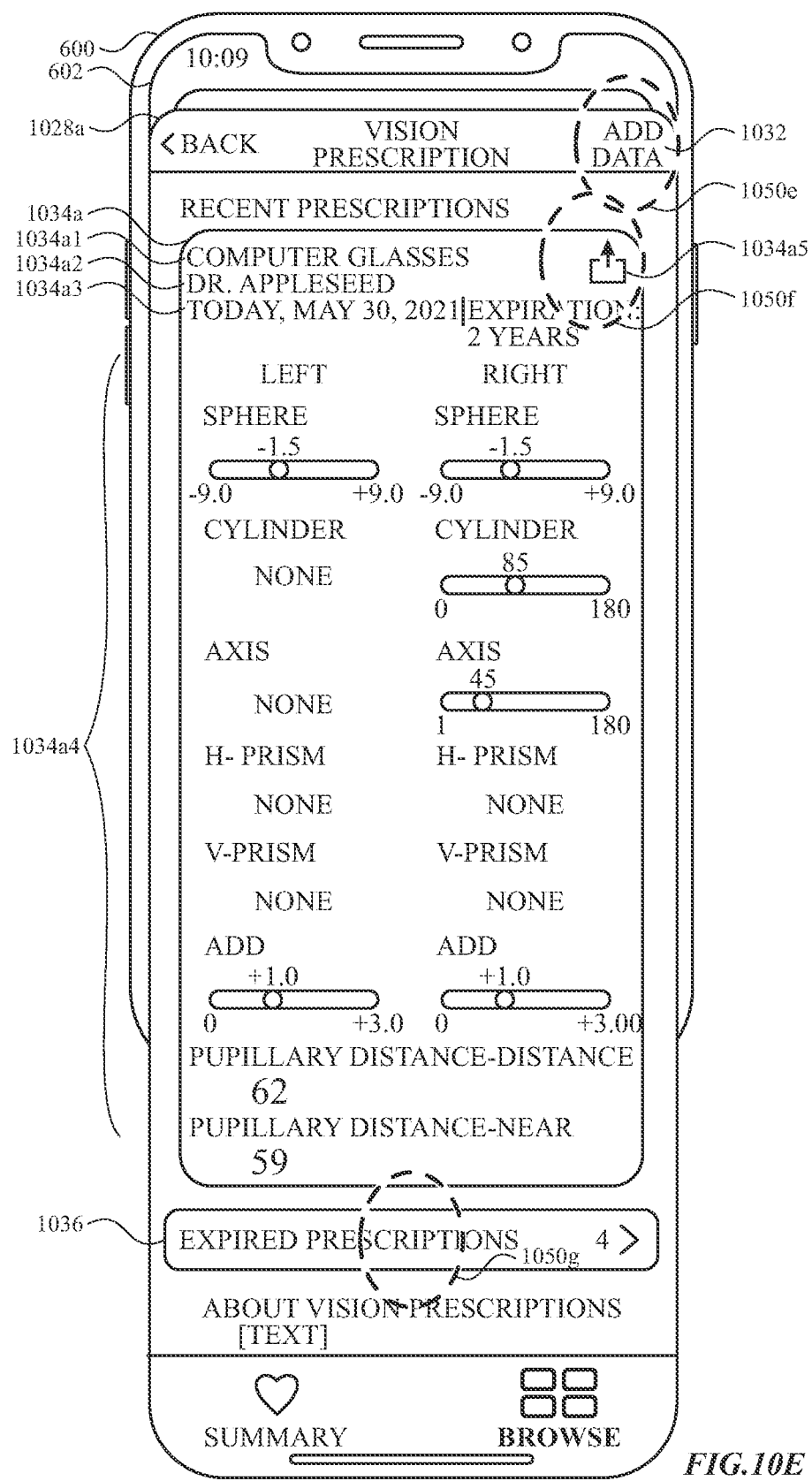

In FIG. 10E, after receiving input 1050d, computer system 600 displays active prescriptions user interface 1028a. Active prescriptions user interface 1028a includes information related to an active vision prescription (e.g., a vision prescription that is not expired). In some embodiments, a vision prescription expires after a threshold period of time (e.g., 2 years after the prescription is written/dated). In some embodiments, computer system 600 displays prescriptions in active prescriptions user interface 1028a based on a determination that they are not expired.

Active prescriptions user interface 1028a provides a user with several options for viewing and managing vision prescription information. Active prescriptions user interface 1028a includes add data affordance 1032 which, when selected, initiates a process for creating a new vision prescription entry (e.g., by entering information related to a vision prescription). In FIG. 10E, computer system 600 receives input 1050e (e.g., a tap input) and, in response, initiates the process for creating a new vision prescription entry as discussed below with reference to FIG. 10F.

Active prescriptions user interface 1028a further includes active prescription 1034a, which corresponds to the active prescription that was added as discussed above with reference to FIGS. 10A-10B. Active prescription 1034a includes various details of the prescription, including prescription type 1034a1 that indicates the type of vision prescription (e.g., glasses, contacts, computer glasses), 1034a2 that indicates the doctor who wrote the vision prescription, 1034a3 that includes timing information related to the vision prescription (e.g., the date the prescription was written, the amount of time remaining until the vision prescription will expire), and prescription details 1034a4 that includes various physiological measurements related to the vision prescription. Active prescription 1034a further includes share affordance 1034a5 which, when selected, initiates a process for sharing active prescription 1034a with a recipient (e.g., a recipient device). In FIG. 10E, computer system 600 receives input 1050f (e.g., a tap input) on share affordance 1034a5 and, in response, displays sharing user interface 1082 as discussed below with reference to FIG. 10O. Active prescriptions user interface 1028a further includes expired prescriptions affordance 1036 which, when selected, causes computer system 600 to display a user interface for viewing and/or managing expired vision prescriptions. In FIG. 10E, computer system 600 also receives input 1050g (e.g., a tap input) on expired prescriptions affordance 1036 and, in response, displays expired prescriptions user interface 1077, as discussed below with respect to FIG. 10N.

Figure 10F:
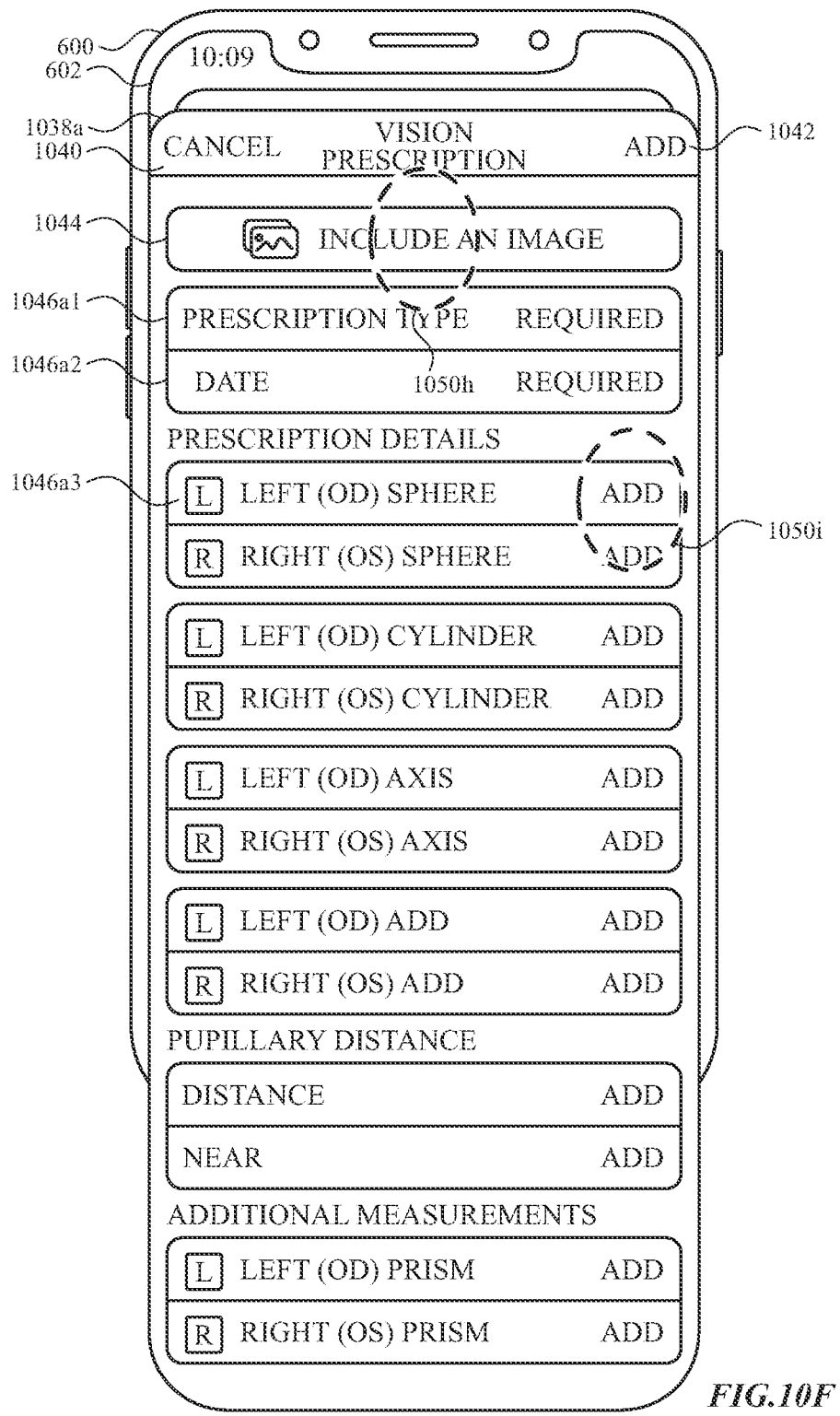

In FIG. 10F, in response to receiving input 1050e on add data affordance 1032 of FIG. 10E, computer system 600 displays add prescription user interface 1038a. Add prescription user interface 1038a is a user interface for creating and/or adding a new vision prescription by entering information related to a vision prescription. Add prescription user interface 1038a includes multiple options for adding various pieces of information related to a vision prescription. In particular, add prescription user interface 1038a includes add image affordance 1044 which, when selected, initiates a process for adding an image (e.g., a photo) related to a vision prescription (e.g., a photo of a physical vision prescription). In FIG. 10F, computer system 600 receives input 1050h (e.g., a tap input) on add image affordance 1044 and, in response, displays options for adding the image as discussed below with reference to FIG. 10I.

Add prescription user interface 1038a further includes prescription type 1046a1 which, when selected, causes computer system 600 to initiate a process for selecting a type of vision prescription (e.g., glasses, contacts, computer glasses). Add prescription user interface 1038a further includes date 1046a2 which, when selected, causes computer system 600 to initiate a process for selecting a date associated with the vision prescription (e.g., the date on which the vision prescription was written).

Add prescription user interface 1038a further includes various options for manually entering details of the vision prescription, such as the prescription detail 1046a3, which corresponds to the Left (OD) Sphere aspect of a vision prescription. In FIG. 10F, computer system 600 receives input 1050i (e.g., a tap input) on prescription detail 1046a3 and, in response, displays options for entering the prescription information corresponding to prescription detail 1046a3 as described below with reference to FIG. 10G.

Add prescription user interface 1038a further includes cancel affordance 1040 which, when selected, cancels the process for adding a vision prescription and causes computer system 600 to return to displaying active prescriptions user interface 1028a, as illustrated in FIG. 10E. Add prescription user interface 1038a further includes add affordance 1042 which, when selected, causes computer system 600 to add a vision prescription with the information that has been added for the corresponding vision prescription as reflected in add prescription user interface 1038a at the time that add affordance 1042 is selected.

In FIG. 10G, in response to receiving input 1050i on prescription detail 1046a3 in FIG. 10F, computer system 600 displays entry user interface 1055a, which includes options for manually entering the one or more values corresponding to prescription detail 1046a3. In particular, entry user interface 1055a includes detail 1054a which, when selected, allows a user to edit the date on which the corresponding prescription detail was received, detail 1054b which, when selected, allows a user to edit the time at which the corresponding prescription detail was received, and detail 1054c which, when selected, allows a user to edit the value (e.g., the physiological measurement) associated with the corresponding prescription detail.

Entry user interface 1055a further includes cancel affordance 1048 which, when selected, cancels the process for entering the selected prescription detail and causes computer system 600 to return to displaying add prescription user interface 1038a. Entry user interface 1055a further includes add affordance 1052 which, when selected, submits the currently entered prescription details reflected in entry user interface 1055a and causes computer system 600 to return to displaying add prescription user interface 1038a with the relevant prescription detail updated accordingly.

Entry user interface 1055a further includes keypad 1056, which provides options for manually entering details corresponding to the selected prescription detail. In some embodiments, keypad 1056 is updated based on the relevant entry details of a selected prescription detail. For example, keypad 1056 includes numbers as illustrated in FIGS. 10G-10H when a prescription detail with strictly numerical values is selected for entry (e.g., detail 1054*a*3, as illustrated in FIGS. 10G-10H), and includes alphanumerical options (e.g., a full touch QWERTY keyboard) when the selected prescription detail may include numbers and letters.

FIG. 10H illustrates entry user interface 1055*b*, wherein detail 1054*b*3 has been updated to have a value of 100 and add affordance 1052 has been grayed out to indicate that it is not currently selectable. In some embodiments, when entering prescription details, the values entered by a user are checked to avoid erroneous entries. In some examples, in accordance with a determination that a user has entered an erroneous prescription detail (e.g., a physiological measurement outside of a possible range of values, a physically impossible value and/or set of values), the add affordance 1052 is displayed as grayed out and is not selectable until the error is addressed.

In FIG. 10I, in response to receiving input 1050*h* on add image affordance 1044 of FIG. 10F, computer system 600 displays options for selecting a method of adding an image to a prescription. As illustrated in FIG. 10I, computer system 600 displays the options for adding the image overlaid on add prescription user interface 1038*b*, which is an updated version of add prescription user interface 1038*a*. In some embodiments, elements included in add prescription user interface 1038*b* other than the affordance for selecting a method of adding the image are displayed as grayed out or with a shadow visual effect to emphasize the selectable options corresponding to methods of adding the image.

Add prescription user interface 1038*b* includes choose photo affordance 1058*a* which, when selected, causes computer system 600 to display a user interface for selecting an existing media item (e.g., a photo) to be added to the prescription being created as described below with respect to FIG. 10J. In FIG. 10I, computer system 600 receives input 1050*i* (e.g., a tap input) on choose photo affordance 1058*a* and, in response, displays a photo picker user interface as illustrated in FIG. 10J. Add prescription user interface 1038*b* further includes take photo affordance 1058*b* and scan document affordance 1058*c* which, when selected, cause computer system 600 to open (e.g., launch) a camera application available on computer system 600 to create and/or generate a new image (e.g., a photo) to be added to the prescription being created, as discussed below with reference to FIG. 10K. In FIG. 10I, computer system 600 receives input 1050*k* (e.g., a tap input) on take photo affordance 1058*b* and tap input 1050*l* (e.g., a tap input) on scan document affordance 1058*c* and, in response to receiving input 1050*k* or 1050*k*, displays a camera user interface as illustrated in FIG. 10K.

In FIG. 10J, in response to receiving input 1050*j*, computer system 600 displays photo picker user interface 1060, which illustrates a user interface for selecting an image to be added to the vision prescription. Photo picker user interface 1060 includes multiple selectable photo options, including preview image 1066 which corresponds to an image of a physical vision prescription. In FIG. 10J, computer system 600 receives input 1050*m* and, in response, selects preview image 1066 such that the corresponding image is selected to be added to the vision prescription. Photo picker user interface 1060 further includes add affordance 1064 which, when selected, adds images corresponding to the one or more selected preview images to the vision prescription. Photo picker user interface 1060 further includes cancel affordance 1062 which, when selected, dismisses the photo picker user interface and causes computer system 600 to return to displaying a previous user interface for adding the vision prescription (e.g., as illustrated in FIG. 10F or FIG. 10I).

Figure 10L:
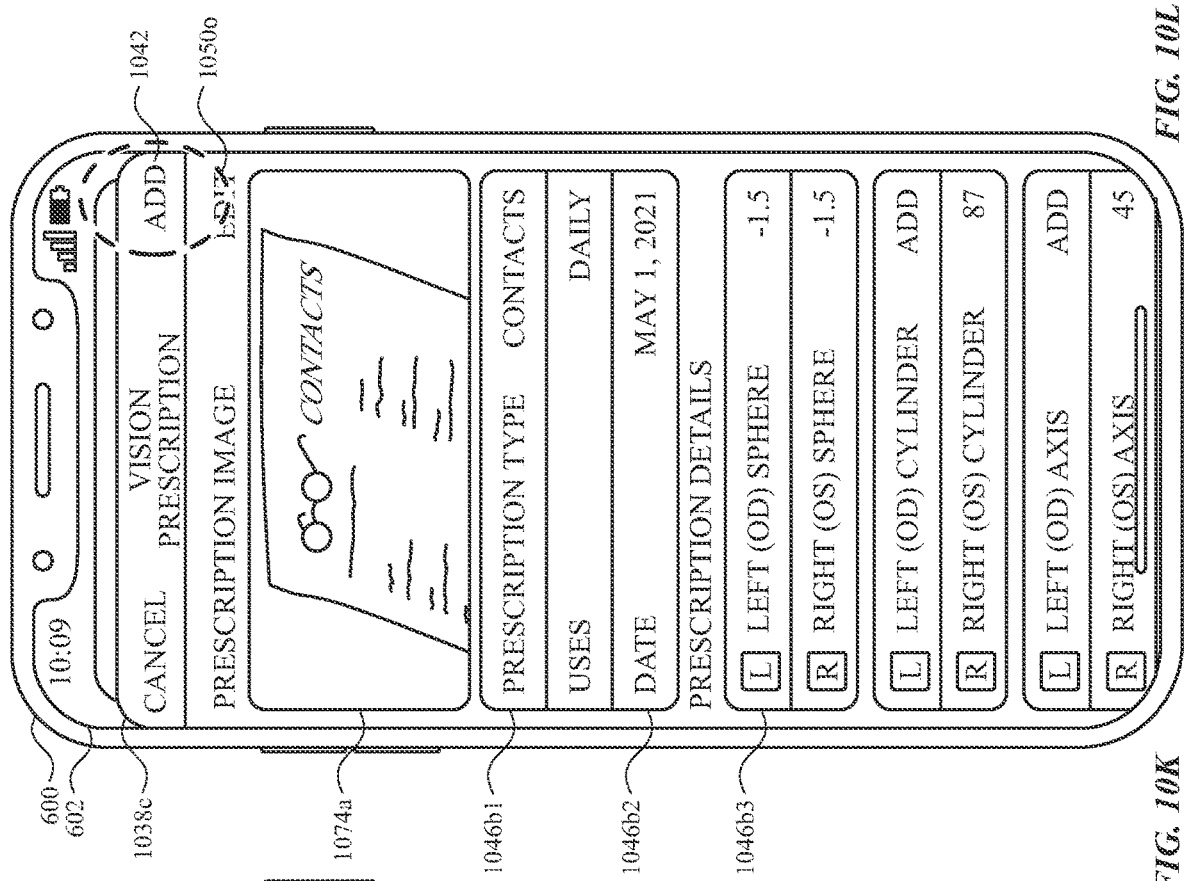
Figure 10K:
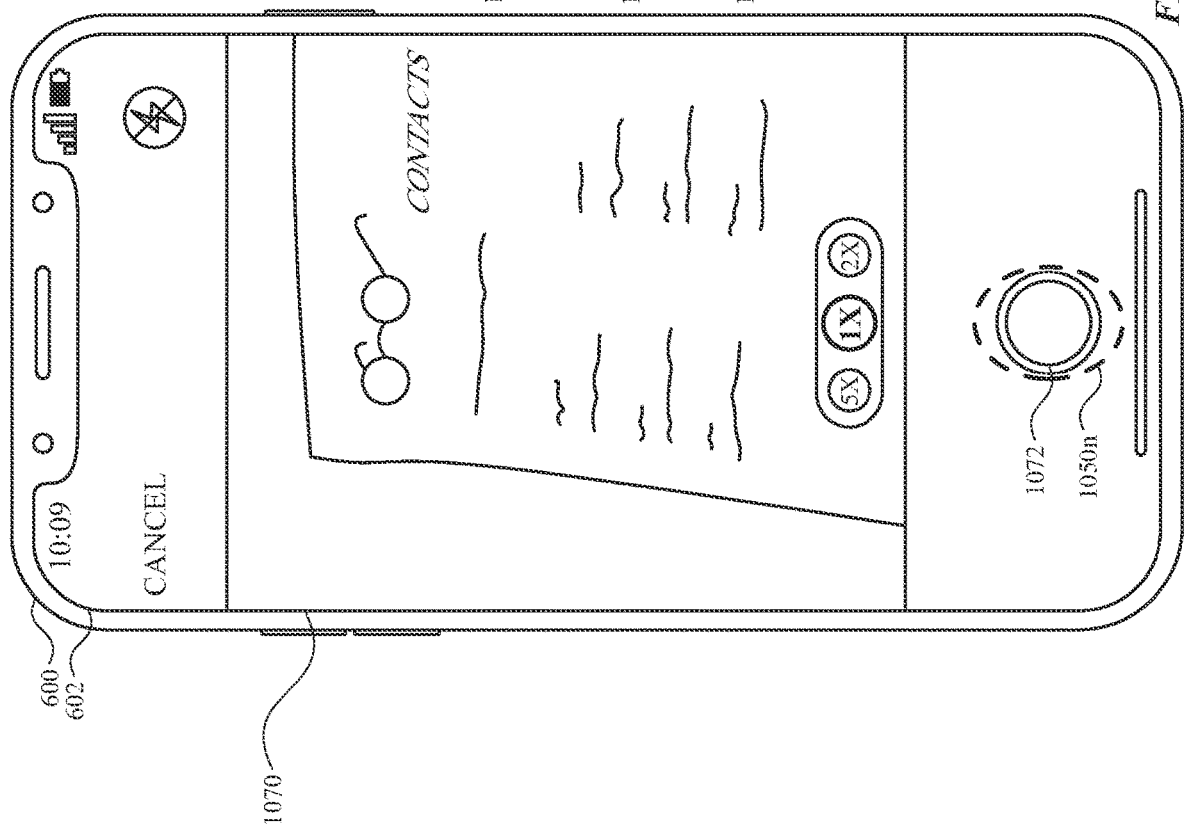
Figure 10O:
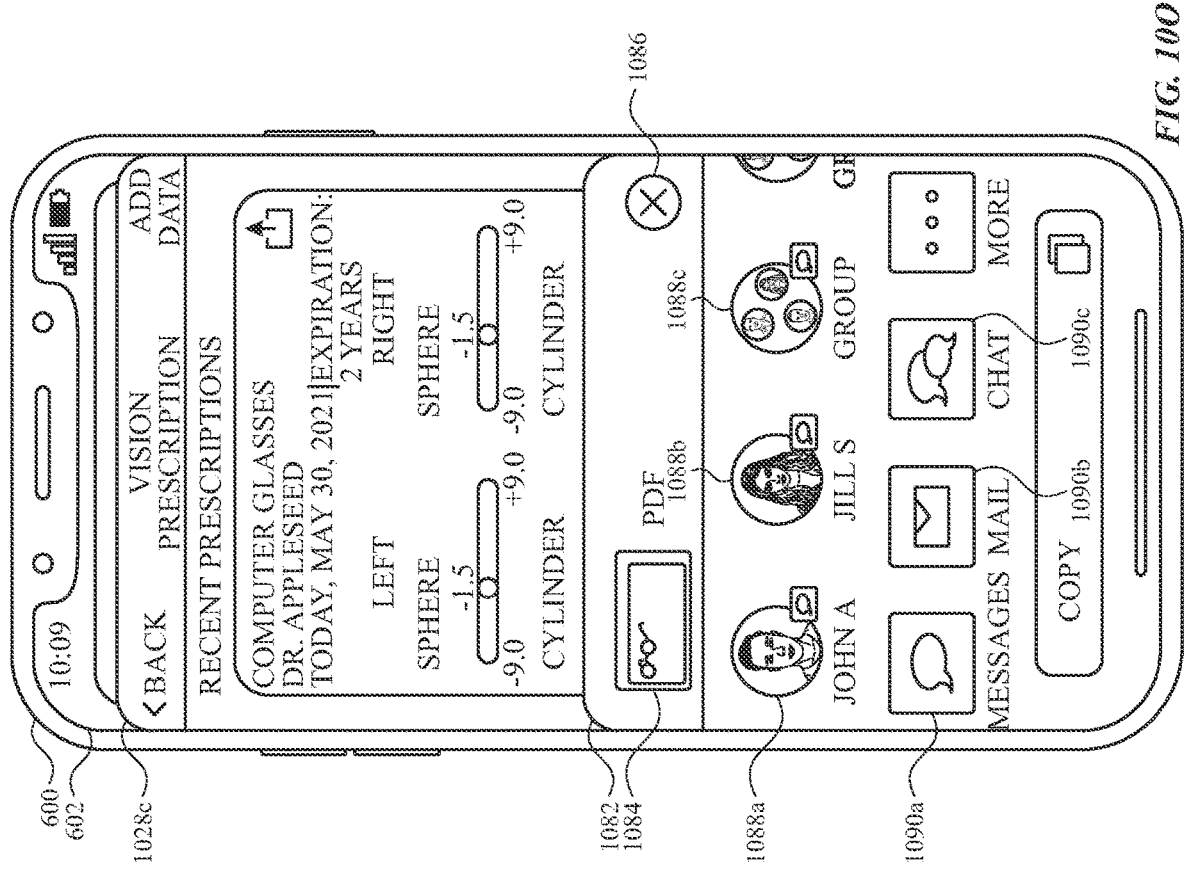

In FIG. 10K, in response to receiving input 1050*k* or 1050*l* in FIG. 10I, computer system 600 displays camera user interface 1070, which includes a representation of the field of view of a camera sensor and a capture affordance 1072 which, when selected, causes computer system 600 to take a photo. In FIG. 10K, computer system 600 receives input 1050*n* on capture affordance 1072 and, in response, takes a photo of a physical vision prescription and adds the photo to the vision prescription that is being created (e.g., as discussed above with reference to FIGS. 10F-10L). In some embodiments, in response to receiving input 1050*n*, computer system displays add prescription user interface 1038*c* as illustrated in FIG. 10L, which includes a representation of the photo taken in FIG. 10K. In some embodiments, in response to adding an image to the prescription, computer system analyzes the photo to automatically include values included in the in corresponding fields of the add prescription user interface 1038*c*. For example, in response to analyzing the photo and determining that the prescription contains a value for a physiological measurement, the computer system displays the value with the corresponding detail included in add prescription user interface 1038*c* without requiring a user to enter the corresponding value (e.g., manually).

In FIG. 10L, computer system 600 displays add prescription user interface 1038*c*, which is an updated version of add prescription user interface 1038*b* wherein the details of the vision prescription have been added and/or edited. Add prescription user interface 1038*c* includes detail 1046*b*1 indicating that the prescription is a contacts prescription, detail 1046*b*2 that includes a date associated with the vision prescription (e.g., a date on which the prescription was written), and detail 1046*b*3 that includes a value (e.g., for a physiological measurement) for the corresponding aspect of the vision prescription (e.g., the left (OD) sphere). Add prescription user interface further includes preview image 1074*a* that includes at least a partial view of an image (e.g., a photo) associated with the prescription being added.

Add prescription user interface 1038*c* further includes add affordance 1042 which, when selected, adds a prescription with the prescription details entered as described above. In some embodiments, in response to an input on add affordance 1042, computer system 600 determines whether the newly added prescription meets active prescription criteria (e.g., whether the prescription is expired) and, based on the determination, adds the prescription to either an active prescriptions user interface (e.g., as illustrated in FIG. 10E) or an expired prescriptions user interface (e.g., as illustrated in FIG. 10N). In FIG. 10L, computer system 600 receives input 1050*o* (e.g., a tap input) on add affordance 1042 and, in response, adds the prescription with the prescription details reflected in add prescription user interface 1038*c*.

In FIG. 10M, in response to receiving input 1050*o*, computer system 600 displays active prescriptions user interface 1028*b*, which is an updated version of active prescriptions user interface 1028*a* that now includes the prescription added (as discussed above with reference to FIG. 10L). Active prescriptions user interface includes active prescription 1076, which includes the details of the added prescription, including the physiological measurement values shown in FIG. 10L. Active prescriptions user interface further includes preview image 1074*b*, which, like preview image 1074*a*, includes at least a partial view of an image associated with active prescription 1076. Active prescriptions user interface 1028 further includes active prescription 1034b, which corresponds to at least a partial view of active prescription 1034a that has been repositioned within the active prescriptions user interface based on the addition of active prescription 1076.

In FIG. 10N, in response to receiving input 1050g (e.g., a tap input) on expired prescriptions affordance 1036, computer system 600 displays expired prescriptions user interface 1077. Expired prescriptions user interface 1077 includes expired prescription 1080a that includes details of an expired vision prescription (e.g., physiological measurements, prescription type, the date on which the prescription was written) and expired prescription 1080b that includes details similar to expired prescription 1080a but for a different vision prescription. In some embodiments, expired vision prescriptions are automatically displayed in expired prescriptions user interface 1077 as opposed to an active prescriptions user interface 1028b based on a determination that the prescriptions are expired (e.g., that a threshold period of time (e.g., 1 year, 18 months, 2 years) has passed since the date on which the prescription was written). Expires prescriptions user interface 1077 further includes back affordance 1078 which, when selected, causes computer system 600 to return to displaying active prescriptions user interface 1028a, as illustrated in FIG. 10E.

In FIG. 10O, in response to receiving input 1050f on share affordance 1034a5, computer system 600 displays sharing user interface 1082 overlaid on active prescriptions user interface 1028c such that at least a portion of active prescriptions user interface 1028c is displayed concurrently with sharing user interface 1082. Displaying sharing user interface 1082 corresponds to initiating a process for sharing active prescription 1034a with a recipient. In response to receiving input 1050f, computer system 600 generates a file (e.g., a .pdf, a .jpg) containing information corresponding to active prescription 1034a. Sharing user interface 1082 includes preview image 1084, which corresponds to a preview of the file.

Sharing user interface 1082 includes options for sharing the file with one or more recipients (e.g., a recipient device) via various means. Sharing user interface includes recipient affordance 1088a which, when selected, initiates a process for sharing the file with a first recipient, recipient affordance 1088b which, when selected, initiates a process for sharing the file with a second recipient different from the first recipient, and recipients affordance 1088c which, when selected, initiates a process for sharing the file with a multiple recipients. Sharing user interface 1082 further includes send method affordance 1090a which, when selected, initiates a process for transmitting the file to a recipient using a first means of communication (e.g., a messaging application). Sharing user interface 1082 further includes send method affordance 1090b which, when selected, initiates a process for transmitting the file to a recipient using a second means of communication different from the first means of communication (e.g., an email application). Sharing user interface 1082 further includes send method affordance 1090c which, when selected, initiates a process for transmitting the file to a recipient using a third means of communication different from the first means of communication and the second means of communication (e.g., a chat application). Sharing user interface 1082 further includes dismiss affordance 1086 which, when selected, causes computer system 600 to return to displaying active prescriptions user interface 1028c without displaying sharing user interface 1082.

FIG. 11 is a flow diagram illustrating a method for adding a vision prescription to a computer system (e.g., a smartphone, a smartwatch, a wearable electronic device, a desktop computer, a laptop, a tablet) in accordance with some embodiments. Method 1100 is performed at a computer system (e.g., 100, 300, 500) that is in communication with a display generation component and one or more input devices (e.g., a mouse, a keyboard, a touch-sensitive surface). Some operations in method 1100 are, optionally, combined, the orders of some operations are, optionally, changed, and some operations are, optionally, omitted.

As described below, method 1100 provides an intuitive way for adding a vision prescription to a computer system. The method reduces the cognitive burden on a user for adding a vision prescription to a computer system, thereby creating a more efficient human-machine interface. For battery-operated computing devices, enabling a user to add a vision prescription to a computer system faster and more efficiently conserves power and increases the time between battery charges.

The computer system (e.g., 600) displays (1102), via the display generation component (e.g., 602), an active prescriptions user interface (e.g. 1028a), wherein the active prescriptions user interface includes: first information corresponding to one or more prescriptions (1104) (e.g., glasses prescriptions, contacts prescriptions) that satisfy a set of active prescription criteria (e.g., the prescriptions are from within a threshold time period) and an expired prescriptions user-interactive graphical user interface object (e.g., 1036) (1106).

The computer system (e.g., 600) receives (1108), via the one or more input devices, a user input (e.g., 1050g) that corresponds to selection (e.g., a tap gesture, a swipe, a press input, and/or a mouse click) of the expired prescriptions user-interactive graphical user interface object (e.g., 1036).

In response to receiving the user input (e.g., 1050g) that corresponds to selection of the expired prescriptions user-interactive graphical user interface object (1036), the computer system (e.g., 600) displays (1110) an expired prescriptions user interface (e.g., 1077), wherein the expired prescriptions user interface includes second information corresponding to one or more prescriptions that do not satisfy the set of active prescription criteria (e.g., the prescriptions are from outside of a threshold time period). In some embodiments, the first information corresponding to the one or more prescriptions that satisfy the set of active prescription criteria is not included in the expired prescriptions user interface. In some embodiments, the second information corresponding to the one or more prescriptions that do not satisfy the set of active prescription criteria is not included in the active prescriptions user interface. Transitioning from displaying an active prescriptions user interface to displaying an expired prescriptions user interface in response to an input corresponding to selection of an expired prescriptions user-interactive graphical user interface object reduces the number of inputs needed to perform an operation (e.g., to transition from the active prescriptions user interface to the expired prescriptions user interface).

In some embodiments, the set of active prescription criteria includes a criterion that is satisfied when a respective prescription satisfies a time range requirement (e.g., the prescription is dated less than 5 years ago, 3 years ago, 2 years ago, 1 year ago; the prescription falls within a defined date range). Displaying an active prescriptions user interface (e.g., 1028a) that includes information corresponding to one or more prescriptions that satisfy a set of active prescription criteria, wherein the set of active prescriptions criteria includes a criterion that is satisfied when a respective prescription satisfies a time range requirement, enables a user to view an active prescriptions user interface that includes information corresponding to prescriptions that satisfy the time range requirement without requiring the user to add/remove prescriptions that do not satisfy the time range requirement, which performs an operation when a set of conditions has been met without requiring further user input.

In some embodiments, the first information corresponding to one or more prescriptions that satisfy a set of active prescription criteria includes, in accordance with a determination that a first prescription of the one or more prescriptions that satisfy a set of active prescription criteria has a corresponding stored image (e.g., 1074b) (e.g., a picture of a prescription), a representation of the corresponding stored image). Conditionally displaying a representation of a stored image based on a determination about whether or not a first prescription that satisfies a set of active prescription criteria has a corresponding stored image enables a user to view the representation of the stored image without requiring the user to select the first prescription to view the representation of the image, or to determine whether the first prescription has a corresponding stored image to view the image, which performs an operation when a set of conditions has been met without requiring further user input.

In some embodiments, the first information corresponding to one or more prescriptions that satisfy a set of active prescription criteria includes, in accordance with a determination that a second prescription of the one or more prescriptions that satisfy a set of active prescription criteria has a set of corresponding source data (e.g., a corresponding doctor's office, doctor's name, date on which the prescription was written), a representation of the set of corresponding source data (e.g., 1034a2). Conditionally displaying a representation of a set of corresponding source data based on a determination about whether or not a second prescription that satisfies a set of active prescription criteria has a corresponding set of source data enables a user to view the representation of the source data without requiring the user to select the second prescription to view the representation of the source data, or to determine whether the second prescription has corresponding source data to view the source data, which performs an operation when a set of conditions has been met without requiring further user input.

In some embodiments, the active prescriptions user interface (e.g., 1028a) includes an add user-interactive graphical user interface object (e.g., 1032). In some embodiments, the computer system (e.g., 600) detects, via the one or more input devices, a user input (e.g., 1050e) corresponding to selection of the add user-interactive graphical user interface object. In some embodiments, in response to detecting selection of the add user-interactive graphical user interface object, the computer system displays a prescription creation user interface (e.g., 1038a) including one or more user-interactive graphical user interface objects for entering information (e.g., via inputs on a virtual keyboard, via voice inputs) corresponding to a new prescription. Displaying a prescription creation user interface including user-interactive graphical user interface objects for entering information corresponding to a new prescription in response to detecting selection of an add user-interactive graphical user interface object reduces the number of inputs needed to perform an operation (e.g., to transition from a user interface for viewing active prescriptions to a user interface for creating a new prescription).

In some embodiments, the prescription creation user interface (e.g., 1038a) includes a first eye user-interactive graphical user interface object (e.g., 1046a3) that, when selected, initiates a process for entering information corresponding to a first eye (e.g., a left eye), and a second eye user-interactive graphical user interface object that, when selected, initiates a process for entering information corresponding to a second eye different from the first eye (e.g., a right eye). Displaying a creation user interface that includes a first eye user-interactive graphical user interface object that, when selected, causes options for entering information corresponding to a first eye and a second eye user-interactive graphical user interface object that, when selected, causes options for entering information corresponding to a second eye different from the first eye reduces the number of inputs required to perform an operation (e.g., to create a new vision prescription that includes information for two different eyes).

In some embodiments, the prescription creation user interface (e.g., 1038a) includes an add photo user-interactive graphical user interface object (e.g., 1044). In some embodiments, the computer system (e.g., 600) detects, via the one or more input devices, a user input (e.g., 1050h) (e.g., a tap input) corresponding to selection of the add photo user-interactive graphical user interface object. In some embodiments, in response to detecting the user input corresponding to selection of the add photo user-interactive graphical user interface object, the computer system concurrently displays: a user-interactive graphical user interface object for adding a previously captured photo (e.g., 1058a) (e.g., by selecting the previously captured photo from a photo album), and a user-interactive graphical user interface object for adding a new photo (e.g., 1058b, 1058c) by capturing a new image via a camera sensor. In some embodiments, the computer system is in communication with a camera sensor. In some embodiments, selecting the option for adding the photo by capturing the new photo via the camera sensor causes the computer system to open a camera application. In response to detecting a user input corresponding to selection of the add photo user-interactive graphical user interface object, concurrently displaying a user-interactive graphical user interface object for adding a previously captured photo and a user-interactive graphical user interface object for adding a new photo by capturing the new image via a camera sensor provides additional control options without cluttering the user interface.

In some embodiments, the prescription creation user interface (e.g., 1038a) includes a create user-interactive graphical user interface object (e.g., 1042). In some embodiments, the computer system (e.g., 600) receives, via the one or more input devices, a first sequence of one or more user inputs (e.g., 1050i) (e.g., touch inputs, rotational inputs, press inputs) corresponding to the entry of a prescription parameters. In some embodiments, after receiving the first sequence of one or more inputs, the computer system detects, via the one or more input devices, a user input (e.g., 1050o) (e.g., a tap input) corresponding to selection of the create user-interactive graphical user interface object. In some embodiments, in response to detecting the user input corresponding to selection of the create user-interactive graphical user interface object: in accordance with a determination that the prescription parameters contain at least one error, the computer system displays a visual indication that the prescription parameters contain at least one error (e.g., one or more of the entered values does not meet a set of valid data criteria (e.g., is physically impossible)), and in accordance with a determination that the prescription parameters do not contain at least one error, the computer system generates (e.g., creating) a third prescription (e.g., 1076) that is based on (e.g., at least partially) the prescription parameters. Conditionally creating a third prescription or displaying a visual indication that the prescription parameters contain at least one error in response to detecting a user input corresponding to selection of the create user-interactive graphical user interface object allows a user to quickly recognize whether the prescription parameters they entered contained errors, thereby providing improved visual feedback to the user.

In some embodiments, after generating the third prescription (e.g., 1076), the computer system (e.g., 600) displays a second instance of the active prescriptions user interface (e.g., 1028*b*) that includes, in accordance with a determination that the third prescription satisfies the set of active prescription criteria, information corresponding to the third prescription. In some embodiments, displaying the active prescriptions user interface, wherein the active prescriptions user interface includes prescription information corresponding to the prescription parameters includes displaying the active prescriptions user interface with a new third prescription created at least partially based on the prescription parameters. In some embodiments, after generating the third prescription, in accordance with a determination that the third prescription does not satisfy the set of active prescription criteria, the computer system forgoing displaying the information corresponding to the third prescription in the active prescriptions user interface. Conditionally displaying the third prescription in the active prescriptions user interface based on whether the third prescription satisfies the set of active prescription criteria provides the user with an active prescriptions user interface that includes prescriptions that satisfy the first set of criteria without the user having to manually add/remove prescriptions that do not satisfy the first set of criteria, which performs an operation when a set of conditions has been met without requiring further user input.

In some embodiments, the third prescription (e.g., 1076) does not satisfy the set of active prescription criteria. In some embodiments, after generating the third prescription and while displaying the active prescriptions user interface (e.g., 1028*a*), the computer system (e.g., 600) detects, via the one or more input devices, a user input (e.g., 1050*g*) (e.g., a tap input) corresponding to selection of the expired prescriptions user-interactive graphical user interface object (e.g., 1036). In some embodiments, in response to detecting the user input corresponding to selection of the expired prescriptions user-interactive graphical user interface object, the computer system displays the expired prescriptions user interface (e.g., 1077), wherein the expired prescriptions user interface includes the information corresponding to the third prescription (e.g., 1076). Displaying third prescription in the expired prescriptions user interface in response to detecting a user input corresponding to selection of the expired prescriptions user-interactive graphical user interface object reduces the number of inputs required to perform an operation (e.g., to view the third prescription in the expired prescriptions user interface).

In some embodiments, the active prescriptions user interface (e.g., 1028*a*) includes a share user-interactive graphical user interface object (e.g., 1034*a*5) that, when selected, initiates a process for sharing information corresponding to at least one of the one or more prescriptions that satisfy the set of active prescription criteria. In some embodiments, sharing the corresponding prescription information includes generating a file (e.g., 1084) containing the corresponding prescription information and transmitting the file to a recipient (e.g., a recipient's electronic device). Displaying an active prescriptions user interface, wherein the active prescriptions user interface includes a share user-interactive graphical user interface object allows a user to quickly recognize that prescriptions included in the active prescriptions user interface can be shared.

In some embodiments, the computer system (e.g., 600) detects, via the one or more input devices, a set of one or more user inputs (e.g., a tap input) that includes an input (e.g., 1050*f*) corresponding to selection of the share user-interactive graphical user interface object (e.g., 1034*a*5). In some embodiments, in response to detecting the set of one or more user inputs, the computer system generates a file (e.g., 1084) (e.g., a .pdf, a .doc, a .jpg) containing information corresponding to at least one of the one or more prescriptions that satisfy the set of active prescription criteria and the computer system displays, via the display generation component (e.g., 602), a share user interface (e.g., 1082) for sharing the file with a recipient. In some embodiments, the share user interface includes options for selecting a recipient (e.g., 1088*a*, 1088*b*) to send the file to and/or options for sending the file via various means (e.g., 1090*a*, 1090*b*, 1090*c*) (e.g., a messaging application, an email application). Generating a file containing information corresponding to at least one of the one or more prescriptions that satisfy the set of active prescription criteria and displaying a share user interface for sharing the file with a recipient in response to detecting a set of one or more user inputs reduces the number of inputs needed to perform an operation (e.g., to generate a file containing prescription information and share the file).

Note that details of the processes described above with respect to method 1100 (e.g., FIG. 11) are also applicable in an analogous manner to the methods described above. For example, method 1100 optionally includes one or more of the characteristics of the various methods described above with reference to method 900. For example, a vision prescription could be a signed clinical record that is displayed concurrently with an affordance for viewing additional signed clinical records as described above with reference to method 900. For brevity, these details are not repeated below.

FIGS. 12A-12J illustrate exemplary user interfaces for adding clinical records to applications, in accordance with some embodiments. The user interfaces in these figures are used to illustrate the processes described below, including the processes in FIG. 13.

Figure 12B:
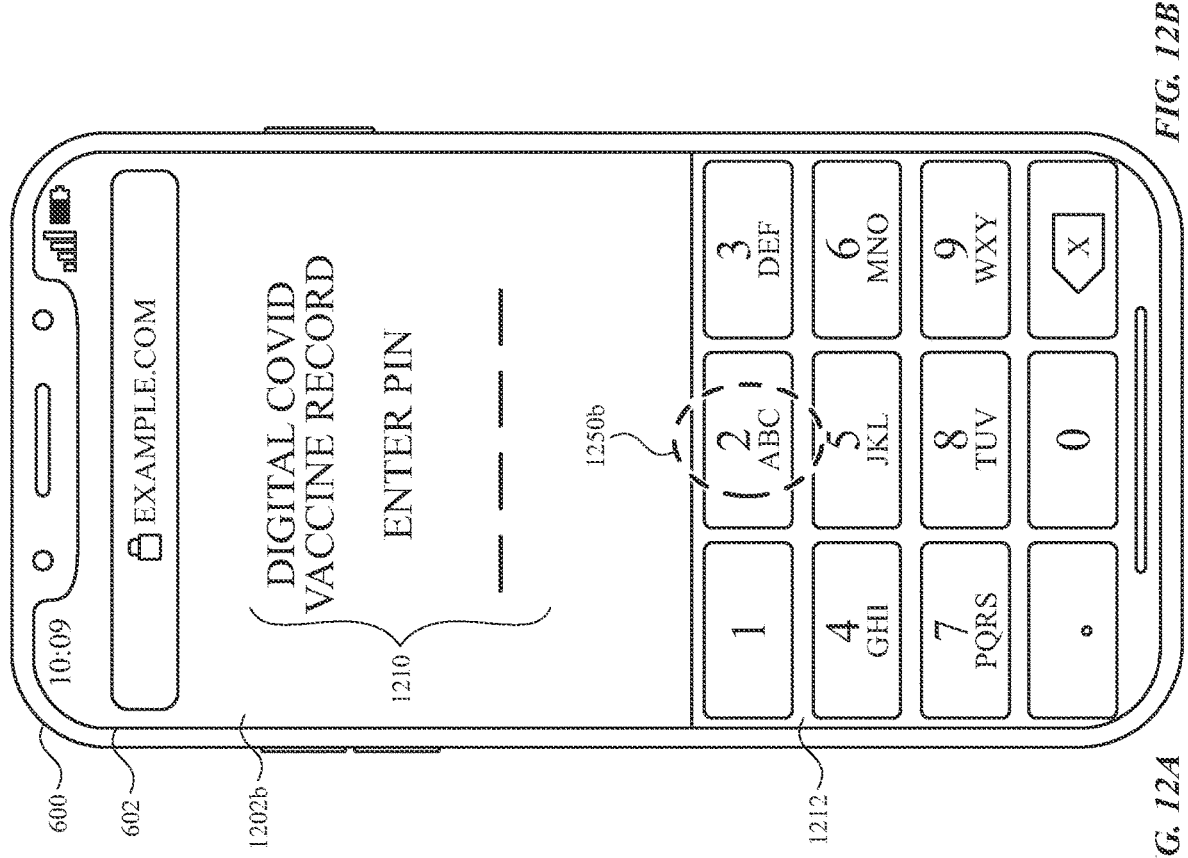
Figure 12A:
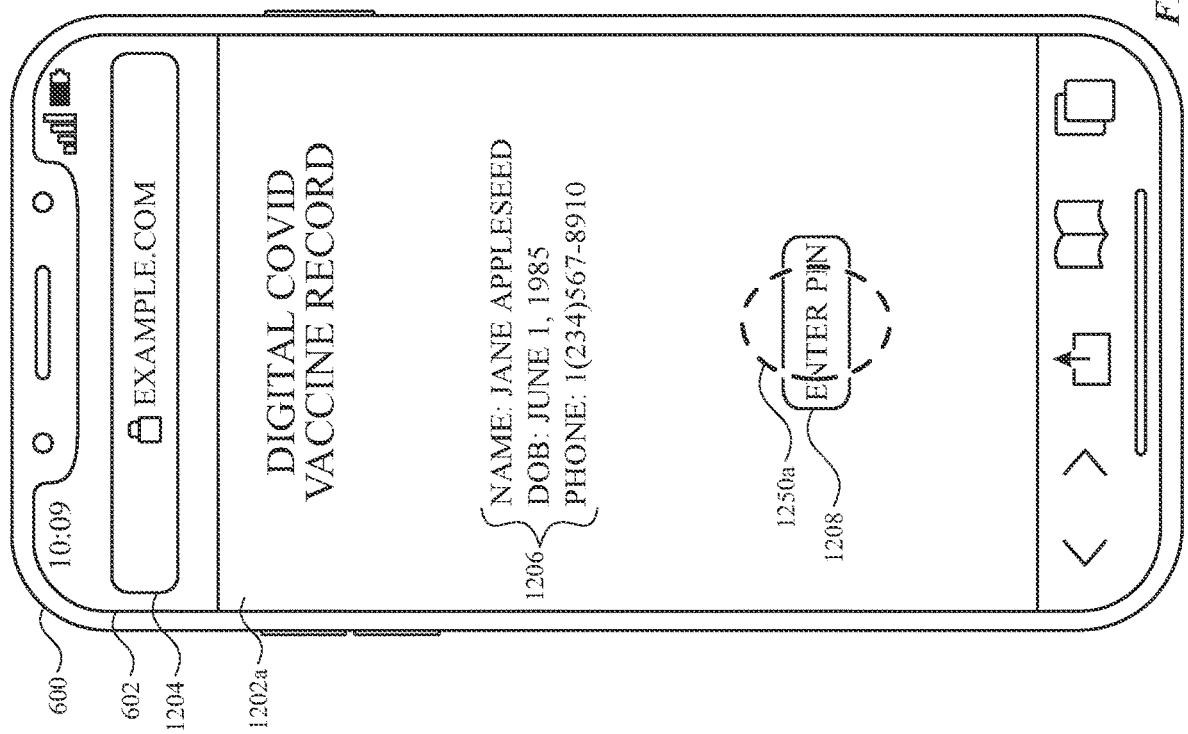

In FIG. 12A, computer system 600 displays third party user interface 1202*a*, which includes website 1204, that includes an indication of a website corresponding to third party user interface 1202*a*. Third party user interface 1202*a* further includes identifying information 1206, which includes text corresponding to identifying information (e.g., a name, a date of birth, a phone number) for an individual whose clinical record can be retrieved on website 1204. Third party user interface 1202*a* further includes pin affordance 1208 which, when selected, causes computer system 600 to display third party user interface 1202*b* that prompts the user to enter a pin to retrieve a digital vaccine record. In FIG. 12A, computer system receives input 1250*a* (e.g., a tap input) on pin affordance 1208.

In FIG. 12B, in response to receiving input 1250*a* on pin affordance 1208, computer system 600 displays third party user interface 1202*b*. Third party user interface 1202*b* is a user interface for entering a pin code to access a digital vaccine record. Third party user interface 1202*b* includes record info 1210, which includes a representation of the type of clinical record (e.g., a digital vaccine record) that a user can retrieve by entering a PIN code on third party user interface 1202. Third party user interface 1202*b* includes keypad 1212, which a user can use to enter a numerical pin to access the digital vaccine record (e.g., via touch inputs on the keypad). In FIG. 12B, computer system 600 receives input 1250*b*, which corresponds to an input entering a PIN code required to retrieve a digital vaccine record.

Figure 12D:
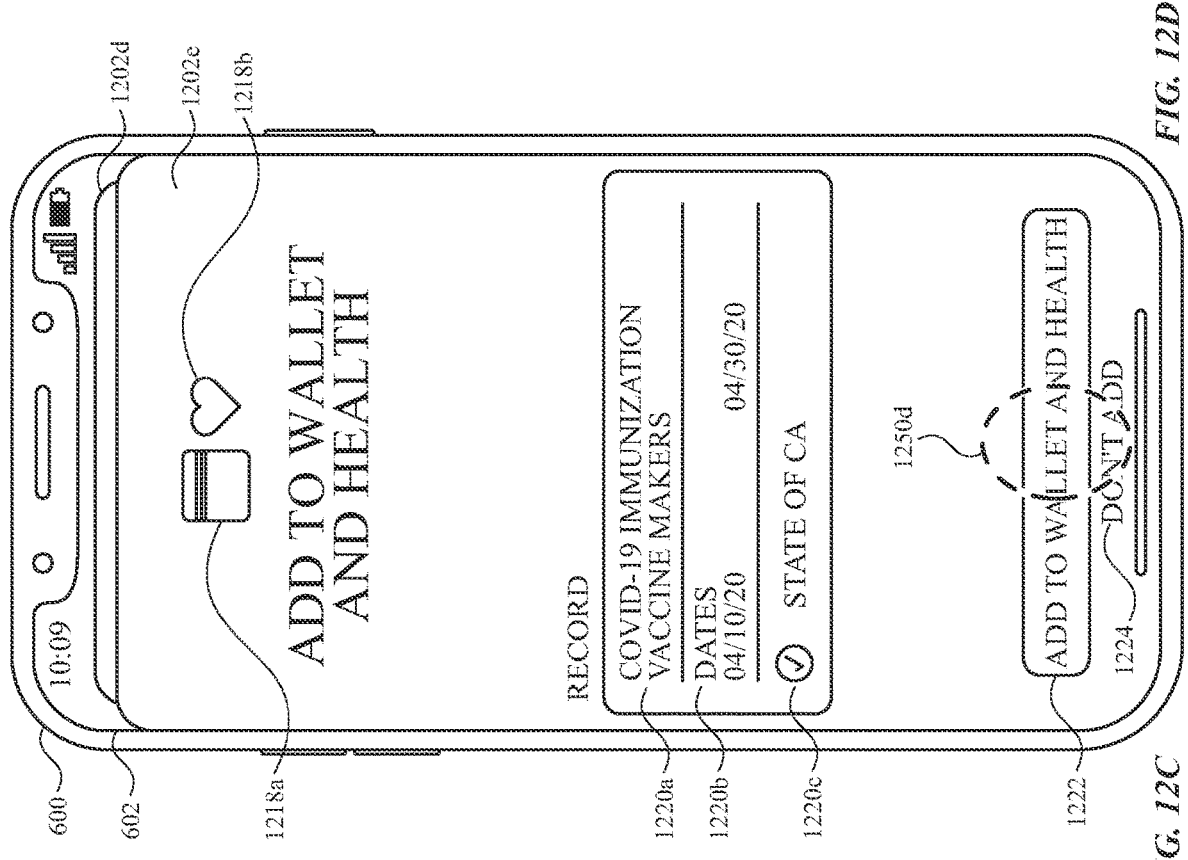
Figure 12C:
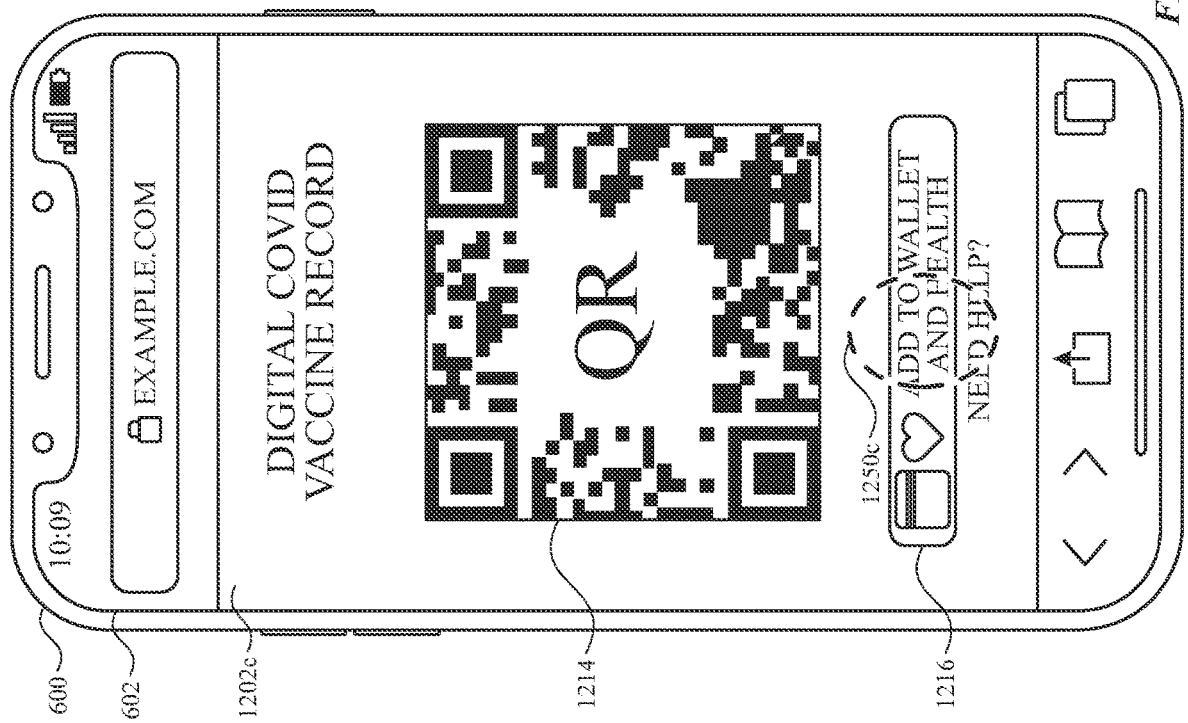

In FIG. 12C, in response to receiving one or more inputs corresponding to entry of a pin code on third party user interface 1202*b* as illustrated in FIG. 12B, computer system 600 displays third party user interface 1202*c*. Third party user interface 1202*c* includes QR code 1214, which corresponds to information related to a digital vaccine record. In some embodiments, QR code 1214 links to a digital vaccine record (e.g., a website containing information about the vaccine record). Third party user interface 1202*c* further includes add to wallet and health affordance 1216 which, when selected, initiates a process for adding the digital vaccine record corresponding to QR code 1214 to both a health application and a wallet application on computer system 600. In FIG. 12C, computer system 600 receives input 1250*c* on add to wallet and health affordance 1216.

In FIG. 12D, in response to receiving input 1250*c* on add to wallet and health affordance 1216, computer system 600 launches (e.g., opens) a health application, displays health user interface 1202*d*, and then displays add sheet 1202*e* at least partially overlaying health user interface 1202*d* such that at least a portion of health user interface 1202*d* is visible behind add sheet 1202*e* as illustrated in FIG. 12D. Add sheet 1202*e* includes wallet representation 1218*a*, which is a graphical representation of the wallet application to which the vaccine record is being added (e.g., a logo and/or icon associated with the wallet application). Add sheet 1202*e* further includes health representation 1218*b*, which is a graphical representation of the health application to which the vaccine record is being added (e.g., a logo and/or icon associated with the health application). Add sheet 1202*e* further includes information related to the vaccine record being added, including manufacturer 1220*a*, which includes an indication of the maker of the one or more vaccines included in the vaccine record, date 1220*b*, which includes an indication of the dates on which the one or more vaccines included in the vaccine record were administered, and verifier 1220*c*, which includes an indication of the verifier, agency, or governing body authenticating the vaccine record. Add sheet 1202*e* further includes add to wallet and health affordance 1222 which, when selected, causes the vaccine record to be added to the health application and the wallet application. Add sheet 1202*e* further includes do not add affordance 1224 which, when selected, causes the computer system to forego adding the vaccine record to the health application and the wallet application. In some embodiments, selecting do not add affordance 1224 causes add sheet 1202*e* to be dismissed, and for computer system 600 to return to displaying health user interface 1202*d* without adding the vaccine record to the health application or the wallet application. In FIG. 12D, computer system 600 receives input 1250*d* on add to wallet and health affordance 1222.

In FIG. 12E, in response to receiving input 1250*d* on add to wallet and health affordance 1222, computer system 600 adds the vaccine record to the health application and the wallet application and displays confirmation sheet 1202*f* As illustrated in FIG. 12E, confirmation sheet 1202*f* is at least partially overlaid on health user interface 1202*d* such that at least a portion of health user interface 1202*d* is displayed while confirmation sheet 1202*f* is displayed. Confirmation sheet 1202*f* is a user interface confirming to the user that the vaccine record has been added to the health application and the wallet application. Confirmation sheet 1202*f* includes wallet representation 1218*a* and health representation 1218*b*, as described above with reference to FIG. 12D. Confirmation sheet 1202*f* further includes confirmation 1226, which includes a textual and/or graphical indication that the vaccine record has been added. Confirmation sheet 1202*f* further includes view instructions 1228, which include textual and/or visual indications that the vaccine record can be viewed in the health application and wallet application to which the vaccine record has been added. Confirmation sheet 1202*f* further includes done affordance 1230 which, when selected, causes confirmation sheet 1202*f* to be dismissed and for computer system 600 to display health user interface 1202*g*. In FIG. 12E, computer system 600 receives input 1250*e* on done affordance 1230.

In FIG. 12F, in response to receiving input 1250*e* on done affordance 1230 as illustrated in FIG. 12E, computer system 600 displays health user interface 1202*g*. Health user interface 1202*g* includes information related to the vaccine record that was added to the health application (e.g., in FIG. 12E). Health user interface 1202*g* includes record type 1232, which includes a visual and/or textual indication of the type of clinical record that was added to the health application (e.g., an immunization record). Health user interface 1202*g* further includes record name 1234, which includes a visual and/or textual indication of the name of the record (e.g., a COVID-19 Vaccine). Health record user interface 1202*g* further includes recipient information 1236*a*, which includes a representation of the name of the patient to which the clinical record pertains, and birthday 1236*b*, which includes a representation of the date of the birth of the patient to which the clinical record pertains. Health record user interface 1202*g* further includes QR code 1214. Health record user interface 1202*g* further includes details affordance 1238 which, when selected, causes computer system 600 to display a user interface including information about multiple entries related to the clinical record (e.g., information about two or more doses of a vaccine in a series of vaccines associated with the clinical record). Health user interface 1202*g* further includes verifier 1236*c*, which includes an indication of the verifier, agency, or governing body authenticating the vaccine record. Health user interface 1202*g* further includes view in wallet affordance 1240 which, when selected, causes computer system 600 to display information related to the clinical record (e.g., the vaccine record) in the wallet application (e.g., by launching the wallet application). Health user interface 1202*g* further includes summary affordance 1242*a* which, when selected, causes computer system 600 to display a summary user interface of the health application. Health user interface 1202*g* further includes sharing affordance 1242*b* which, when selected, causes computer system 600 to display a sharing user interface of the health application. Health user interface 1202*g* further includes browse affordance 1242*c* which, when selected, causes computer system 600 to display a browse user interface of the health application. In some embodiments, summary affordance 1242*a*, sharing affordance 1242*b*, and browse affordance 1242*c* are displayed with a visually distinguishing quality (e.g., a bolded appearance, a different color, etc.) when the corresponding user interface is displayed (e.g., summary affordance 1242*a* can be displayed with a bolded appearance when a summary user interface of the health application is displayed). In FIG. 12F, computer system 600 receives user input 1250f on view in wallet affordance 1240. In some embodiments, in response to receiving user input 1250f on view in wallet affordance 1240, computer system launches (e.g., opens) the wallet application and displays a graphical representation of the vaccine record.

In some embodiments, a vaccine record can be added to the health application without being added to the wallet application. FIGS. 12G-12J illustrate exemplary user interfaces for adding a clinical record that has been added to the health application to the wallet application, in accordance with some embodiments. In one example, a vaccine record has been added to the health application, but has not been added to the wallet application. While the vaccine record is added to the health application but not the wallet application, the computer system receives a sequence of one or more user inputs corresponding to a request to launch (e.g., open) the health application. In some embodiments, in response to receiving the sequence of one or more user inputs corresponding to a request to launch the health application, computer system 600 displays health user interface 1202h, as illustrated in FIG. 12G.

In FIG. 12G, computer system 600 displays health user interface 1202h, which is a summary screen of the health application. Health user interface 1202h includes summary indication 1244, which includes a visual and/or textual indication that health user interface 1202h is a summary user interface. Health user interface 1202h further includes record availability indicator 1246, which includes a graphical and/or textual indication that the health application includes (e.g., has access to) a clinical record (e.g., a vaccine record) that can be added to the wallet application that has not yet been added to the wallet application. Health user interface 1202h further includes add to wallet affordance 1248 which, when selected, initiates a process for adding the clinical record (e.g., a vaccine record) that can be added to the wallet application that has not yet been added to the wallet application to the wallet application. Health user interface 1202h further includes physiological indicators 1252. Physiological indicators 1252 include visual and/or textual representations of information that has been added to (e.g., is stored in) the health application (e.g., activity information, heart rate, weight, clinical records information, physiological measurements). Health user interface 1202h further includes summary affordance 1242a, sharing affordance 1242b, and browse affordance 1242c, as described above with reference to FIG. 12F. In FIG. 12G, computer system 600 receives input 1250g on add to wallet affordance 1248 and, in response, displays add sheet 1202i as illustrated in FIG. 12H.

In FIG. 12H, in response to receiving input 1250g on add to wallet affordance 1248, computer system 600 displays add sheet 1202i at least partially overlaying health user interface 1202h such that at least a portion of health user interface 1202h is visible behind add sheet 1202i, as illustrated in FIG. 12H. Add sheet 1202i includes wallet representation 1218a, manufacturer 1220a, date 1220b, and verifier 1220c, as described above with reference to FIG. 12D. Add sheet 1202i further includes add to wallet affordance 1254 which, when selected, causes the vaccine record to be added to the wallet application. Add sheet 1202i further includes do not add affordance 1256 which, when selected, causes the computer system to forego adding the vaccine record to the wallet application. In some embodiments, selecting do not add affordance 1256 causes add sheet 1202i to be dismissed, and for computer system 600 to return to displaying health user interface 1202h without adding the vaccine record to the wallet application. In FIG. 12H, computer system 600 receives input 1250h on add to wallet affordance 1254.

In FIG. 12I, in response to receiving input 1250h on add to wallet affordance 1254 as illustrated in FIG. 12H, computer system 600 adds the vaccine record to the wallet application and displays confirmation sheet 1202j. As illustrated in FIG. 12I, confirmation sheet 1202j is at least partially overlaid on health user interface 1202h such that at least a portion of health user interface 1202h is displayed while confirmation sheet 1202j is displayed. Confirmation sheet 1202j is a user interface confirming to the user that the vaccine record has been added to the wallet application. Confirmation sheet 1202j includes wallet representation 1218a, as described above with reference to FIG. 12D. Confirmation sheet 1202j further includes confirmation 1257, which includes a textual and/or graphical indication that the vaccine record has been added to the wallet application. Confirmation sheet 1202j further includes view instructions 1258, which include textual and/or visual indications that the vaccine record can be viewed in the wallet applications to which the vaccine record has been added. Confirmation sheet 1202j further includes done affordance 1260 which, when selected, causes confirmation sheet 1202j to be dismissed and for computer system 600 to display health user interface 1202h. In FIG. 12I, computer system 600 receives input 1250i on done affordance 1260. In some embodiments, in response to receiving input 1250i on done affordance 1260, computer system displays health user interface 1202h. In some embodiments, in response to receiving input 1250i on done affordance 1260, computer system displays wallet user interface 1202k, as seen in FIG. 12J.

In FIG. 12J, computer system 600 displays wallet user interface 1202k. In some embodiments, after a clinical record (e.g., a vaccine record) has been added to the wallet application, computer system receives a user input (e.g., a double press input) corresponding to a request to view items that have been added to the wallet application (e.g., to view graphical representations of one or more bank cards, credit cards, clinical records, loyalty passes, transit passes, etc. that have been added to the wallet application). Wallet user interface 1202k illustrates a user interface containing graphical representations of at least some of the items that have been added to the wallet application, including payment items 1266, which includes graphical representations of payment cards that have been added to the wallet application. Wallet user interface 1202k further includes clinical record 1268, which includes a visual representation of a vaccine record that has been added to the wallet application. In some embodiments, clinical record 1268 includes a stacked or layered appearance as illustrated in FIG. 12J to illustrate that multiple items are associated with and/or included with the clinical record. For example, a clinical record that is a vaccine record with three doses of a vaccine may be illustrated as having three items layered on top of one another, as illustrated by clinical record 1268 in FIG. 12J. Wallet user interface 1202k further includes passes 1270, which includes graphical representations of additional items that have been added to the wallet application (e.g., boarding passes, loyalty cards, concert tickets, etc.). Wallet user interface 1202k further includes wallet indicator 1262, which includes a visual and/or textual indication that wallet user interface 1202k is associated with a digital wallet application. Wallet user interface 1202k further includes add affordance 1264 which, when selected, initiates a process for adding one or more items to the wallet application.

In some embodiments, in response to receiving the user input (e.g., a double press input) corresponding to a request to view items that have been added to the wallet application, computer system 600 conditionally displays a graphical representation of one or more clinical records that have been added to the wallet application based on a determination about whether computer system 600 is in a locked state or an unlocked state. In some embodiments, in response to receiving the user input (e.g., a double press input) corresponding to a request to view items that have been added to the wallet application, computer system displays graphical representations of items that have been added to the wallet application including one or more clinical records if the computer system is unlocked (e.g., in an unlocked state). In some embodiments, in response to receiving the user input (e.g., a double press input) corresponding to a request to view items that have been added to the wallet application, computer system displays graphical representations of items that have been added to the wallet application without including one or more clinical records if the computer system is locked (e.g., in a locked state).

FIG. 13 is a flow diagram illustrating a method for displaying user interfaces for adding clinical records to applications. Method 1300 is performed at a computer system (e.g., 100, 300, 500) that is in communication with a display generation component and one or more input devices (e.g., a mouse, a keyboard, a touch-sensitive surface). Some operations in method 1300 are, optionally, combined, the orders of some operations are, optionally, changed, and some operations are, optionally, omitted.

As described below, method 1300 provides an intuitive way for displaying user interfaces for adding clinical records to applications. The method reduces the cognitive burden on a user for adding clinical records to applications, thereby creating a more efficient human-machine interface. For battery-operated computing devices, enabling a user to add clinical records to applications faster and more efficiently conserves power and increases the time between battery charges.

The computer system (e.g., 600) (e.g., a smartphone, a smartwatch, a wearable electronic device, a desktop computer, a laptop, a tablet) displays (1302), via the display generation component (e.g., 602) (e.g., a display, a display controller), a clinical record user interface, wherein displaying the clinical record user interface includes concurrently displaying: a set of information (1304) corresponding to a clinical record (e.g., 1214) (e.g., a vaccine record, a test result, a lab result, a physiological measurement) and a user-interactive graphical user interface object (1306) (e.g., 1216) (e.g., an affordance) that, when selected, initiates a process for adding (e.g., concurrently adding) data corresponding to at least a portion of the set of information corresponding to the clinical record (e.g., data corresponding to a vaccine record, data corresponding to a test result, data corresponding to a lab result, data corresponding to a physiological measurement, etc.) to both a health application (e.g., a health application downloaded and/or installed on the computer system) and a wallet application (e.g., a wallet application downloaded and/or installed on the computer system). In some embodiments, the set of information is not currently stored in/associated with either the health application or the wallet application. In some embodiments, the health application is an application that stores health-related information (e.g., physiological, clinical, and/or fitness related information). In some embodiments, the wallet application is an application that stores one or more digital credentials for payments and/or for identifying a user of the computer system different from the health application.

While displaying (1308) the clinical record user interface, the computer system (e.g., 600) receives, via the one or more input devices (e.g., a mouse, a keyboard, a touch-sensitive surface), a user input (e.g., 1250c) that corresponds to selection (e.g., a tap gesture, a swipe, a press input, and/or a mouse click) of the user-interactive graphical user interface object (e.g., 1216).

In response to receiving (1310) the user input (e.g., 1250c) that corresponds to selection of the user-interactive graphical user interface object (e.g., 1216), the computer system (e.g., 600) initiates the process for adding data corresponding to at least the portion of the set of information corresponding to the clinical record to the health application and the wallet application. In some embodiments, the clinical record user interface is a third-party user interface (e.g., a website corresponding to a third party (e.g., an airline, a pharmacy, a glasses vendor) different from the manufacturer of the computer system (e.g., the provider of the operating system of the computer system), an application provided by (e.g., developed by) a third party different from the manufacturer of the computer system). In some embodiments, the health application and/or the wallet application are first-party applications (e.g., applications provided by (e.g., developed and/or distributed by) the provider of the operating system). In some embodiments, the health application is associated with clinical and/or health related information (e.g., vaccine records, test results, lab results, physiological measurements). In some embodiments, the wallet application is associated with payment and/or transaction information (e.g., credit card numbers, debit card numbers, transit passes). Initiating a process for adding data corresponding to at least the portion of the set of information corresponding to the clinical record to the health application and the wallet application in response to receiving the user input that corresponds to selection of the user-interactive graphical user interface object reduces the number of inputs needed to perform an operation (e.g., to add the data to both the health application and the wallet application).

In some embodiments, the clinical record is a vaccine record (e.g. 1214) (e.g., a vaccination card, a record that one or more vaccines have been administered). In some embodiments, the vaccine record includes information about the recipient of the vaccine, the manufacturer and/or provider of the vaccine, the lot number(s) of the vaccine(s), and/or the dates on which one or more vaccines were administered. In some embodiments, the vaccine record is a signed clinical record, as described with reference to FIGS. 8A-8E.

In some embodiments, initiating the process for adding data corresponding to at least the portion of the set of information corresponding to the clinical record to the health application and the wallet application includes adding data corresponding to at least a first portion of the set of information corresponding to the clinical record to the health application and adding data corresponding to at least a second portion of the set of information to the wallet application. In some embodiments, the first portion of the set of information corresponding to the clinical record and the second portion of the set of information corresponding to the clinical record are the same. In some embodiments, the first portion of the set of information corresponding to the clinical record and the second portion of the set of information corresponding to the clinical record are different. Adding data corresponding to at least a first portion of the set of information corresponding to the clinical record to the health application and adding data corresponding to at least a second portion of the set of information to the wallet application in response to receiving the user input that corresponds to selection of the user-interactive graphical user interface object reduces the number of inputs needed to perform an operation (e.g., to add the first portion of the set of information corresponding to the clinical record to the health application and the second portion of the set of information corresponding to the clinical record to the wallet application).

In some embodiments, in response to receiving the user input (e.g., 1250c) that corresponds to selection of the user-interactive graphical user interface object (e.g., 1216), the computer system (e.g., 600) launches (e.g., opens) the health application. In some embodiments, launching the health application includes displaying a user interface of the health application. In some embodiments, one or more steps of the process for adding data corresponding to at least the portion of the set of information corresponding to the clinical record to the health application and the wallet application are performed in the health application (e.g., in a user interface of the health application). Launching the health application and initiating the process for adding data corresponding to at least the portion of the set of information corresponding to the clinical record to the health application and the wallet application in response to receiving the user input that corresponds to selection of the user-interactive graphical user interface object reduces the number of inputs needed to perform an operation (e.g., to launch the health application and initiate the process for adding the data to the health and wallet application).

In some embodiments, in response to receiving the user input (e.g., 1250c) that corresponds to selection of the user-interactive graphical user interface object (e.g., 1216), the computer system (e.g., 600) displays, via the display generation component (e.g., 602), a confirmation user interface (e.g., 1202e), wherein displaying the confirmation user interface includes concurrently displaying: a representation of the clinical record (e.g., 1220a, 1220b, 1220c) (e.g., information corresponding to the clinical record (e.g., the recipient of one or more vaccines, the manufacturer and/or providers of one or more vaccines, the lot number of one or more vaccines, and/or the dates on which one or more vaccines were administered), a graphical representation of the clinical record), and an add user-interactive graphical user interface object (e.g., 1222) (e.g., an affordance) that, when selected, causes data corresponding to at least a portion of the set of information corresponding to the clinical record to be added to both the health application and the wallet application. In some embodiments, the confirmation user interface further includes a skip user-interactive graphical user interface object that, when selected, causes the computer system to forego adding data corresponding to the set of information corresponding to the clinical record to the health application and the wallet application. In some embodiments, the confirmation user interface is partially overlaid on a user interface of the health application such that at least a portion of the user interface of the health application is still visible while the confirmation user interface is displayed. Displaying a confirmation user interface that includes a representation of the clinical record and an add user-interactive graphical user interface object that, when selected, causes data corresponding to the set of information corresponding to the clinical record to be added to both the health application and the wallet application allows the user to quickly confirm that they want data corresponding to the clinical record to be added to the health application and the wallet application from the confirmation user interface, thereby providing improved visual feedback to the user.

In some embodiments, while displaying the confirmation user interface (e.g., 1202e), the computer system (e.g., 600) receives, via the one or more input devices, a user input (e.g., 1250d) that corresponds to selection (e.g., a tap gesture, a swipe, a press input, and/or a mouse click) of the add user-interactive graphical user interface object (e.g., 1222) and, in response to receiving the user input that corresponds to selection (e.g., a tap gesture, a swipe, a press input, and/or a mouse click) of the add user-interactive graphical user interface object: the computer system adds data corresponding to at least a third portion of the set of information corresponding to the clinical record to the health application and the computer system adds data corresponding to at least a fourth portion of the set of information to the wallet application. In some embodiments, the third portion of the set of information corresponding to the clinical record and the fourth portion of the set of information corresponding to the clinical record are the same. In some embodiments, the third portion of the set of information corresponding to the clinical record and the fourth portion of the set of information corresponding to the clinical record are different. In some embodiments, after adding data corresponding to the at least a portion of the set of information corresponding to the clinical record to the health application and the wallet application, the computer system transmits at least part of the portion of the set of information corresponding to the clinical record to a second computer system different from the first computer system (e.g., a computer system that is paired with and/or signed into the same user account as the computer system.) In some embodiments, after adding data corresponding to the at least a portion of the set of information corresponding to the clinical record to the health application and the wallet application, the computer system displays at least part of the portion of the set of information corresponding to the clinical record on a second computer system different from the first computer system. In some embodiments, in response to receiving the user input that corresponds to selection of the add user-interactive graphical user interface object, the computer system displays a user interface that includes a visual indication that the clinical record has been added to the health application and the wallet Application and/or a "Done" user-interactive graphical user interface object that, when selected, causes the user interface of the health application to be displayed. Adding data corresponding to at least a third portion of the set of information corresponding to the clinical record to the health application and adding data corresponding to at least a fourth portion of the set of information corresponding to the clinical record to the wallet application in response to receiving the user input that corresponds to selection of the add user-interactive graphical user interface object reduces the number of inputs needed to perform an operation (e.g., adding data to the health application and the wallet application).

In some embodiments, after completing the process for adding data corresponding to at least the portion of the set of information corresponding to the clinical record to the health application and the wallet application and while the data corresponding to at least the portion of the set of information corresponding to the clinical record is accessible from the health application and the wallet application, the computer system (e.g., 600) receives, at a first user interface of the health application, a sequence of user inputs (e.g., touch inputs, rotational inputs, press inputs) corresponding to a request to remove (e.g., delete) data corresponding to at least the portion of the set of information corresponding to the clinical record from the health application. In some embodiments, in response to receiving the sequence of user inputs corresponding to a request to remove data corresponding to at least the portion of the set of information corresponding to the clinical record from the health application: the computer system removes data corresponding to at least the portion of the set of information corresponding to the clinical record from the health application and the computer system removes data corresponding to at least the portion of the set of information corresponding to the clinical record from the wallet application. Removing data corresponding to at least the portion of the set of information corresponding to the clinical record from both the health application and the wallet application in response to receiving a sequence of user inputs corresponding to remove the data from the health application enables the computer system to automatically remove data from the wallet application when it is removed from the health application without requiring the user to manually remove the data from the wallet application, which performs an operation when a set of conditions has been met without requiring further user input, and reduces the number of inputs needed to perform an operation (e.g., to remove data corresponding to the clinical record from the health application and the wallet application).

In some embodiments, after completing the process for adding data corresponding to at least the portion of the set of information corresponding to the clinical record to the health application and the wallet application and while the data corresponding to at least the portion of the set of information corresponding to the clinical record is accessible from the health application and the wallet application, the computer system (e.g., 600) receives, at a first user interface of the wallet application, a sequence of user inputs (e.g., touch inputs, rotational inputs, press inputs) corresponding to a request to remove (e.g., delete) data corresponding to at least the portion of the set of information corresponding to the clinical record from the wallet application. In some embodiments, in response to receiving the sequence of user inputs corresponding to a request to remove data corresponding to at least the portion of the set of information corresponding to the clinical record from the wallet application, the computer system removes data corresponding to at least the portion of the set of information corresponding to the clinical record from the wallet application without removing the data corresponding to at least the portion of the set of information corresponding to the clinical record from the health application. Removing data corresponding to at least the portion of the set of information corresponding to the clinical record from the wallet application in response to receiving the sequence of user inputs corresponding to a request to remove data corresponding to at least the portion of the set of information corresponding to the clinical record from the wallet application reduces the number of inputs needed to perform an operation (e.g., to remove data from the wallet application).

In some embodiments, the wallet application includes (e.g., stores, has access to, is associated with) data corresponding to at least a first non-clinical item (e.g., 1266, 1270) (e.g., a payment card, an identification card, a credential, a driver's license, a transit pass). A wallet application that includes one or more clinical records and one or more items that are not clinical records reduces the number of inputs required to perform an operation (e.g., to view and/or access clinical records and items that are not clinical records from the same application, without needing to switch between different applications).

In some embodiments, after completing the process for adding data corresponding to at least the portion of the set of information corresponding to the clinical record to the health application and the wallet application, the computer system (e.g. 600) receives a request (e.g., a sequence of one or more user inputs (e.g., press inputs (e.g., a double press input), touch inputs, rotational inputs)) to display items included in the wallet application (e.g., 1266, 1268, 1270) (e.g., one or more clinical records, payment cards, identification cards, credentials, driver's licenses, or transit passes). In some embodiments, in response to receiving the request to display items included in the wallet application, in accordance with a determination that the computer system is in a locked state (e.g., a state where authentication (e.g., biometric authentication; passcode authentication) is required to unlock the computer system), the computer system displays, via the display generation component, a representation of the first non-clinical item (e.g., 1266, 1270) (e.g., a payment card, an identification card, a credential, a driver's license, a transit pass) included in the wallet application without displaying a representation of the clinical record (e.g., 1268) (e.g. a graphical representation corresponding to the clinical record, at least part of the data corresponding to at least a portion of the set of information corresponding to the clinical record) and in accordance with a determination that the computer system is in an unlocked state, the computer system concurrently displays, via the display generation component, a representation of the clinical record and the representation of the first non-clinical item included in the wallet application. Conditionally displaying a representation of the clinical record in response to detecting a request to display items included in the wallet application based on whether the computer system is locked without requiring the user to determine (e.g., manually) whether the representation of the clinical record should be displayed preserves potentially private information included in the clinical record by foregoing displaying the representation of the clinical record while the computer system is locked, which performs an operation when a set of conditions has been met without requiring further user input.

In some embodiments, the health application includes (e.g., stores, has access to, is associated with) data from one or more sensors (e.g., a step counter, a heart-rate sensor, an ECG) that are in communication with the computer system.

In some embodiments, the computer system (e.g., 600) receives a user input (e.g., a tap input) corresponding to a request to launch (e.g., open) the health application and, in response to receiving the user input corresponding to a request to launch the health application, the computer system displays, via the display generation component (e.g., 600), a health user interface (e.g., 1202h), wherein: in accordance with a determination that a second clinical record has been added to the health application that can be added to the wallet application (e.g., is compatible with being added to the wallet application) but has not been added to the wallet application, the health user interface includes a wallet user-interactive graphical user interface object (e.g., 1248) that, when selected, initiates a process for adding the second clinical record to the wallet application. In some embodiments, in accordance with a determination that the clinical records included in the health application that can be added to the wallet application have been added to the wallet application (e.g., have already been added), the health user interface does not include the wallet user-interactive graphical user interface object. In some embodiments, in response to receiving an input corresponding to selection of the wallet user-interactive graphical user interface object, the computer system displays an add sheet user interface that includes a continue user-interactive graphical user interface object that, when selected, causes the clinical record to be added to the wallet application. In some embodiments, the add sheet user interface further includes a forego user-interactive graphical user interface object that, when selected, causes the computer system to forego adding the clinical record to the wallet application. In some embodiments, the add sheet user interface is partially overlaid on a user interface of the health application such that at least a portion of the user interface of the health application is still visible while the add sheet user interface is displayed. Conditionally displaying a wallet user-interactive graphical user interface object based on a determination about whether the clinical records included in the health application that can be added to the wallet application have been added to the wallet application provides the user with knowledge about whether the clinical records in the health application that can be added to the wallet have already been added, without requiring the user to manually determine whether the clinical records included in the health application that can be added to the wallet application have been added to the wallet application performs an operation when a set of conditions has been met without requiring further user input.

In some embodiments, while displaying the health user interface (e.g., 1202h), the computer system (e.g., 600) receives a user input (e.g., a tap input) (e.g., 1250g) corresponding to a selection of the wallet user-interactive graphical user interface object (e.g., 1248). In some embodiments, in response to receiving the user input corresponding to selection of the wallet user-interactive graphical user interface object, the computer system (e.g., 600) adds the second clinical record to the wallet application. Adding data corresponding to at least a portion of the set of information to the wallet application in response to receiving the user input corresponding to selection of the wallet user-interactive graphical user interface object reduces the number of inputs needed to perform an operation (e.g., to add the data to the wallet application).

Note that details of the processes described above with respect to method 1300 (e.g., FIG. 13) are also applicable in an analogous manner to the methods described above. For example, method 1300 optionally includes one or more of the characteristics of the various methods described above with reference to method 900. For example, signed clinical record could be added to a wallet application and a health application as described above with reference to method 1300. For brevity, these details are not repeated below.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to allow users to view and manage signed clinical data that may be of interest to them. The present disclosure contemplates that in some instances, this gathered data may include personal information data that uniquely identifies or can be used to contact or locate a specific person. Such personal information data can include demographic data, location-based data, telephone numbers, email addresses, social network IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to display relevant signed clinical records. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of displaying signed clinical records, the present technology can be configured to allow users to select to "opt in" or "opt out" of participation in the collection of personal information data during registration for services or anytime thereafter. In another example, users can select not to provide clinical, health-related, or physiological measurements data for targeted content delivery services. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, signed clinical records can be displayed by inferring preferences based on non-personal information data or a bare minimum amount of personal information, such as the content being requested by the device associated with a user, other non-personal information available to the computer system, or publicly available information.

What is claimed is:

1. A computer system configured to communicate with a display generation component and one or more input devices, comprising:
   one or more processors; and
   memory storing one or more programs configured to be executed by the one or more processors, the one or more programs including instructions for:
   displaying, via the display generation component, a clinical record user interface, wherein displaying the clinical record user interface includes concurrently displaying:
      a set of information corresponding to a clinical record; and
      a user-interactive graphical user interface object that, when selected, initiates a process for adding data corresponding to at least a portion of the set of information corresponding to the clinical record to both a health application and a wallet application different from the health application; and
   while displaying the clinical record user interface, receiving, via the one or more input devices, a user input that corresponds to selection of the user-interactive graphical user interface object; and
   in response to receiving the user input that corresponds to selection of the user-interactive graphical user interface object, initiating the process for adding data corresponding to at least the portion of the set of information corresponding to the clinical record to the health application and the wallet application.

2. The computer system of claim 1, wherein the clinical record is a vaccine record.

3. The computer system of claim 1, wherein initiating the process for adding data corresponding to at least the portion of the set of information corresponding to the clinical record to the health application and the wallet application includes:
   adding data corresponding to at least a first portion of the set of information corresponding to the clinical record to the health application; and
   adding data corresponding to at least a second portion of the set of information to the wallet application.

4. The computer system of claim 1, the one or more programs including instructions for:
   in response to receiving the user input that corresponds to selection of the user-interactive graphical user interface object, launching the health application.

5. The computer system of claim 1, the one or more programs including instructions for:
   in response to receiving the user input that corresponds to selection of the user-interactive graphical user interface object, displaying, via the display generation component, a confirmation user interface, wherein displaying the confirmation user interface includes concurrently displaying:
      a representation of the clinical record; and
      an add user-interactive graphical user interface object that, when selected, causes data corresponding to at least a portion of the set of information corresponding to the clinical record to be added to both the health application and the wallet application.

6. The computer system of claim 5, the one or more programs including instructions for:
   while displaying the confirmation user interface, receiving, via the one or more input devices, a user input that corresponds to selection of the add user-interactive graphical user interface object; and
   in response to receiving the user input that corresponds to selection of the add user-interactive graphical user interface object:
      adding data corresponding to at least a third portion of the set of information corresponding to the clinical record to the health application; and
      adding data corresponding to at least a fourth portion of the set of information to the wallet application.

7. The computer system of claim 1, the one or more programs including instructions for:
   after completing the process for adding data corresponding to at least the portion of the set of information corresponding to the clinical record to the health application and the wallet application and while the data corresponding to at least the portion of the set of information corresponding to the clinical record is accessible from the health application and the wallet application:
      receiving, at a first user interface of the health application, a sequence of user inputs corresponding to a request to remove data corresponding to at least the portion of the set of information corresponding to the clinical record from the health application; and
      in response to receiving the sequence of user inputs corresponding to a request to remove data corresponding to at least the portion of the set of information corresponding to the clinical record from the health application:
removing data corresponding to at least the portion of the set of information corresponding to the clinical record from the health application; and
removing data corresponding to at least the portion of the set of information corresponding to the clinical record from the wallet application.

8. The computer system of claim 1, the one or more programs including instructions for:
after completing the process for adding data corresponding to at least the portion of the set of information corresponding to the clinical record to the health application and the wallet application and while the data corresponding to at least the portion of the set of information corresponding to the clinical record is accessible from the health application and the wallet application:
receiving, at a first user interface of the wallet application, a sequence of user inputs corresponding to a request to remove data corresponding to at least the portion of the set of information corresponding to the clinical record from the wallet application; and
in response to receiving the sequence of user inputs corresponding to a request to remove data corresponding to at least the portion of the set of information corresponding to the clinical record from the wallet application, removing data corresponding to at least the portion of the set of information corresponding to the clinical record from the wallet application without removing the data corresponding to at least the portion of the set of information corresponding to the clinical record from the health application.

9. The computer system of claim 1, wherein the wallet application includes data corresponding to at least a first non-clinical item.

10. The computer system of claim 9, the one or more programs including instructions for:
after completing the process for adding data corresponding to at least the portion of the set of information corresponding to the clinical record to the health application and the wallet application:
receiving a request to display items included in the wallet application;
in response to receiving the request to display items included in the wallet application:
in accordance with a determination that the computer system is in a locked state, displaying, via the display generation component, a representation of the first non-clinical item included in the wallet application without displaying a representation of the clinical record; and
in accordance with a determination that the computer system is in an unlocked state, concurrently displaying, via the display generation component, a representation of the clinical record and the representation of the first non-clinical item included in the wallet application.

11. The computer system of claim 1, wherein the health application includes data from one or more sensors that are in communication with the computer system.

12. The computer system of claim 1, the one or more programs including instructions for:
receiving a user input corresponding to a request to launch the health application;
in response to receiving the user input corresponding to a request to launch the health application, displaying, via the display generation component, a health user interface, wherein:
in accordance with a determination that a second clinical record has been added to the health application that can be added to the wallet application but has not been added to the wallet application, the health user interface includes a wallet user-interactive graphical user interface object that, when selected, initiates a process for adding the second clinical record to the wallet application; and
in accordance with a determination that the clinical records included in the health application that can be added to the wallet application have been added to the wallet application, the health user interface does not include the wallet user-interactive graphical user interface object.

13. The computer system of claim 12, the one or more programs including instructions for:
while displaying the health user interface, receiving a user input corresponding to a selection of the wallet user-interactive graphical user interface object; and
in response to receiving the user input corresponding to selection of the wallet user-interactive graphical user interface object, adding the second clinical record to the wallet application.

14. A non-transitory computer-readable storage medium storing one or more programs configured to be executed by one or more processors of a computer system that is in communication with a display generation component and one or more input devices, the one or more programs including instructions for:
displaying, via the display generation component, a clinical record user interface, wherein displaying the clinical record user interface includes concurrently displaying:
a set of information corresponding to a clinical record; and
a user-interactive graphical user interface object that, when selected, initiates a process for adding data corresponding to at least a portion of the set of information corresponding to the clinical record to both a health application and a wallet application different from the health application; and
while displaying the clinical record user interface, receiving, via the one or more input devices, a user input that corresponds to selection of the user-interactive graphical user interface object; and
in response to receiving the user input that corresponds to selection of the user-interactive graphical user interface object, initiating the process for adding data corresponding to at least the portion of the set of information corresponding to the clinical record to the health application and the wallet application.

15. The non-transitory computer-readable storage medium of claim 14, wherein the clinical record is a vaccine record.

16. The non-transitory computer-readable storage medium of claim 14, wherein initiating the process for adding data corresponding to at least the portion of the set of information corresponding to the clinical record to the health application and the wallet application includes:
adding data corresponding to at least a first portion of the set of information corresponding to the clinical record to the health application; and adding data corresponding to at least a second portion of the set of information to the wallet application.

17. The non-transitory computer-readable storage medium of claim 14, the one or more programs including instructions for:
in response to receiving the user input that corresponds to selection of the user-interactive graphical user interface object, launching the health application.

18. The non-transitory computer-readable storage medium of claim 14, the one or more programs including instructions for:
in response to receiving the user input that corresponds to selection of the user-interactive graphical user interface object, displaying, via the display generation component, a confirmation user interface, wherein displaying the confirmation user interface includes concurrently displaying:
a representation of the clinical record; and
an add user-interactive graphical user interface object that, when selected, causes data corresponding to at least a portion of the set of information corresponding to the clinical record to be added to both the health application and the wallet application.

19. The non-transitory computer-readable storage medium of claim 18, the one or more programs including instructions for:
while displaying the confirmation user interface, receiving, via the one or more input devices, a user input that corresponds to selection of the add user-interactive graphical user interface object; and
in response to receiving the user input that corresponds to selection of the add user- interactive graphical user interface object:
adding data corresponding to at least a third portion of the set of information corresponding to the clinical record to the health application; and
adding data corresponding to at least a fourth portion of the set of information to the wallet application.

20. The non-transitory computer-readable storage medium of claim 14, the one or more programs including instructions for:
after completing the process for adding data corresponding to at least the portion of the set of information corresponding to the clinical record to the health application and the wallet application and while the data corresponding to at least the portion of the set of information corresponding to the clinical record is accessible from the health application and the wallet application:
receiving, at a first user interface of the health application, a sequence of user inputs corresponding to a request to remove data corresponding to at least the portion of the set of information corresponding to the clinical record from the health application; and
in response to receiving the sequence of user inputs corresponding to a request to remove data corresponding to at least the portion of the set of information corresponding to the clinical record from the health application:
removing data corresponding to at least the portion of the set of information corresponding to the clinical record from the health application; and
removing data corresponding to at least the portion of the set of information corresponding to the clinical record from the wallet application.

21. The non-transitory computer-readable storage medium of claim 14, the one or more programs including instructions for:
after completing the process for adding data corresponding to at least the portion of the set of information corresponding to the clinical record to the health application and the wallet application and while the data corresponding to at least the portion of the set of information corresponding to the clinical record is accessible from the health application and the wallet application:
receiving, at a first user interface of the wallet application, a sequence of user inputs corresponding to a request to remove data corresponding to at least the portion of the set of information corresponding to the clinical record from the wallet application; and
in response to receiving the sequence of user inputs corresponding to a request to remove data corresponding to at least the portion of the set of information corresponding to the clinical record from the wallet application, removing data corresponding to at least the portion of the set of information corresponding to the clinical record from the wallet application without removing the data corresponding to at least the portion of the set of information corresponding to the clinical record from the health application.

22. The non-transitory computer-readable storage medium of claim 14, wherein the wallet application includes data corresponding to at least a first non-clinical item.

23. The non-transitory computer-readable storage medium of claim 22, the one or more programs including instructions for:
after completing the process for adding data corresponding to at least the portion of the set of information corresponding to the clinical record to the health application and the wallet application:
receiving a request to display items included in the wallet application;
in response to receiving the request to display items included in the wallet application:
in accordance with a determination that the computer system is in a locked state, displaying, via the display generation component, a representation of the first non-clinical item included in the wallet application without displaying a representation of the clinical record; and
in accordance with a determination that the computer system is in an unlocked state, concurrently displaying, via the display generation component, a representation of the clinical record and the representation of the first non-clinical item included in the wallet application.

24. The non-transitory computer-readable storage medium of claim 14, wherein the health application includes data from one or more sensors that are in communication with the computer system.

25. The non-transitory computer-readable storage medium of claim 14, the one or more programs including instructions for:
receiving a user input corresponding to a request to launch the health application;
in response to receiving the user input corresponding to a request to launch the health application, displaying, via the display generation component, a health user interface, wherein:

in accordance with a determination that a second clinical record has been added to the health application that can be added to the wallet application but has not been added to the wallet application, the health user interface includes a wallet user-interactive graphical user interface object that, when selected, initiates a process for adding the second clinical record to the wallet application; and in accordance with a determination that the clinical records included in the health application that can be added to the wallet application have been added to the wallet application, the health user interface does not include the wallet user-interactive graphical user interface object.

26. The non-transitory computer-readable storage medium of claim 25, the one or more programs including instructions for:

while displaying the health user interface, receiving a user input corresponding to a selection of the wallet user-interactive graphical user interface object; and in response to receiving the user input corresponding to selection of the wallet user-interactive graphical user interface object, adding the second clinical record to the wallet application.

27. A method, comprising:

at a computer system that is in communication with a display generation component and one or more input devices:

displaying, via the display generation component, a clinical record user interface, wherein displaying the clinical record user interface includes concurrently displaying:

a set of information corresponding to a clinical record; and a user-interactive graphical user interface object that, when selected, initiates a process for adding data corresponding to at least a portion of the set of information corresponding to the clinical record to both a health application and a wallet application different from the health application; and while displaying the clinical record user interface, receiving, via the one or more input devices, a user input that corresponds to selection of the user-interactive graphical user interface object; and in response to receiving the user input that corresponds to selection of the user-interactive graphical user interface object, initiating the process for adding data corresponding to at least the portion of the set of information corresponding to the clinical record to the health application and the wallet application.

28. The method of claim 27, wherein the clinical record is a vaccine record.

29. The method of claim 27, wherein initiating the process for adding data corresponding to at least the portion of the set of information corresponding to the clinical record to the health application and the wallet application includes:

adding data corresponding to at least a first portion of the set of information corresponding to the clinical record to the health application; and adding data corresponding to at least a second portion of the set of information to the wallet application.

30. The method of claim 27, further comprising:

in response to receiving the user input that corresponds to selection of the user-interactive graphical user interface object, launching the health application.

31. The method of claim 27, further comprising:

in response to receiving the user input that corresponds to selection of the user-interactive graphical user interface object, displaying, via the display generation component, a confirmation user interface, wherein displaying the confirmation user interface includes concurrently displaying:

a representation of the clinical record; and an add user-interactive graphical user interface object that, when selected, causes data corresponding to at least a portion of the set of information corresponding to the clinical record to be added to both the health application and the wallet application.

32. The method of claim 31, further comprising:

while displaying the confirmation user interface, receiving, via the one or more input devices, a user input that corresponds to selection of the add user-interactive graphical user interface object; and in response to receiving the user input that corresponds to selection of the add user- interactive graphical user interface object:

adding data corresponding to at least a third portion of the set of information corresponding to the clinical record to the health application; and adding data corresponding to at least a fourth portion of the set of information to the wallet application.

33. The method of claim 27, further comprising:

after completing the process for adding data corresponding to at least the portion of the set of information corresponding to the clinical record to the health application and the wallet application and while the data corresponding to at least the portion of the set of information corresponding to the clinical record is accessible from the health application and the wallet application:

receiving, at a first user interface of the health application, a sequence of user inputs corresponding to a request to remove data corresponding to at least the portion of the set of information corresponding to the clinical record from the health application; and in response to receiving the sequence of user inputs corresponding to a request to remove data corresponding to at least the portion of the set of information corresponding to the clinical record from the health application:

removing data corresponding to at least the portion of the set of information corresponding to the clinical record from the health application; and removing data corresponding to at least the portion of the set of information corresponding to the clinical record from the wallet application.

34. The method of claim 27, further comprising:

after completing the process for adding data corresponding to at least the portion of the set of information corresponding to the clinical record to the health application and the wallet application and while the data corresponding to at least the portion of the set of information corresponding to the clinical record is accessible from the health application and the wallet application:

receiving, at a first user interface of the wallet application, a sequence of user inputs corresponding to a request to remove data corresponding to at least the portion of the set of information corresponding to the clinical record from the wallet application; and in response to receiving the sequence of user inputs corresponding to a request to remove data corresponding to at least the portion of the set of information corresponding to the clinical record from the wallet application, removing data corresponding to at least the portion of the set of information corresponding to the clinical record from the wallet application without removing the data corresponding to at least the portion of the set of information corresponding to the clinical record from the health application.

35. The method of claim 27, wherein the wallet application includes data corresponding to at least a first non-clinical item.

36. The method of claim 27, further comprising:
after completing the process for adding data corresponding to at least the portion of the set of information corresponding to the clinical record to the health application and the wallet application:
  receiving a request to display items included in the wallet application;
  in response to receiving the request to display items included in the wallet application:
    in accordance with a determination that the computer system is in a locked state, displaying, via the display generation component, a representation of the first non-clinical item included in the wallet application without displaying a representation of the clinical record; and
    in accordance with a determination that the computer system is in an unlocked state, concurrently displaying, via the display generation component, a representation of the clinical record and the representation of the first non-clinical item included in the wallet application.

37. The method of claim 27, wherein the health application includes data from one or more sensors that are in communication with the computer system.

38. The method of claim 27, further comprising:
receiving a user input corresponding to a request to launch the health application;
in response to receiving the user input corresponding to a request to launch the health application, displaying, via the display generation component, a health user interface, wherein:
  in accordance with a determination that a second clinical record has been added to the health application that can be added to the wallet application but has not been added to the wallet application, the health user interface includes a wallet user-interactive graphical user interface object that, when selected, initiates a process for adding the second clinical record to the wallet application; and
  in accordance with a determination that the clinical records included in the health application that can be added to the wallet application have been added to the wallet application, the health user interface does not include the wallet user-interactive graphical user interface object.

39. The method of claim 27, further comprising:
while displaying the health user interface, receiving a user input corresponding to a selection of the wallet user-interactive graphical user interface object; and
in response to receiving the user input corresponding to selection of the wallet user- interactive graphical user interface object, adding the second clinical record to the wallet application.

\* \* \* \* \*

UNITED STATES PATENT AND TRADEMARK OFFICE
CERTIFICATE OF CORRECTION

PATENT NO. : 12,380,971 B2  
APPLICATION NO. : 17/832499  
DATED : August 5, 2025  
INVENTOR(S) : Matthew W. Crowley et al.

It is certified that error appears in the above-identified patent and that said Letters Patent is hereby corrected as shown below:

In the Claims

Column 79, Line 33: In Claim 19, delete "user- interactive" and insert -- user-interactive --.

Column 81, Line 23: In Claim 26, delete "user- interactive" and insert -- user-interactive --.

Column 82, Line 19: In Claim 32, delete "user- interactive" and insert -- user-interactive --.

Column 84, Line 30: In Claim 39, delete "user- interactive" and insert -- user-interactive --.

Signed and Sealed this  
Twenty-first Day of October, 2025

John A. Squires  
*Director of the United States Patent and Trademark Office*